US009287512B2

(12) United States Patent
Ahn et al.

(10) Patent No.: US 9,287,512 B2
(45) Date of Patent: Mar. 15, 2016

(54) ORGANIC ELECTROLUMINESCENT COMPOUNDS, LAYERS AND ORGANIC ELECTROLUMINESCENT DEVICE USING THE SAME

(71) Applicant: Rohm and Haas Electronic Materials Korea Ltd., Chungcheongnam-do (KR)

(72) Inventors: Hee-Choon Ahn, Gyeonggi-do (KR); Young-Jun Cho, Gyeonggi-do (KR); Hyuck Joo Kwon, Gyeonggi-do (KR); Bong-Ok Kim, Seoul (KR); Seok Keun Yoon, Gyeonggi-do (KR); Doo-Hyeon Moon, Gyeonggi-do (KR); Hee Sook Kim, Gyeonggi-do (KR); Su-Hyun Lee, Gyeonggi-do (KR); Hyo-Nim Shin, Gyeonggi-do (KR); Kyung Joo Lee, Gyeonggi-do (KR); Kyoung-Jin Park, Gyeonggi-do (KR); Nam-Kyun Kim, Gyeonggi-do (KR)

(73) Assignee: Rohm and Haas Electronic Materials Korea Ltd., Chungcheongnam-Do (KR)

( * ) Notice: Subject to any disclaimer, the term of this patent is extended or adjusted under 35 U.S.C. 154(b) by 0 days.

(21) Appl. No.: 14/825,517

(22) Filed: Aug. 13, 2015

(65) Prior Publication Data

US 2015/0357583 A1     Dec. 10, 2015

Related U.S. Application Data

(63) Continuation of application No. 14/624,835, filed on Feb. 18, 2015, which is a continuation of application No. 14/004,089, filed as application No. PCT/KR2012/001712 on Mar. 8, 2012, now abandoned.

(30) Foreign Application Priority Data

Mar. 8, 2011    (KR) ........................ 10-2011-0020492

(51) Int. Cl.
    *C07D 487/14*     (2006.01)
    *C07D 403/14*     (2006.01)
    *C09K 11/06*      (2006.01)
    *H01L 27/32*      (2006.01)
    *H01L 51/00*      (2006.01)
    *H01L 51/50*      (2006.01)

(52) U.S. Cl.
    CPC ............ *H01L 51/0072* (2013.01); *C09K 11/06* (2013.01); *H01L 51/0052* (2013.01); *H01L 51/0054* (2013.01); *H01L 51/0055* (2013.01); *H01L 51/0067* (2013.01); *H01L 51/0073* (2013.01); *H01L 51/0074* (2013.01); *H01L 51/0085* (2013.01); *H01L 51/0094* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *C09K 2211/185* (2013.01); *H01L 51/5012* (2013.01)

(58) Field of Classification Search
    CPC ..... C07D 403/14; C07D 487/14; C09K 11/06; H01L 27/32
    See application file for complete search history.

(56) References Cited

U.S. PATENT DOCUMENTS

| | | | |
|---|---|---|---|
| 2,954,377 | A | 9/1960 | Schwarze et al. |
| 4,719,174 | A | 1/1988 | Hirano et al. |
| 4,819,057 | A | 4/1989 | Naito et al. |
| 5,059,863 | A | 10/1991 | Tashiro et al. |
| 5,104,749 | A | 4/1992 | Sato et al. |
| 5,391,681 | A | 2/1995 | Mühleback et al. |
| 6,660,410 | B2 | 12/2003 | Hosokawa |
| 7,990,046 | B2 | 8/2011 | Iwakuma et al. |
| 8,227,798 | B2 | 7/2012 | Kai et al. |
| 8,247,089 | B2 | 8/2012 | Otsu et al. |
| 8,247,575 | B2 | 8/2012 | Nomura et al. |
| 8,530,658 | B2 | 9/2013 | Nomura et al. |
| 8,652,654 | B2 | 2/2014 | Inoue et al. |
| 8,685,543 | B2 | 4/2014 | Iwakuma et al. |
| 8,865,323 | B2 | 10/2014 | Inoue |
| 8,877,352 | B2 | 11/2014 | Inoue et al. |
| 8,895,159 | B2 | 11/2014 | Mizuki et al. |
| 8,911,886 | B2 | 12/2014 | Iwakuma et al. |
| 2001/0015614 | A1 | 8/2001 | Taguchi |
| 2001/0046612 | A1 | 11/2001 | Lee et al. |
| 2002/0028329 | A1 | 3/2002 | Ise et al. |
| 2002/0045061 | A1 | 4/2002 | Hosokawa |

(Continued)

FOREIGN PATENT DOCUMENTS

| | | |
|---|---|---|
| EP | 0517542 A1 | 12/1992 |
| EP | 1205527 A | 5/2002 |

(Continued)

OTHER PUBLICATIONS

International Preliminary Report on Patentability dated Feb. 14, 2012 (Appln. No. PCT/KR2010/005092).
International Preliminary Report on Patentability dated Sep. 10, 2013 (Appln. No. PCT/KR2012/001712).
International Search Report & Written Opinion dated Nov. 25, 2010 (Appln. No. PCT/KR2010/005092).
International Search Report & Written Opinion dated Jul. 18, 2012 (Appln. No. PCT/KR2012/001712).
Office Action Dated Jul. 16, 2014 in U.S. Appl. No. 13/389,750.
Office Action Dated Aug. 20, 2014 in U.S. Appl. No. 14/004,089.

(Continued)

*Primary Examiner* — Erich A Leeser
(74) *Attorney, Agent, or Firm* — The Dobrusin Law Firm, PC

(57) ABSTRACT

The present invention relates to a novel organic electroluminescent compound, layer and an organic electroluminescent device using the same. Said organic luminescent compound provides an organic light emitting layer and/or device which has high luminous efficiency and a long operation lifetime and requires a low driving voltage improving power efficiency and power consumption.

20 Claims, No Drawings

(56) References Cited

U.S. PATENT DOCUMENTS

| | | | |
|---|---|---|---|
| 2002/0055014 A1 | 5/2002 | Okada et al. |
| 2003/0129448 A1 | 7/2003 | Lin et al. |
| 2003/0205696 A1 | 11/2003 | Thoms et al. |
| 2004/0110031 A1 | 6/2004 | Fukuda et al. |
| 2005/0127823 A1 | 6/2005 | Iwakuma et al. |
| 2007/0248841 A1 | 10/2007 | Hosokawa |
| 2008/0054799 A1 | 3/2008 | Satou |
| 2009/0085479 A1 | 4/2009 | Ushikubo et al. |
| 2009/0091240 A1 | 4/2009 | Ikeda et al. |
| 2009/0134784 A1 | 5/2009 | Lin et al. |
| 2009/0167165 A1 | 7/2009 | Otsu et al. |
| 2009/0302745 A1 | 12/2009 | Otsu et al. |
| 2009/0317539 A1 | 12/2009 | Shitagaki et al. |
| 2010/0044695 A1 | 2/2010 | Kai et al. |
| 2010/0237339 A1 | 9/2010 | Nomura et al. |
| 2010/0237773 A1 | 9/2010 | Nomura et al. |
| 2011/0031484 A1 | 2/2011 | Lee et al. |
| 2011/0163660 A1 | 7/2011 | Hosokawa |
| 2011/0210318 A1 | 9/2011 | Bae et al. |
| 2011/0278552 A1 | 11/2011 | Numata et al. |
| 2011/0278555 A1 | 11/2011 | Inoue et al. |
| 2012/0138912 A1 | 6/2012 | Inoue et al. |
| 2012/0217485 A1 | 8/2012 | Lee et al. |
| 2012/0235123 A1 | 9/2012 | Lee et al. |
| 2012/0302751 A1 | 11/2012 | Nomura et al. |
| 2013/0306963 A1 | 11/2013 | Yamamoto et al. |
| 2014/0107338 A1 | 4/2014 | Ahn et al. |
| 2014/0114069 A1 | 4/2014 | Kim et al. |
| 2014/0239282 A1 | 8/2014 | Hosokawa |
| 2015/0008423 A1 | 1/2015 | Inoue et al. |
| 2015/0171341 A1 | 6/2015 | Lee et al. |
| 2015/0171346 A1 | 6/2015 | Ahn et al. |
| 2015/0228912 A1 | 8/2015 | Inoue et al. |

FOREIGN PATENT DOCUMENTS

| | | | |
|---|---|---|---|
| JP | 08/012430 B | 1/1996 |
| JP | 09/118708 A | 5/1997 |
| JP | 10/226785 A | 8/1998 |
| JP | 11/144876 A | 5/1999 |
| JP | 11/329737 A | 11/1999 |
| JP | 2000/53956 A | 2/2000 |
| JP | 2000/75519 A | 3/2000 |
| JP | 2000/260565 A | 9/2000 |
| JP | 2000/264880 A | 9/2000 |
| JP | 2000/268961 A | 9/2000 |
| JP | 2000/290644 A | 10/2000 |
| JP | 2000/328052 A | 11/2000 |
| JP | 2000/344780 A | 12/2000 |
| JP | 2001/247858 A | 9/2001 |
| JP | 2002/50478 A | 2/2002 |
| JP | 2002/71398 A | 3/2002 |
| JP | 2003/45662 A | 2/2003 |
| JP | 2005/203293 A | 7/2005 |
| JP | 2006/352046 A | 12/2006 |
| JP | 2008/3547 A | 1/2008 |
| JP | 2008/135498 A | 6/2008 |
| JP | 2010/97317 A | 4/2010 |
| JP | 2010/114180 A | 5/2010 |
| JP | 2010/291138 | 12/2010 |
| JP | 5120398 B | 11/2012 |
| KR | 10-1985-0000449 | 2/1985 |
| KR | 10-2002-0019534 A | 3/2002 |
| KR | 10-2007-0073868 A | 7/2007 |
| KR | 10-2010-0023783 A | 3/2010 |
| KR | 10-2010-079458 A | 7/2010 |
| KR | 10-2010-0105501 A | 9/2010 |
| KR | 10-2011-013220 A | 2/2011 |
| KR | 10-2011-0015836 A | 2/2011 |
| KR | 10-2012-013173 A | 2/2012 |
| KR | 10-2012-0057561 A | 6/2012 |
| WO | 01/19939 A | 3/2001 |
| WO | 01/72927 A1 | 4/2001 |
| WO | 03/078541 A1 | 9/2003 |
| WO | 2004/066315 A2 | 8/2004 |
| WO | 2006/025186 A1 | 3/2006 |
| WO | 2007/119816 A1 | 10/2007 |
| WO | 2008/090912 A1 | 7/2008 |
| WO | 2008/123189 A1 | 10/2008 |
| WO | 2011/019156 A1 | 2/2011 |
| WO | WO 2011/019156 * | 2/2011 | ............ C09K 11/06 |
| WO | 2011/132683 A1 | 10/2011 |
| WO | 2012/036482 A1 | 3/2012 |
| WO | 2012/067425 A1 | 5/2012 |
| WO | 2012/121561 A1 | 9/2012 |
| WO | 2012/141499 A1 | 10/2012 |
| WO | 2013/029659 A1 | 3/2013 |
| WO | 2013/187894 A1 | 12/2013 |

OTHER PUBLICATIONS

A. Kapturkiewicz: J. Herbich, J. Karpiuk, J. Nowacki; J.Phys. Chem. A 1997, 101, 2332-2344.

J. Herbich A. Kapturkiewicz, J. Nowacki; Chemical Physics Letters 262 (1996) 633-642 (Nov. 22, 1996).

Shi-Jian Su, Hisahiro Sasabe, Takashi Takeda, Junji Kido; Chem. Mater. 2008, 20; 1691-1693 (Feb. 12, 2008).

M. Rothmann S. Haneder, E. Da Como, C. Lennartz, C. Schildknecht, P. Strohriegl; Chem. Mater 2010, 22, 2403-2410 (Mar. 10, 2020).

Shi-Jian Su, Chao Cai, Junji Kido; Chem. Mater 2011, 23, 274-284 (Dec. 29, 2010).

D. Schneidenbach, S. Ammermann, M. Debeaux, A. Freund, M. Zollner, C. Daniliuc, P. Jones, W. Kowalsky, H. Johannes; Inorganic Chemistry, 2010, 49, 397-406, (Dec. 18, 2009).

K. Thomas, J. Lin, Y. Tao, C. Ko; J.Am. Chem. Soc. 2001 123, 9404-9411 (Aug. 28, 2001).

S. Gong, Y. Zhao, C. Yang, C. Zhong, J. Qin, D. Ma; J. Phys. Chem. C 2010, 114, 5193-5198 (Mar. 1, 2010).

S. Bonesi, R. Balsells; Journal of Luminescence 93 (2001) 51-74.

M. Baldo, M. Thompson, S. Forrest; Pure Appl. Chem., vol. 71, No. 11, 2095-2106 (1999).

V. Vaitkeviciene, A. Kruzinauskiene, S. Grigalevicius. J. Grazulevicius, R. Rutkaite, V. Jankauskas; Synthetic Metals, 158, 383-390 (2008).

E. Matsuda, M. Aoto, S. Takahashi, H. Ono, K. Tokumaru; Chemistry Letters, 1129-1132 (1992).

S. Wellinghoff, R. Hill, D. Naegeli, S. Lo, D. Rogers; Synthetic Metals, 41-43, (1991) 3203-3207.

H. Yersin, Highly Efficient OLEDs with Phosphorescent Materials, 207-208 (2008).

Third Party Submission dated Jul. 21, 2015 filed in U.S. Appl. No. 14/624,835.

Copending U.S. Appl. No. 14/624,835, filed Feb. 18, 2015, Hee-Choon Ahn et al.

Copending U.S. Appl. No. 14/624,921, filed Feb. 18, 2015, Soo Young Lee et al.

Petition for Inter Partes Review of U.S. Pat. No. 8,652,654, dated Feb. 23, 2015.

Petition for Inter Partes Review of U.S. Pat. No. 8,685,543, dated Feb. 23, 2015.

Order Dismissing Petitions for 1PR2015-00796 (against U.S. Pat. No. 8,685,543 B2) and 1PR2015-00797 (against U.S. Pat. No. 8,652,654 B2) dated Jun. 25, 2015.

Declaration of Benjamin J. Schwartz, Ph.D. Filed with Petition for Inter Partes Review of U.S. Pat. No. 8,685,543, dated Feb. 23, 2015.

Declaration of Benjamin J. Schwartz, Ph.D. Filed with Petition for Inter Partes Review of U.S. Pat. No. 8,652,654, dated Feb. 23, 2015.

Translation of Korean Tribunal re Invalidity of Korean Patent No. 10-0957288, dated Oct. 31, 2014, Filed with Petition for Inter Partes Review of U.S. Pat. No. 8,685,543, dated Feb. 23, 2015.

Zhang, K., et al., "Synthesis and properties of carbazole main chain copolymers with oxadiazole pendant toward bipolar polymer host: tuning the HOMO/LUMO level and triplet energy", Chemistry Materials, 2008, pp. 7324-7331, 20(23).

* cited by examiner

ORGANIC ELECTROLUMINESCENT COMPOUNDS, LAYERS AND ORGANIC ELECTROLUMINESCENT DEVICE USING THE SAME

CLAIM OF BENEFIT OF FILING DATE

The present application is a continuation-in-part of U.S. patent application Ser. No. 14/624,835 (filed Feb. 18, 2015), which is a continuation of U.S. patent application Ser. No. 14/004,089 (filed Nov. 25, 2013), which is a National application filing based upon PCT Application. No. PCT/KR12/01712 (filed Mar. 8, 2012), which claims the benefit of the filing date of Korean Patent Application No. 10-2011-0020492 (filed Mar. 8, 2011).

TECHNICAL FIELD

The present invention relates to novel combinations including organic electroluminescent compounds, and organic electroluminescent device using the same.

BACKGROUND

An electroluminescent (EL) device is a self-light-emitting device which has advantages over other types of display devices in that it provides a wider viewing angle, a greater contrast ratio, and has a faster response time. An organic EL device was first developed by Eastman Kodak, by using small molecules (aromatic diamines) and aluminum complexes in a light-emitting layer [Appl. Phys. Lett. 51, 913, 1987].

The most important factor to determine luminous efficiency in an organic EL device is a light-emitting materials. Until now, fluorescent materials have been widely used as light-emitting material. However, in view of electroluminescent mechanisms, phosphorescent materials theoretically show four (4) times higher luminous efficiency than fluorescent materials. Thus, recently, phosphorescent materials have been investigated.

Iridium(III) complexes have been widely known as phosphorescent material, including bis(2-(2'-benzothienyl)-pyridinato-N,C3')iridium(acetylacetonate) ((acac)Ir(btp)$_2$), tris (2-phenylpyridine)iridium (Ir(ppy)$_3$) and bis(4,6-difluorophenylpyridinato-N,C2)picolinate iridium (Firpic) as red, green and blue materials, respectively.

In order to improve color purity, luminous efficiency and stability, light-emitting materials can be used as one prepared by mixing a dopant with a host material. In the host material/dopant system, the host material has a great influence on the efficiency and performance of an EL device, and thus is important.

At present, 4,4'-N,N'-dicarbazol-biphenyl (CBP) is the most widely known host material for phosphorescent materials. Further, Pioneer (Japan) developed a high performance organic EL device employing, as a host material, bathocuproine (BCP) or aluminum(III)bis(2-methyl-8-quinolinate) (4-phenylphenolate) (BAlq) which had been a material used for a hole blocking layer.

Though these phosphorous host materials provide good light-emitting characteristics, they have the following disadvantages: (1) Due to their low glass transition temperature and poor thermal stability, their degradation may occur during a high-temperature deposition process in a vacuum. (2) The power efficiency of an organic EL device is given by [(π/voltage)×current efficiency], and thus the power efficiency is inversely proportional to the voltage. Though an organic EL device comprising phosphorescent materials provides better current efficiency (cd/A) than one comprising fluorescent materials, a significantly high driving voltage is required to be applied to an organic EL device, thereby resulting in poor power efficiency (lm/W). (3) Further, the operation lifetime of an organic EL device is short and luminous efficiency is still required to be improved.

International Patent Application Publication No. WO 2006/049013 discloses compounds for organic electroluminescent materials whose backbone has a condensed bicycle group. However, it does not disclose compounds having a nitrogen-containing condensed bicyclic group, which is formed by condensing two 6-membered rings; a carbazolic group; and an aryl or heteroaryl group. Further, an organic EL device comprising said compounds fails to provide good luminous efficiency, operation lifetime and driving voltage.

An object of the present invention is to provide organic electroluminescent compounds imparting excellent luminous efficiency, long operation lifetime and low driving voltage to a device; improved layer combinations using said compounds; and an organic electroluminescent device using said compounds (e.g., in the form of a layer that includes at least one of said compounds as a host material, and also includes a metal complex dopant, specifically an iridium metal complex dopant).

SUMMARY OF THE INVENTION

The present inventors found that the above object can be achieved by use of a unique combination of materials that are employed to provide an improved light emitting layer. Such layer may be disposed between an anode and a cathode. Thus, the layer may be such that an applied driving voltage causes electroluminescence by the layer. The layer may have therein (e.g., the layer may include or consist of) a host material and a metal complex (e.g., an iridium complex). The metal complex may be an iridium complex including an alkylated ligand. For instance it may be an iridium complex including an alkylated phenyl quinoline ligand. The alkyl group for the alkylated ligand may be a C1-C30 alkyl group. For example, it may be a C1 alkyl group, a C2 alkyl group, or any alkyl having a number of carbon atoms given by any other integer between 1 and 30. For a metal complex (e.g., an iridium complex) including an alkylated phenyl quinoline ligand, the alkylation may be of a phenyl moiety, a quinoline moiety or both.

Without limitation, an aspect of the invention may be described as a light emitting layer, including an organic electroluminescent compound as a host material in the layer; and
  an iridium complex dopant,
  wherein the organic electroluminescent compound is represented by the following Formula 1; and the iridium complex dopant is represented by the following Formula 2:

[Formula 1]

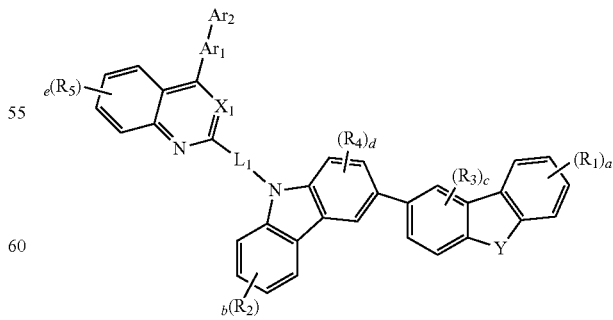

wherein:
L$_1$ represents a single bond;
X$_1$ represents N;
Y represents —NR$_{13}$—;

$Ar_1$ represents a single bond, a substituted or unsubstituted 5- to 30-membered heteroarylene group, a substituted or unsubstituted (C6-C30)arylene group;

$Ar_2$ represents hydrogen, deuterium, a substituted or unsubstituted (C1-C30)alkyl group, a substituted or unsubstituted (C6-C30)aryl group, or a substituted or unsubstituted 5- to 30-membered heteroaryl group;

$R_1$ to $R_5$ each independently represent hydrogen, deuterium, a halogen, a substituted or unsubstituted (C1-C30)alkyl group, a substituted or unsubstituted (C6-C30)aryl group, a substituted or unsubstituted 5- to 30-membered heteroaryl group, a substituted or unsubstituted (C3-C30)cycloalkyl group, a substituted or unsubstituted 5- to 7-membered heterocycloalkyl group, a substituted or unsubstituted (C6-C30)aryl(C1-C30)alkyl group, a substituted or unsubstituted (C6-C30)aryl group fused with at least one (C3-C30)cycloalkyl group, a 5- or 7-membered heterocycloalkyl group fused with at least one substituted or unsubstituted (C6-C30)aromatic ring, (C3-C30)cycloalkyl group fused with at least one substituted or unsubstituted (C6-C30)aromatic ring, —$NR_{14}R_{15}$, —$SiR_{16}R_{17}R_{18}$, —$SR_{19}$, —$OR_{20}$, a substituted or unsubstituted (C2-C30)alkenyl group, a substituted or unsubstituted (C2-C30)alkynyl group, a cyano group, a nitro group, or a hydroxyl group; or are linked to an adjacent substituent via a substituted or unsubstituted (C3-C30)alkylene group or a substituted or unsubstituted (C3-C30)alkenylene group to form a mono- or polycyclic alicyclic ring or a mono- or polycyclic aromatic ring whose carbon atom(s) may be substituted by at least one hetero atom selected from nitrogen, oxygen and sulfur;

$R_{13}$ to $R_{20}$ have the same meaning as one of $R_1$ to $R_5$, a, b and e each independently represent an integer of 1 to 4; where a, b or e is an integer of 2 or more, each of $R_1$, each of $R_2$ or each of $R_5$ is the same or different;

c and d each independently represent an integer of 1 to 3; where c or d is an integer of 2 or more, each of $R_3$ or each of $R_4$ is the same or different; and the heterocycloalkyl group and the heteroaryl(ene) group contain at least one hetero atom selected from B, N, O, S, P(=O), Si and P, and $$M^1 L^{101} L^{102} L^{103} \quad \text{[Formula 2]}$$

wherein
$M^1$ is Ir;
$L^{101}$ and $L^{102}$ are the same and represent

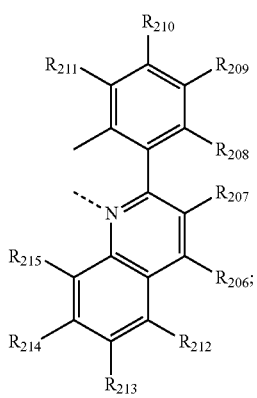

and
$L^{103}$ represents

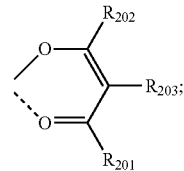

wherein $R_{201}$ to $R_{203}$ each independently represent hydrogen, deuterium, or a (C1-C30)alkyl group;

$R_{206}$ to $R_{208}$, $R_{210}$, and $R_{212}$ to $R_{215}$ each independently represent hydrogen, deuterium, a substituted or unsubstituted (C1-C30)alkyl group, or a substituted or unsubstituted (C6-C30)aryl group; and $R_{209}$ and $R_{211}$ each independently represent a substituted or unsubstituted (C1-C30)alkyl group.

DETAILED DESCRIPTION

With attention now to the general teachings herein, there are envisioned combinations of an organic electroluminescent host material and a complex dopant to form a light emitting layer.

The host material may be a compound represented by the following formula 1:

[Formula 1]

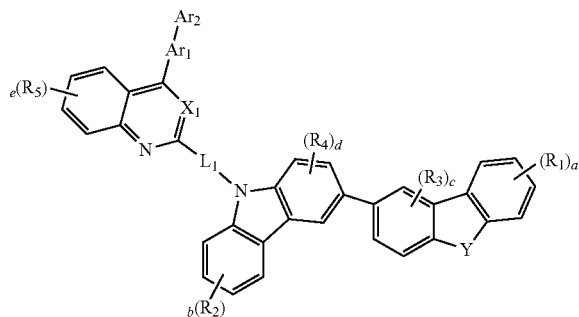

wherein
$L_1$ represents a single bond, a substituted or unsubstituted 5- to 30-membered heteroarylene group, a substituted or unsubstituted (C6-C30)arylene group, or a substituted or unsubstituted (C6-C30)cycloalkylene group;

$X_1$ represents CH or N;

Y represents —O—, —S—, —$CR_{11}R_{12}$— or —$NR_{13}$—;

$Ar_1$ represents a single bond, a substituted or unsubstituted 5- to 30-membered heteroarylene group, a substituted or unsubstituted (C6-C30)arylene group, or a substituted or unsubstituted (C1-C30)alkylene group;

$Ar_2$ represents hydrogen, deuterium, a substituted or unsubstituted (C1-C30)alkyl group, a substituted or unsubstituted (C6-C30)aryl group, or a substituted or unsubstituted 5- to 30-membered heteroaryl group;

$R_1$ to $R_5$ each independently represent hydrogen, deuterium, a halogen, a substituted or unsubstituted (C1-C30)alkyl group, a substituted or unsubstituted (C6-C30)aryl group, a substituted or unsubstituted 5- to 30-membered heteroaryl group, a substituted or unsubstituted (C3-C30)cycloalkyl group, a substituted or unsubstituted 5- to 7-membered heterocycloalkyl group, a substituted or unsubstituted (C6-C30) aryl(C1-C30)alkyl group, a substituted or unsubstituted (C6-C30)aryl group fused with at least one (C3-C30)cycloalkyl group, a 5- or 7-membered heterocycloalkyl group fused with at least one substituted or unsubstituted (C6-C30)aromatic ring, (C3-C30)cycloalkyl group fused with at least one substituted or unsubstituted (C6-C30)aromatic ring, $-NR_{14}R_{15}$, $-SiR_{16}R_{17}R_{18}$, $-SR_{19}$, $-OR_{20}$, a substituted or unsubstituted (C2-C30)alkenyl group, a substituted or unsubstituted (C2-C30)alkynyl group, a cyano group, a nitro group, or a hydroxyl group; or are linked to an adjacent substituent via a substituted or unsubstituted (C3-C30)alkylene group or a substituted or unsubstituted (C3-C30)alkenylene group to form a mono- or polycyclic alicyclic ring or a mono- or polycyclic aromatic ring whose carbon atom(s) may be substituted by at least one hetero atom selected from nitrogen, oxygen and sulfur;

$R_{11}$ to $R_{20}$ have the same meaning as one of $R_1$ to $R_5$ (or in the case in which Y represents $NR_{13}$, then $R_{13}$ to $R_{20}$ have the same meaning as one of $R_1$ to $R_5$);

a, b and e each independently represent an integer of 1 to 4; where a, b or e is an integer of 2 or more, each of $R_1$, each of $R_2$ or each of $R_5$ is the same or different;

c and d each independently represent an integer of 1 to 3; where c or d is an integer of 2 or more, each of $R_3$ or each of $R_4$ is the same or different; and the heterocycloalkyl group and the heteroaryl(ene) group contain at least one hetero atom selected from B, N, O, S, P(=O), Si and P, Herein, "(C1-C30)alkyl(ene)" is a linear or branched alkyl (ene) having 1 to 30, preferably 1 to 20, more preferable 1 to 10 carbon atoms and includes methyl, ethyl, n-propyl, isopropyl, n-butyl, isobutyl, tert-butyl, etc.; "(C2-C30) alkenyl (ene)" is a linear or branched alkenyl(ene) having 2 to 30, preferably 2 to 20, more preferably 1 to 10 carbon atoms and includes vinyl, 1-propenyl, 2-propenyl, 1-butenyl, 2-butenyl, 3-butenyl, 2-methylbut-2-enyl, etc.; "(C2-C30)alkynyl" is a linear or branched alkynyl having 2 to 30, preferably 2 to 20, more preferably 1 to 10 carbon atoms and includes ethynyl, 1-propynyl, 2-propynyl, 1-butynyl, 2-butynyl, 3-butynyl, 1-methylpent-2-ynyl, etc.; "(C1-C30)alkoxy" is a linear or branched alkoxy having 1 to 30, preferably 2 to 20, more preferably 2 to 10 carbon atoms and includes methoxy, ethoxy, propoxy, isopropoxy, 1-ethylpropoxy, etc.; "(C3-C30)cycloalkyl" is a mono- or polycyclic hydrocarbon having 3 to 30, preferably 3 to 20, more preferably 3 to 7 carbon atoms and includes cyclopropyl, cyclobutyl, cyclopentyl, cyclohexyl, etc.; "(C6-C30)cycloalkylene" is one formed by removing hydrogen from cycloalkyl having 6 to 30, preferably 6 to 20, more preferably 6 or 7 carbon atoms; and "5- to 7-membered heterocycloalkyl" is a cycloalkyl having at least one hetero atom selected from B, N, O, S, P(=O), Si and P, preferably N, O and S, and carbon atoms as remaining ring backbone atoms other than said hetero atom and includes tetrahydrofuran, pyrrolidine, tetrahydropyran, etc. Further, "(C6-C30)aryl(ene)" is a monocyclic ring or fused ring derived from an aromatic hydrocarbon and having preferably 6 to 20 ring backbone carbon atoms; and includes phenyl, biphenyl, terphenyl, naphthyl, fluorenyl, phenanthrenyl, anthracenyl, indenyl, triphenylenyl, pyrenyl, tetracenyl, perylenyl, chrysenyl, naphthacenyl, fluoranthenyl, etc. Further, "5- or 30-membered heteroaryl(ene)" is an aryl having at least one, preferably 1 to 4 hetero atom selected from the group consisting of B, N, O, S, P(=O), Si and P, and carbon atoms as remaining ring backbone atoms other than said hetero atom; is a monocyclic ring or fused ring condensed with at least benzene ring; has preferably 5 to 21 ring backbone atoms; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc. and a fused ring-type heteroaryl including benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc.

Preferably, substituents of formula 1 are as follows:

$L_1$ represents preferably a single bond, a substituted or unsubstituted 5- or 30-membered heteroarylene group or a substituted or unsubstituted (C6-C30)arylene group, more preferably a single bond or a substituted or unsubstituted (C6-C30)arylene group.

X represents preferably N.

Y represents preferably $-O-$, $-S-$, $-CR_{11}R_{12}-$ (wherein $R_{11}$ and $R_{12}$ each independently represent a substituted or unsubstituted (C1-C30)alkyl group) or $-NR_{13}-$ (wherein $R_{13}$ represents a halogen, deuterium, a substituted or unsubstituted (C6-C30)aryl group, or a substituted or unsubstituted 5- or 30-membered heteroaryl group).

$R_1$ and $R_2$ each independently represent hydrogen, a substituted or unsubstituted (C6-C30)aryl group, a substituted or unsubstituted 5- or 30-membered heteroaryl group, $-NR_{14}R_{15}$ (wherein $R_{14}$ and $R_{15}$ each independently represent a substituted or unsubstituted (C1-C30)alkyl group or a substituted or unsubstituted (C6-C30)aryl group) or a hydroxyl group, more preferably hydrogen or a substituted or unsubstituted (C6-C30)aryl group.

$R_1$ to $R_5$ each independently represent hydrogen or a substituted or unsubstituted (C1-C30)alkyl group, more preferably hydrogen.

a to e each independently represent an integer of 1.

*—$Ar_1$—$Ar_2$ is selected from the following structures:

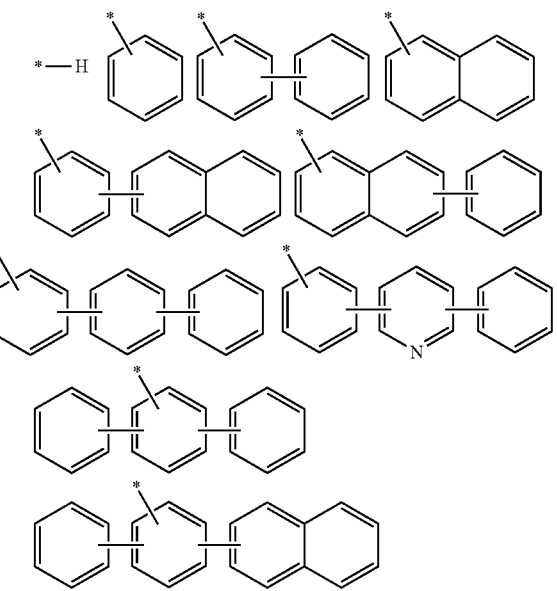

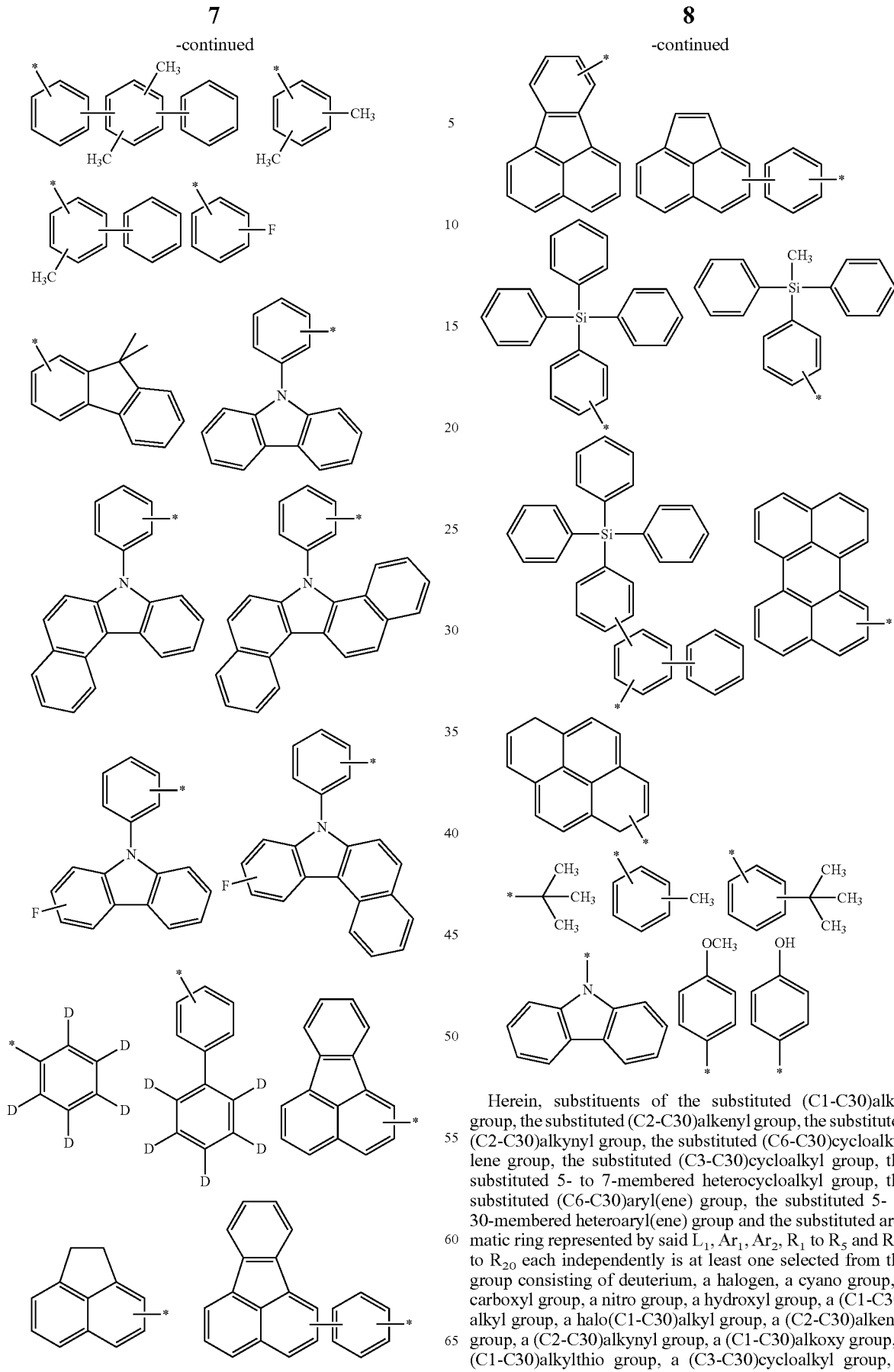

Herein, substituents of the substituted (C1-C30)alkyl group, the substituted (C2-C30)alkenyl group, the substituted (C2-C30)alkynyl group, the substituted (C6-C30)cycloalkylene group, the substituted (C3-C30)cycloalkyl group, the substituted 5- to 7-membered heterocycloalkyl group, the substituted (C6-C30)aryl(ene) group, the substituted 5- to 30-membered heteroaryl(ene) group and the substituted aromatic ring represented by said $L_1$, $Ar_1$, $Ar_2$, $R_1$ to $R_5$ and $R_{11}$ to $R_{20}$ each independently is at least one selected from the group consisting of deuterium, a halogen, a cyano group, a carboxyl group, a nitro group, a hydroxyl group, a (C1-C30) alkyl group, a halo(C1-C30)alkyl group, a (C2-C30)alkenyl group, a (C2-C30)alkynyl group, a (C1-C30)alkoxy group, a (C1-C30)alkylthio group, a (C3-C30)cycloalkyl group, a (C3-C30)cycloalkenyl group, a 5- to 7-membered heterocycloalkyl group, a (C6-C30)aryl group, a (C6-C30)aryloxy group, a (C6-C30)arylthio group, a 5- to 30-membered heteroaryl group, a 5- to 30-membered heteroaryl group substituted by a (C6-C30)aryl group, a (C6-C30)aryl group substituted by a 5- to 30-membered heteroaryl group, a tri(C1-C30) alkylsilyl group, a tri(C6-C30)arylsilyl group, a di(C1-C30) alkyl(C6-C30)arylsilyl group, a (C1-C30)alkyldi(C6-C30) arylsilyl group, an amino group, a mono or di(C1-C30) alkylamino group, a mono or di(C6-C30)arylamino group, a (C1-C30)alkyl(C6-C30)arylamino group, a (C1-C30)alkylcarbonyl group, a (C1-C30)alkoxycarbonyl group, a (C1-C30)arylcarbonyl group, a di(C6-C30)arylbornyl group, a di(C1-C30)alkylbornyl group, a (C1-C30)alkyl(C6-C30)arylbornyl group, a (C6-C30)aryl(C1-C30)alkyl group and a (C1-C30)alkyl(C6-C30)aryl group. Preferably, said substituents are at least one selected from the group consisting of deuterium, a halogen, a (C1-C30)alkyl group, a halo(C1-C30)alkyl group, a (C6-C30)aryl group, a 5- to 30-membered heteroaryl group, a tri(C1-C30)alkylsilyl group, a tri(C6-C30)arylsilyl group, a di(C1-C30)alkyl(C6-C30)arylsilyl group, a (C1-C30)alkyldi(C6-C30)arylsilyl group, a hydroxyl group and a (C1-C30)alkoxy group.

By way of more particular illustration, one preferred representation of Formula 1 is the following:

[Formula 1]

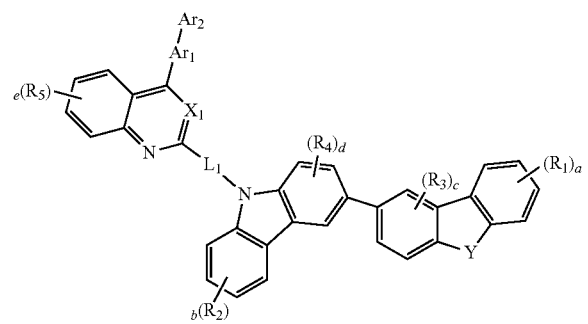

wherein:
$L_1$ represents a single bond;
$X_1$ represents N;
Y represents $-NR_{13}-$;
$Ar_1$ represents a single bond, a substituted or unsubstituted 5- to 30-membered heteroarylene group, a substituted or unsubstituted (C6-C30)arylene group;
$Ar_2$ represents hydrogen, deuterium, a substituted or unsubstituted (C1-C30)alkyl group, a substituted or unsubstituted (C6-C30)aryl group, or a substituted or unsubstituted 5- to 30-membered heteroaryl group;
$R_1$ to $R_5$ each independently represent hydrogen, deuterium, a halogen, a substituted or unsubstituted (C1-C30)alkyl group, a substituted or unsubstituted (C6-C30)aryl group, a substituted or unsubstituted 5- to 30-membered heteroaryl group, a substituted or unsubstituted (C3-C30)cycloalkyl group, a substituted or unsubstituted 5- to 7-membered heterocycloalkyl group, a substituted or unsubstituted (C6-C30) aryl(C1-C30)alkyl group, a substituted or unsubstituted (C6-C30)aryl group fused with at least one (C3-C30)cycloalkyl group, a 5- or 7-membered heterocycloalkyl group fused with at least one substituted or unsubstituted (C6-C30)aromatic ring, (C3-C30)cycloalkyl group fused with at least one substituted or unsubstituted (C6-C30)aromatic ring, $-NR_{14}R_{15}$, $-SiR_{16}R_{17}R_{18}$, $-SR_{19}$, $-OR_{20}$, a substituted or unsubstituted (C2-C30)alkenyl group, a substituted or unsubstituted (C2-C30)alkynyl group, a cyano group, a nitro group, or a hydroxyl group; or are linked to an adjacent substituent via a substituted or unsubstituted (C3-C30)alkylene group or a substituted or unsubstituted (C3-C30)alkenylene group to form a mono- or polycyclic alicyclic ring or a mono- or polycyclic aromatic ring whose carbon atom(s) may be substituted by at least one hetero atom selected from nitrogen, oxygen and sulfur;

$R_{11}$ to $R_{20}$ have the same meaning as one of $R_1$ to $R_5$,
a, b and e each independently represent an integer of 1 to 4; where a, b or e is an integer of 2 or more, each of $R_1$, each of $R_2$ or each of $R_5$ is the same or different;
c and d each independently represent an integer of 1 to 3; where c or d is an integer of 2 or more, each of $R_3$ or each of $R_4$ is the same or different; and
the heterocycloalkyl group and the heteroaryl(ene) group contain at least one hetero atom selected from B, N, O, S, P(=O), Si and P.

With more particularity, $R_1$ to $R_5$ may each independently represent hydrogen or a substituted or unsubstituted (C6-C30)aryl group. By way of illustration, either or both of $R_3$ or $R_4$ may represent a substituted or unsubstituted (C6-C30)aryl group.

With more particularity, $R_{13}$ my be a substituted or unsubstituted (C1-C30)alkyl group, a substituted or unsubstituted (C6-C30)aryl group, a substituted or unsubstituted 5- to 30-membered heteroaryl group, a substituted or unsubstituted (C6-C30)aryl group fused with at least one (C3-C30) cycloalkyl group, a 5- or 7-membered heterocycloalkyl group fused with at least one substituted or unsubstituted (C6-C30) aromatic ring, or a (C3-C30)cycloalkyl group fused with at least one substituted or unsubstituted (C6-C30)aromatic ring. For instance, $R_{13}$ may be a substituted or unsubstituted (C1-C30)alkyl group, a substituted or unsubstituted (C6-C30)aryl group, or a substituted or unsubstituted 5- to 30-membered heteroaryl group. One particularly preferred approach contemplates that $R_{13}$ is substituted or unsubstituted (C6-C30) aryl group.

Organic electroluminescent compounds according to the present invention include the following, but are not limited thereto:

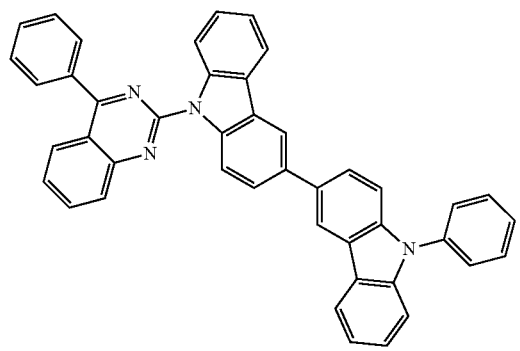

C-1

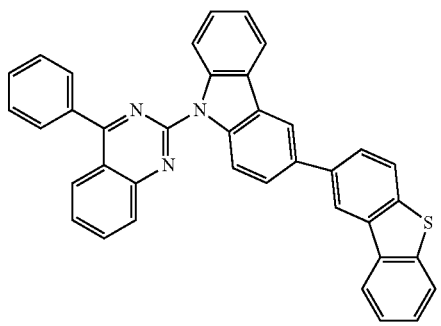

C-2

-continued
C-3
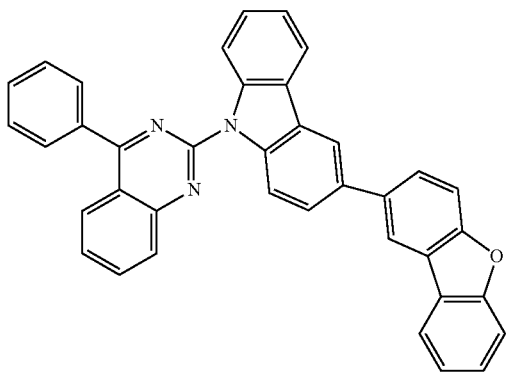
C-4
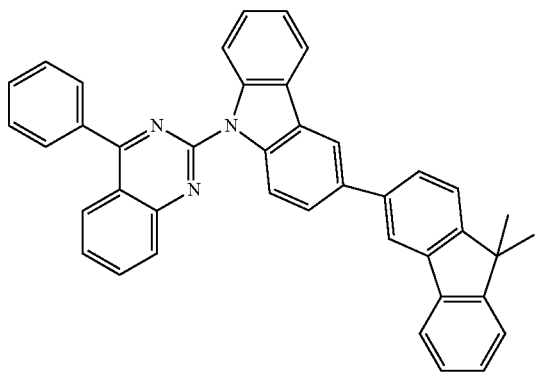
C-5
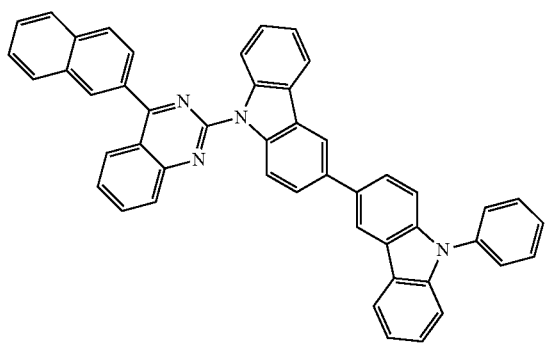
C-6
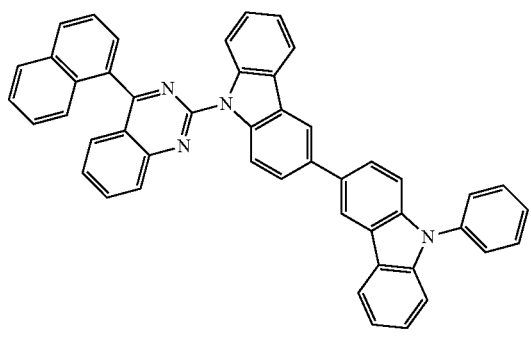
C-7
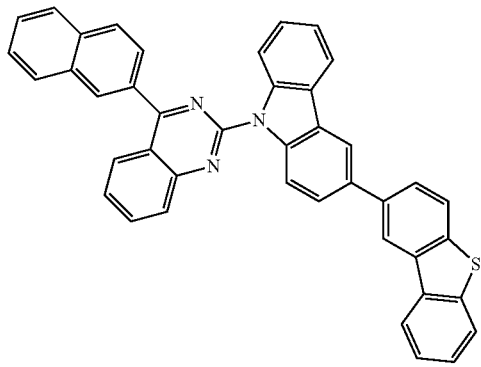
C-8
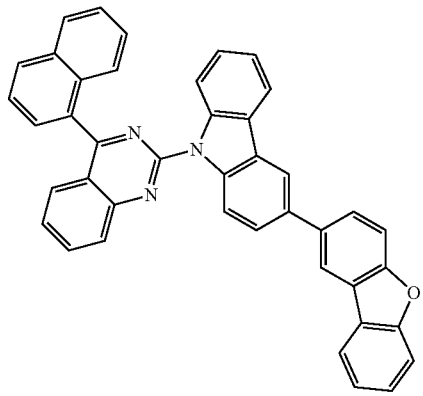
C-9
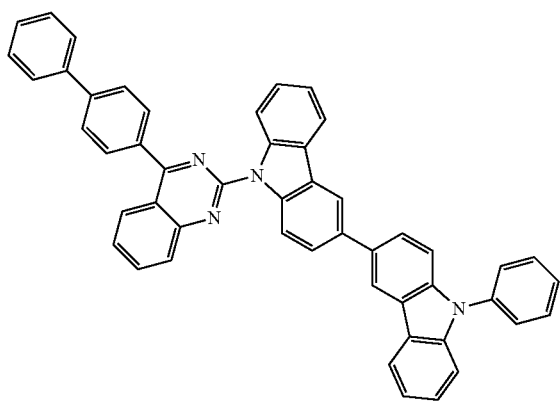
C-10
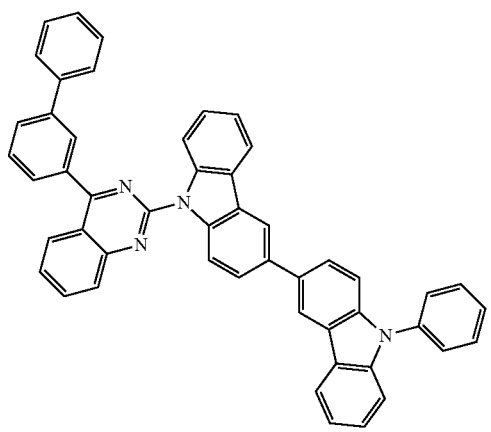

-continued
C-11
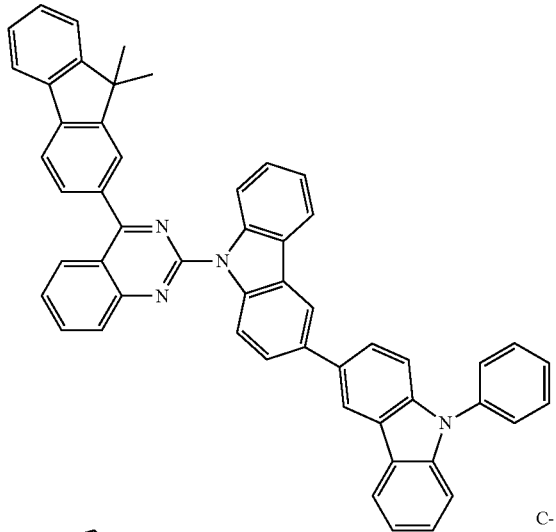
C-12
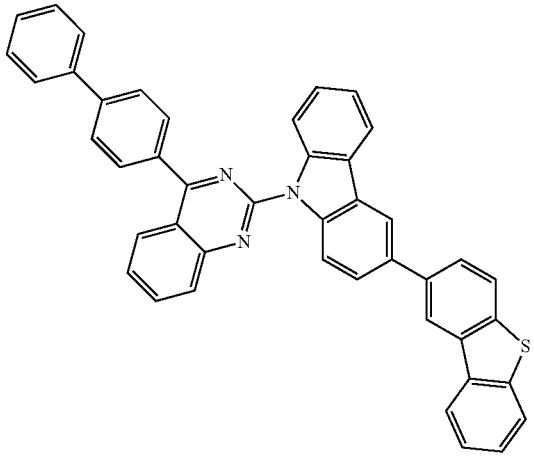
C-13
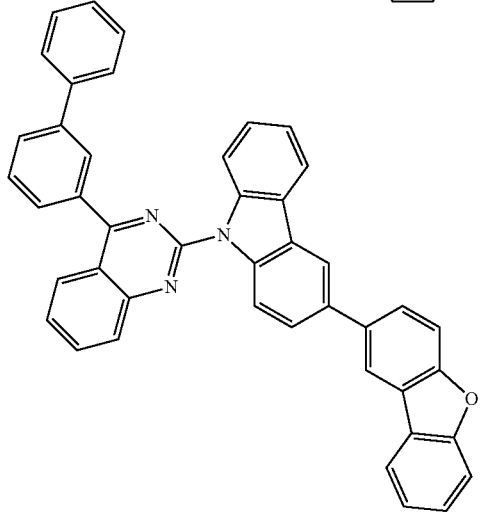
C-14
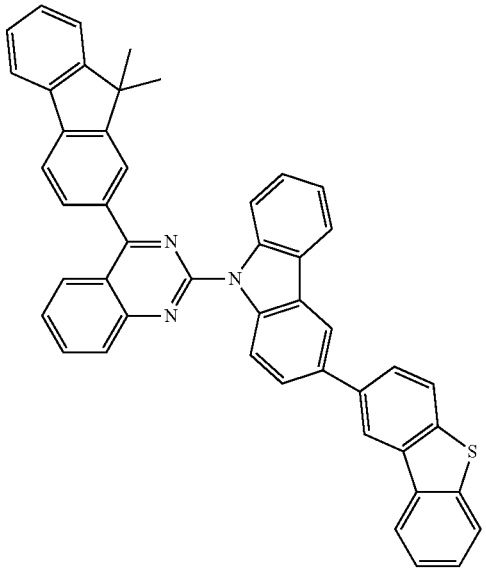
C-15
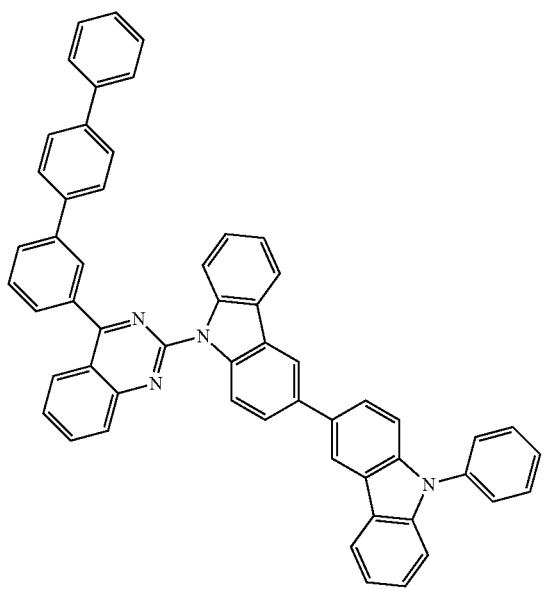
C-16
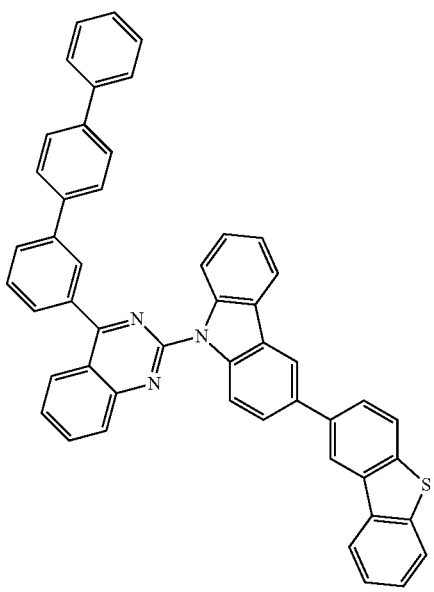

-continued
C-17
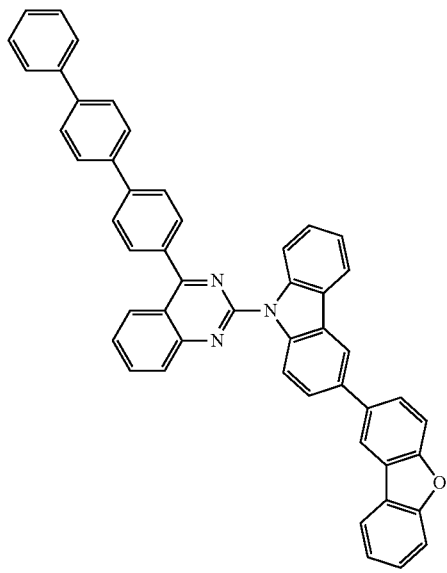
C-18
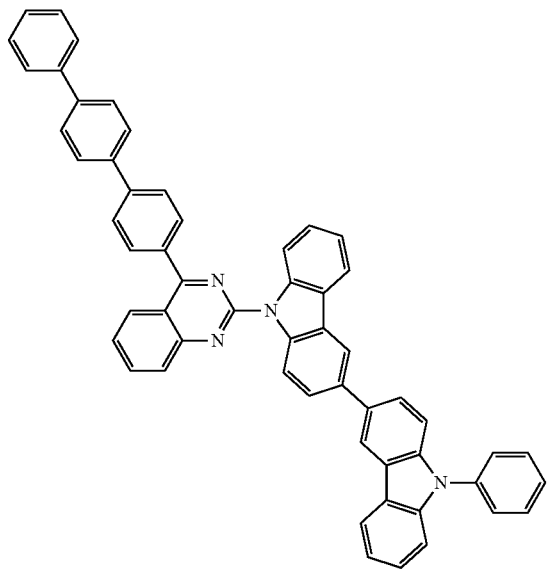
C-19
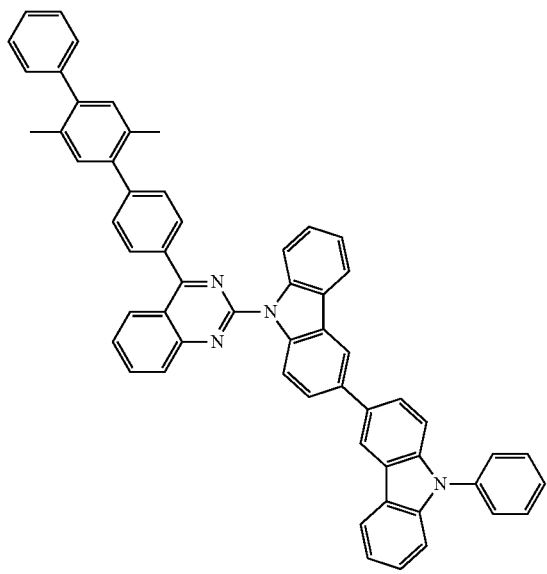
C-20
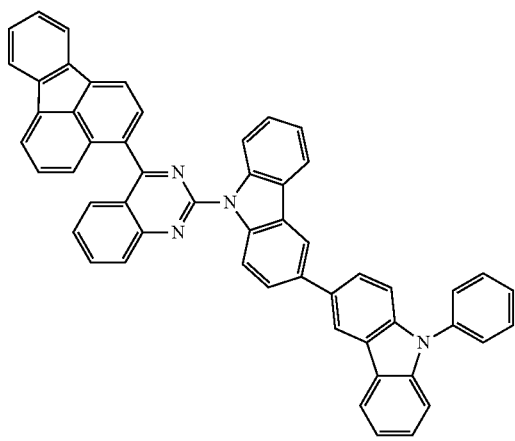
C-21
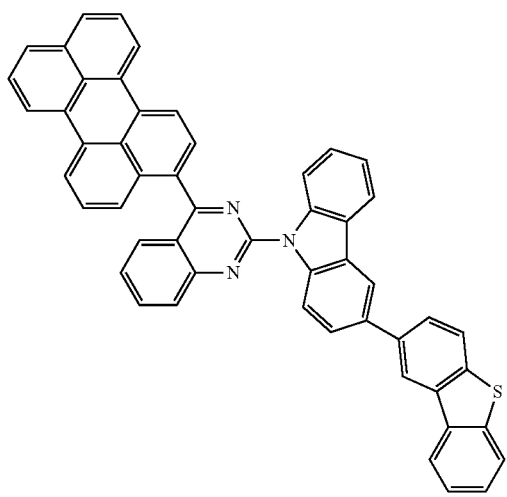
C-22
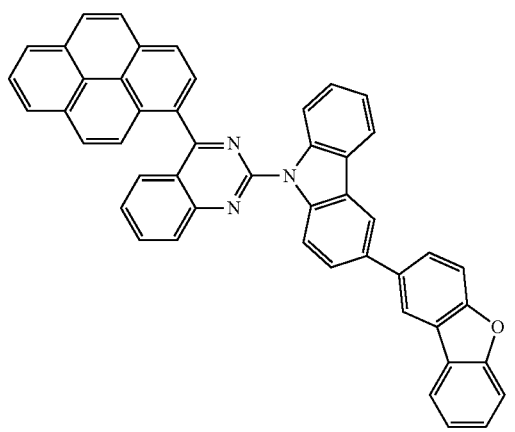

-continued
C-23
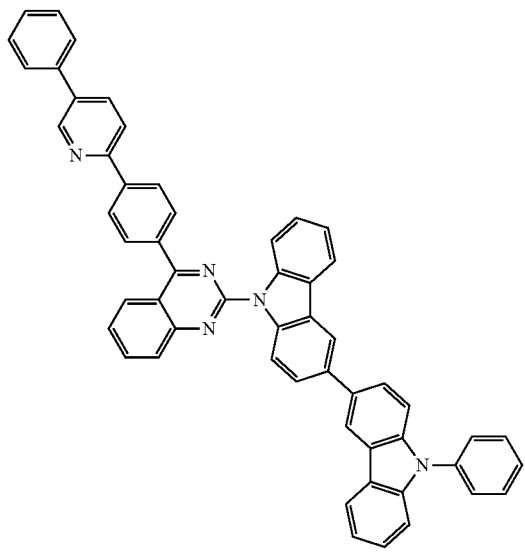
C-24
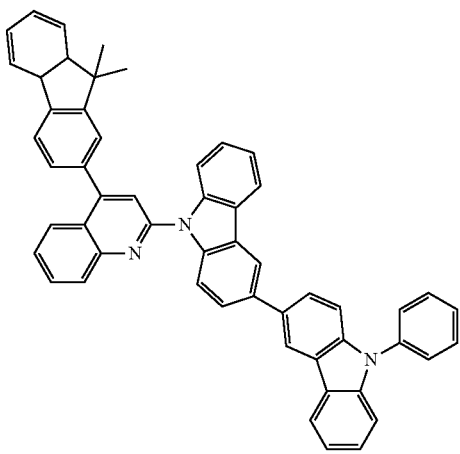
C-25
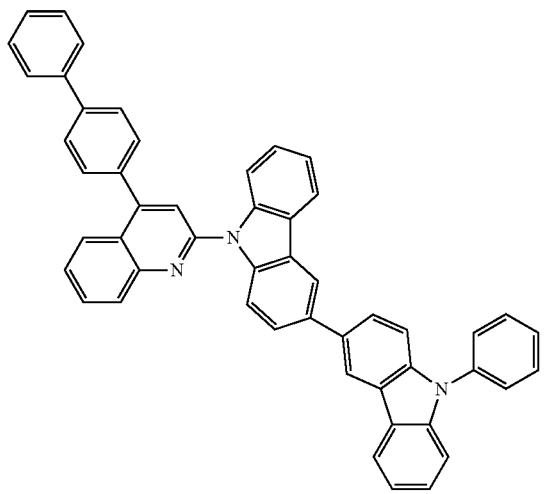
C-26
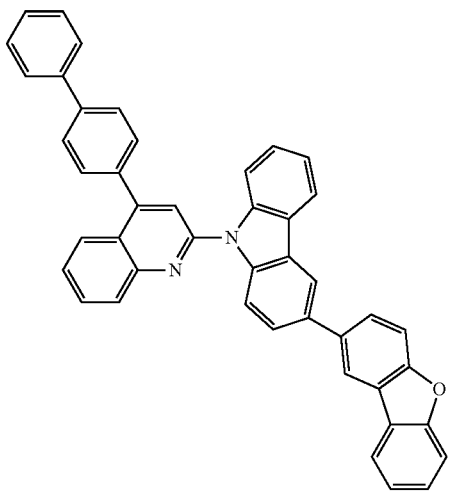
C-27
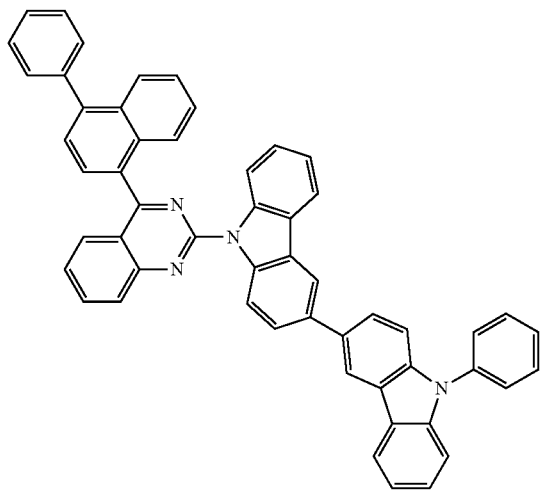
C-28
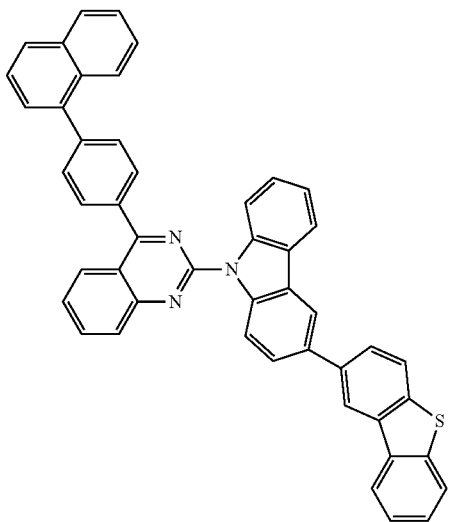

-continued
C-29
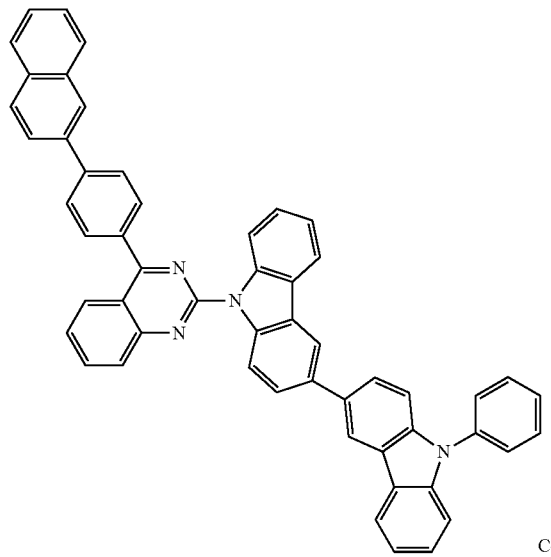
C-30
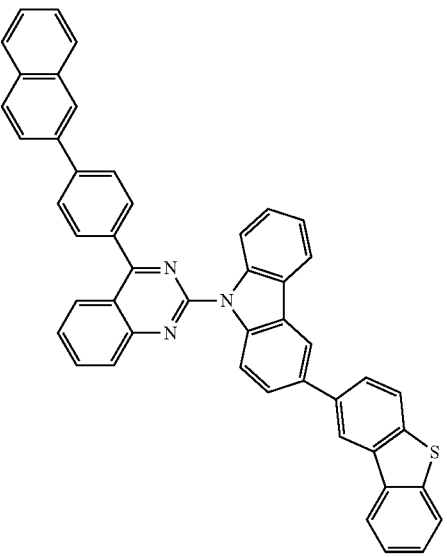
C-31
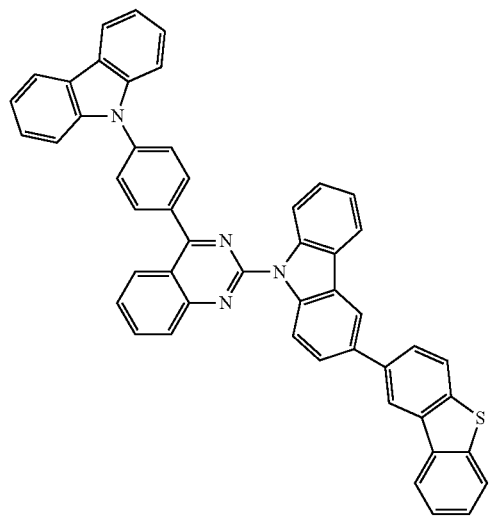
C-32
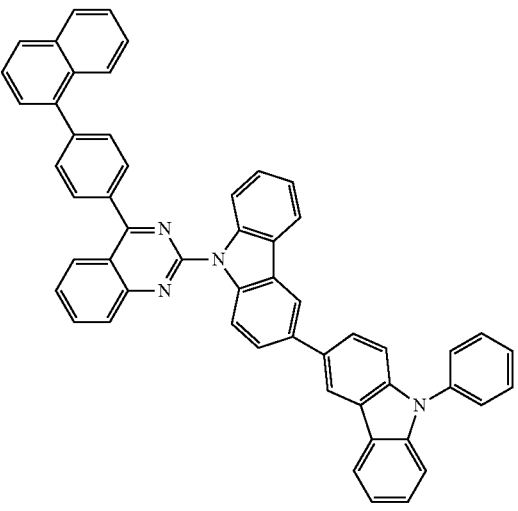
C-33
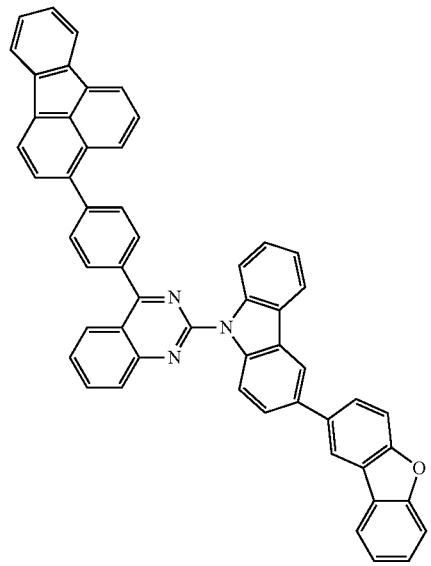
C-34
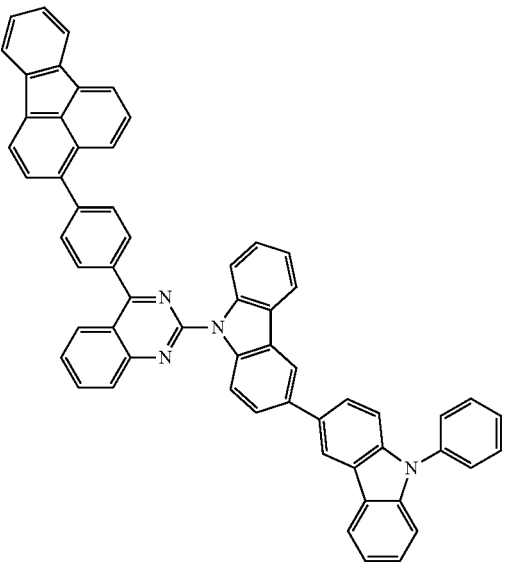

-continued
C-35
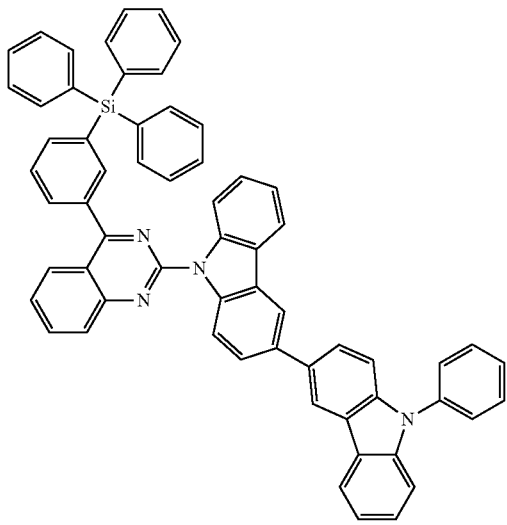
C-36
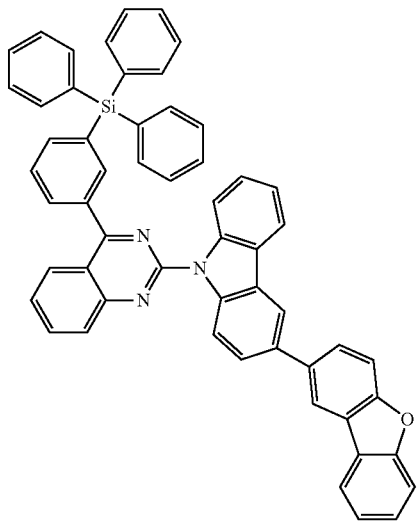
C-37
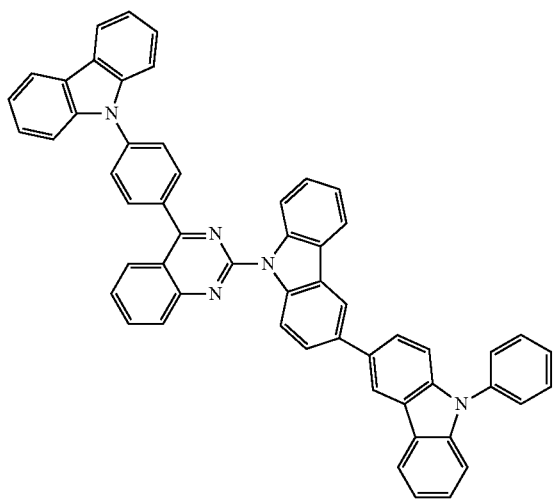
C-38
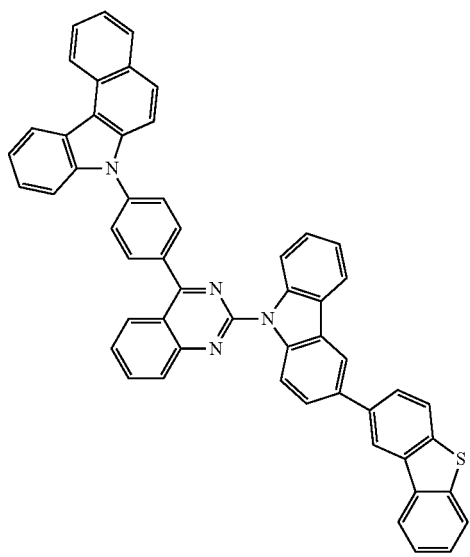
C-39
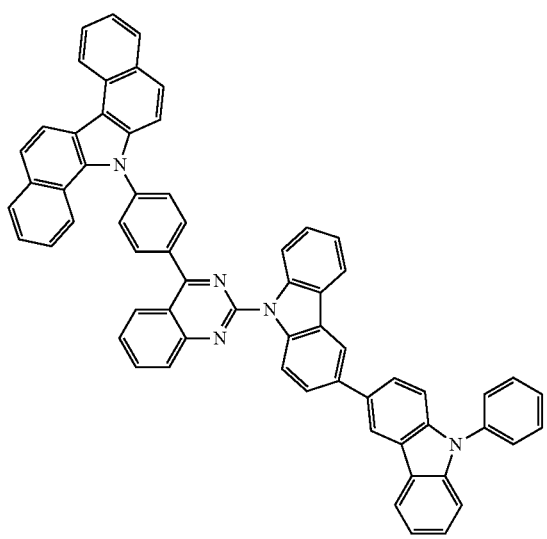
C-40
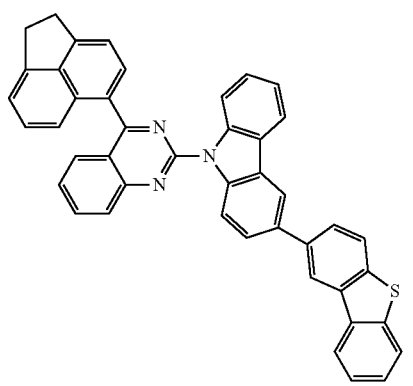

-continued
C-41
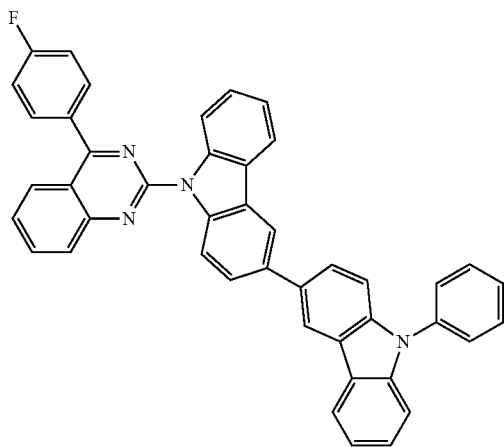
C-42
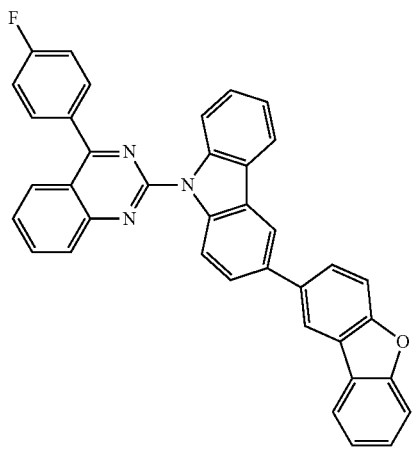
C-43
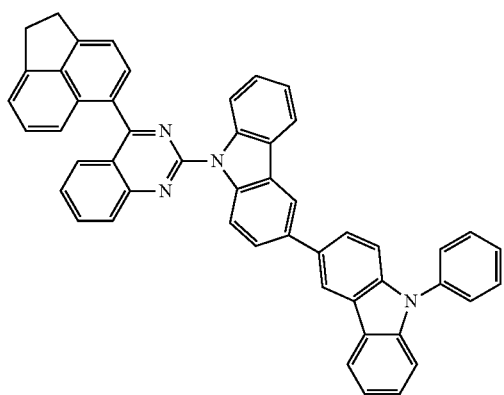
C-44
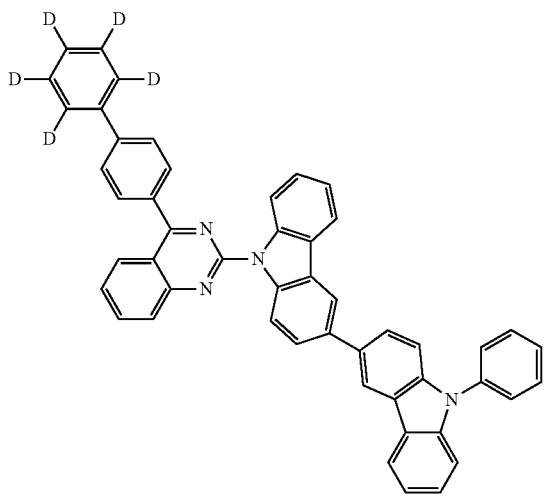
C-45
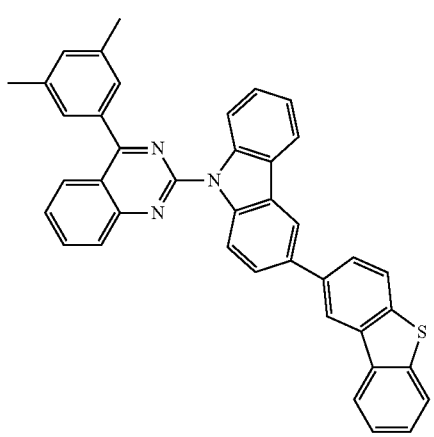
C-46
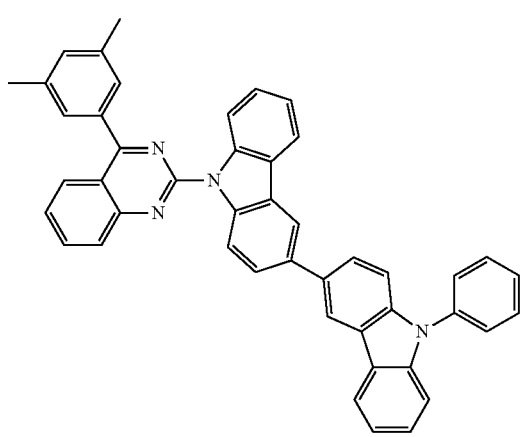

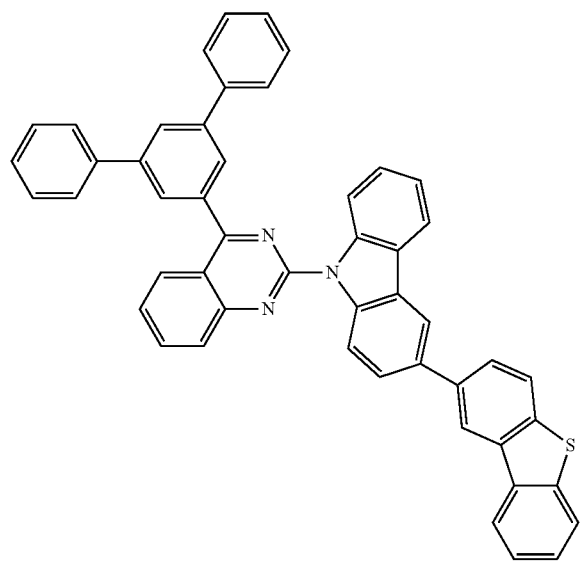
C-47
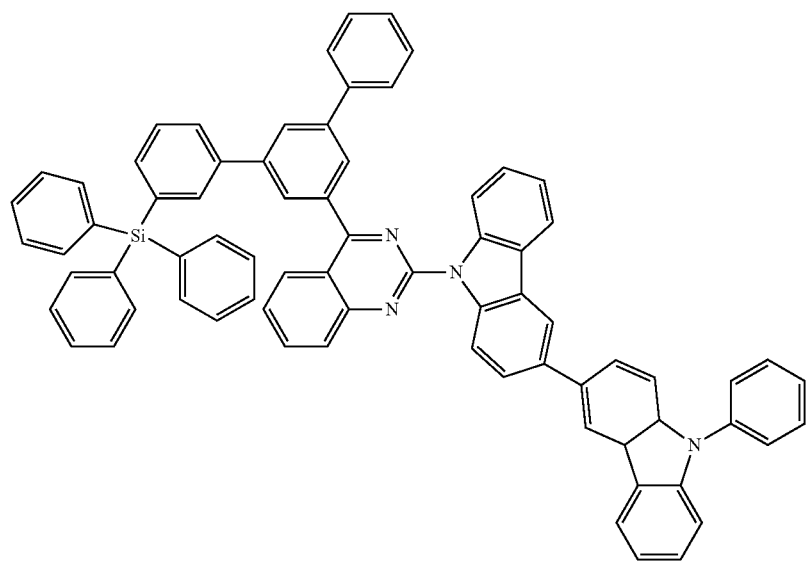
C-48

-continued
C-49
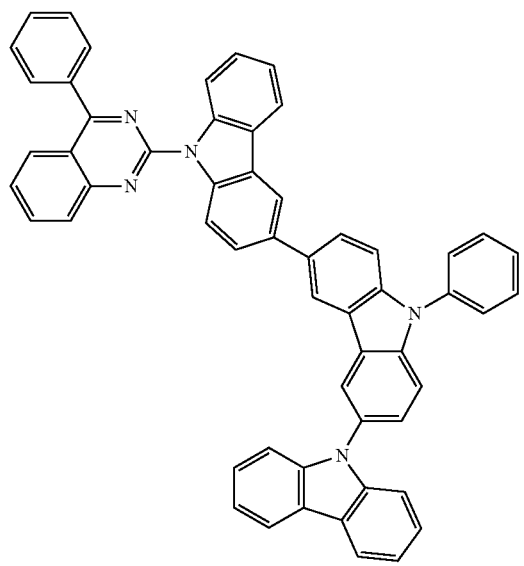
C-50
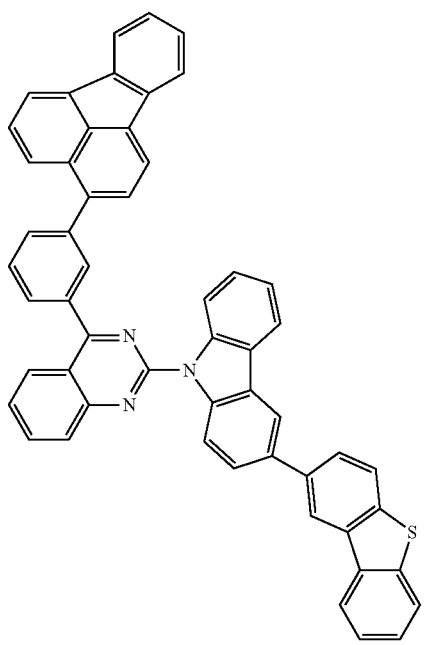
C-51
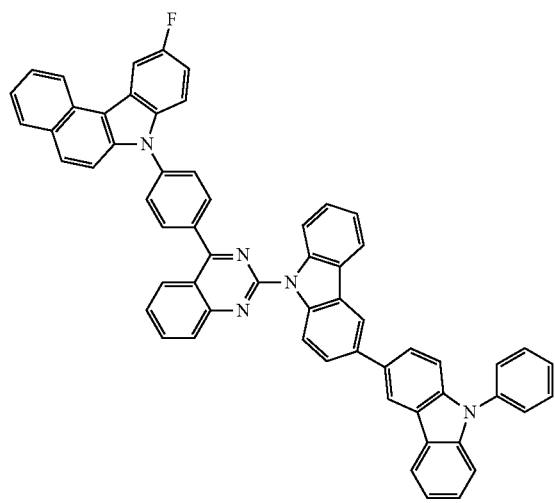
C-52
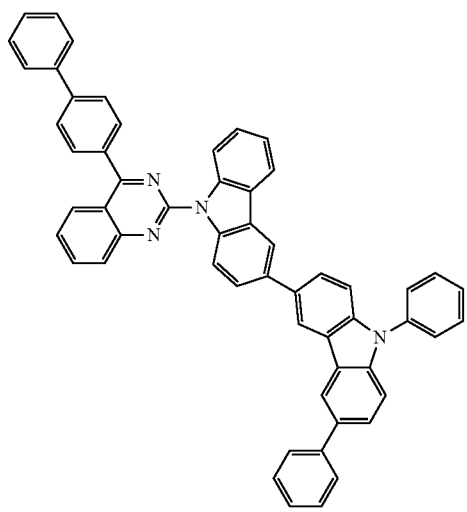
C-53
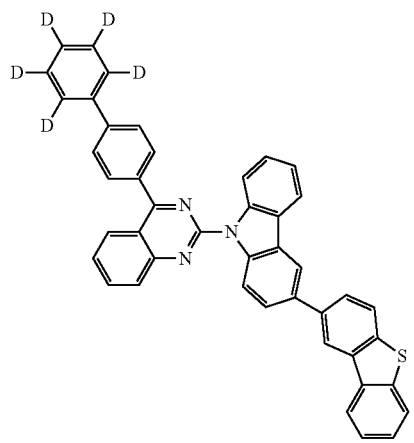
C-54
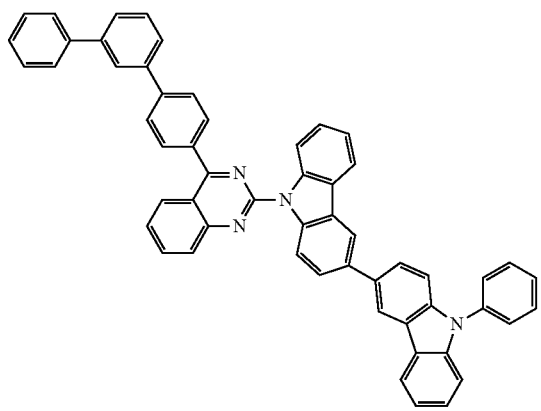

-continued
C-55
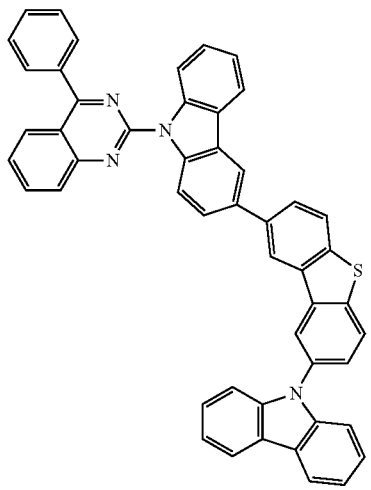
C-56
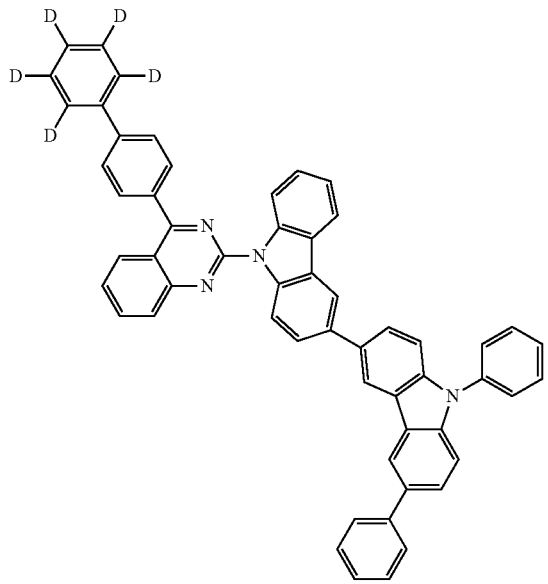
C-57
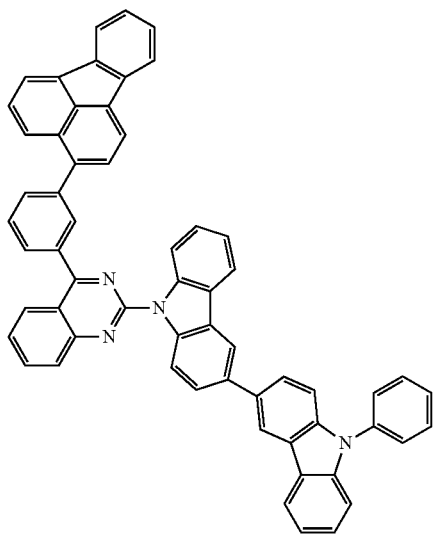
C-58
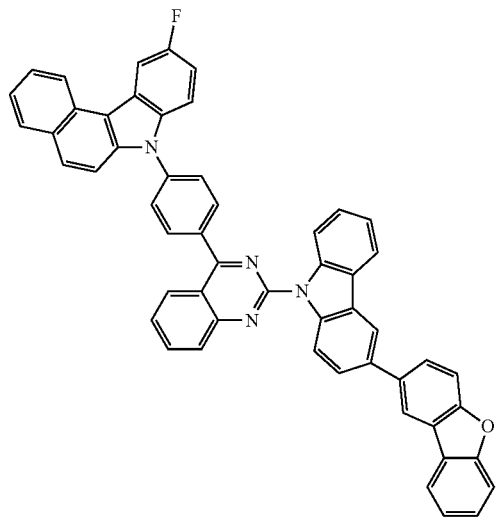
C-59
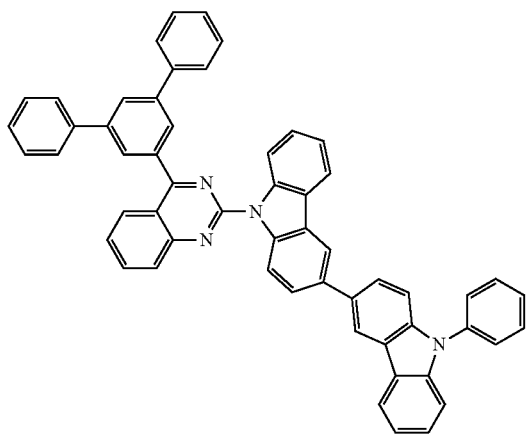
C-60
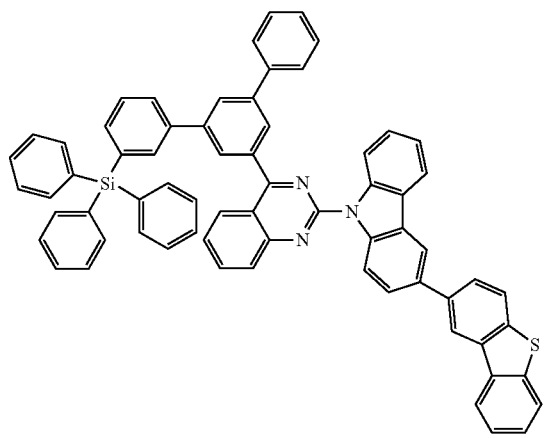

C-61
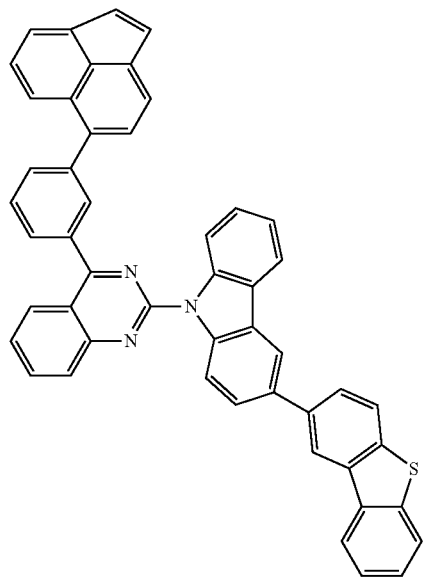
C-62
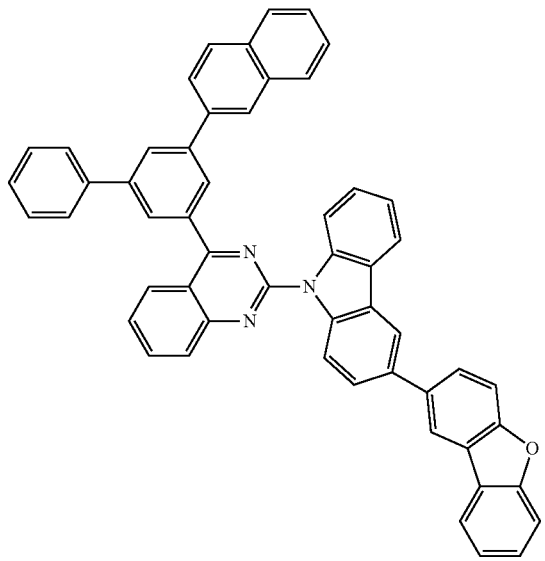
C-63
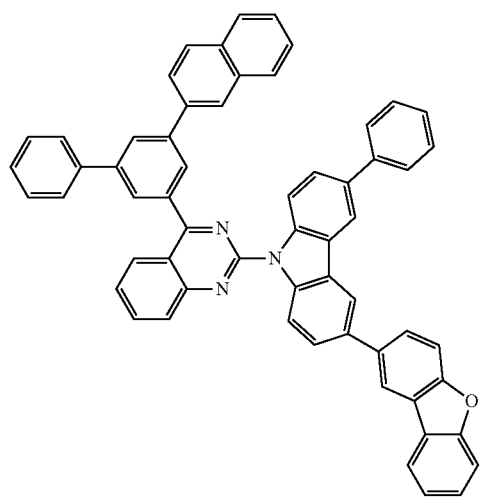
C-64
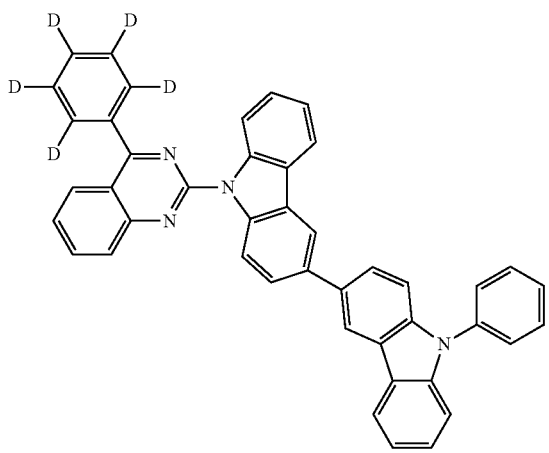

-continued
C-65
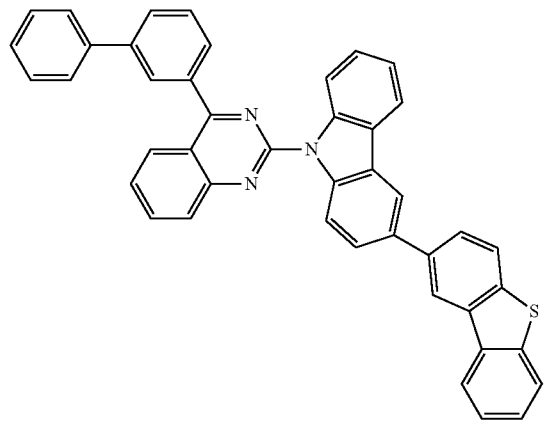
C-66
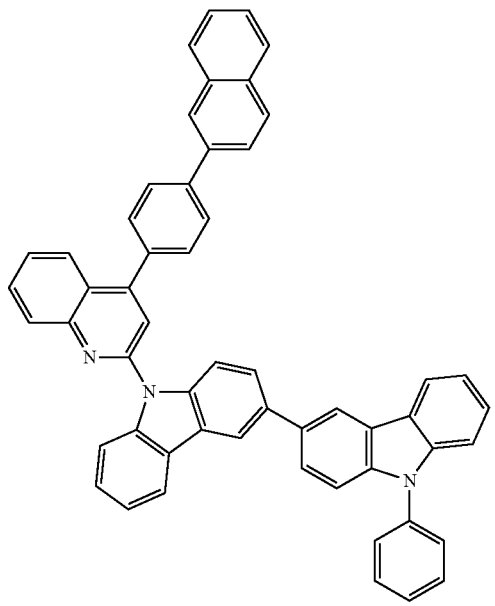
C-67
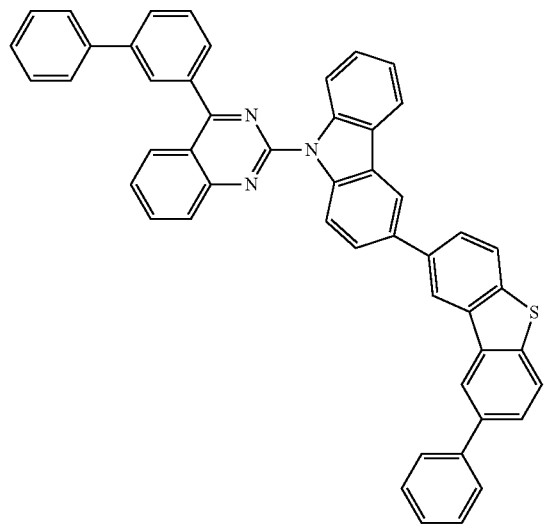
C-68
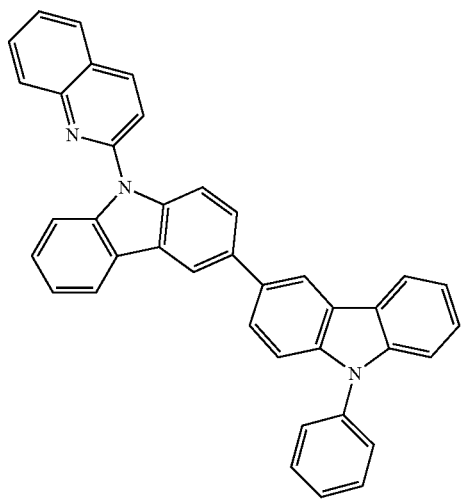
C-69
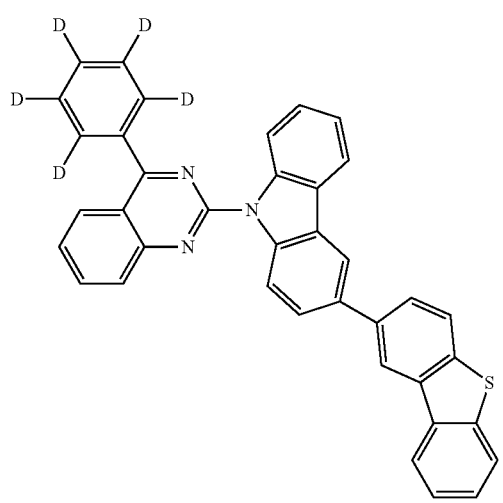
C-70
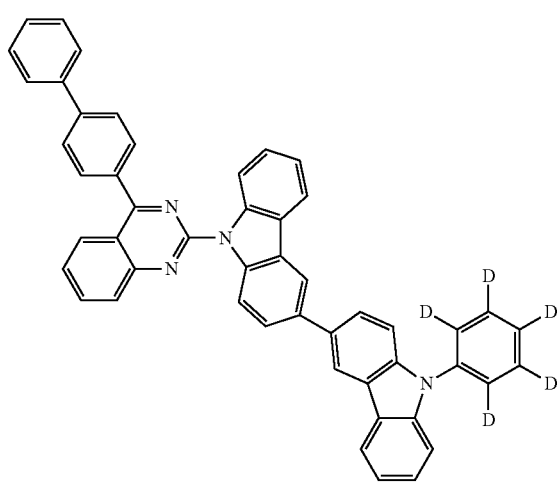

C-71
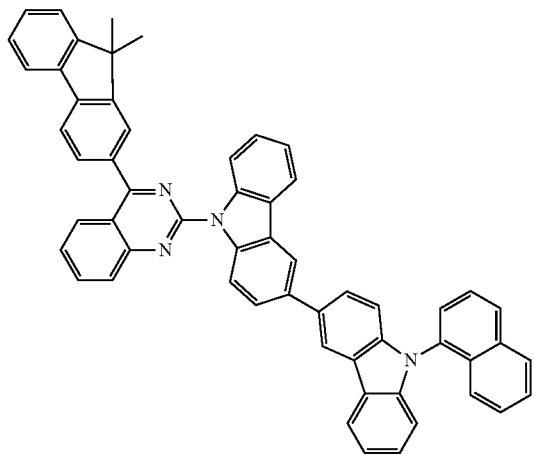
C-72
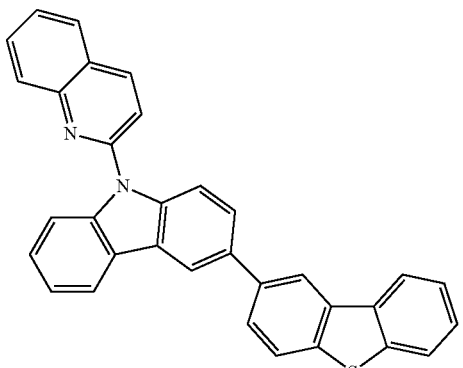
C-73
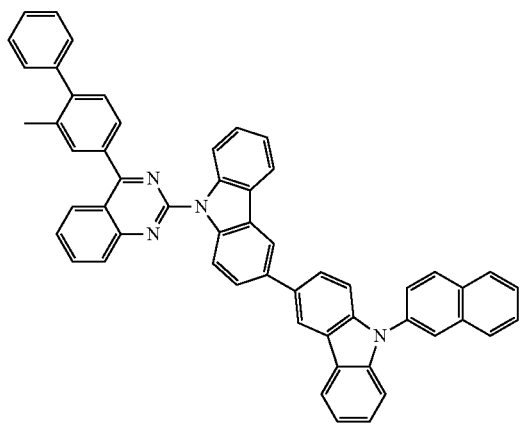
C-74
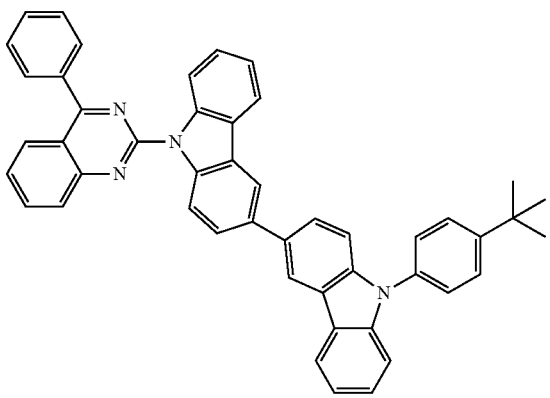
C-75
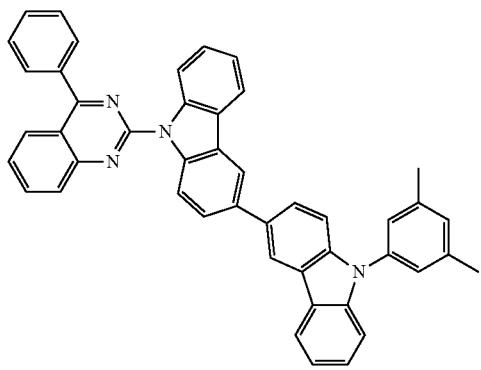
C-76
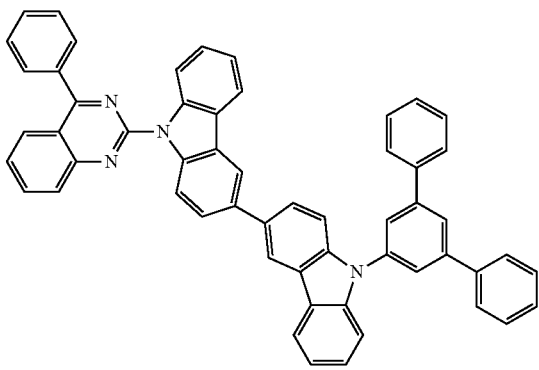

-continued
C-77
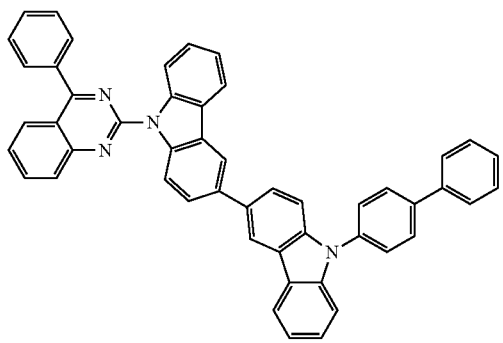
C-78
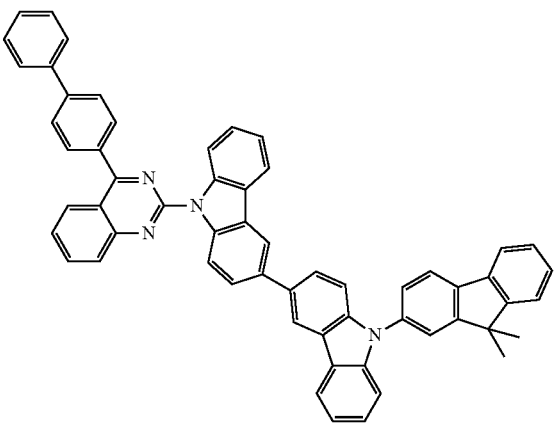
C-79
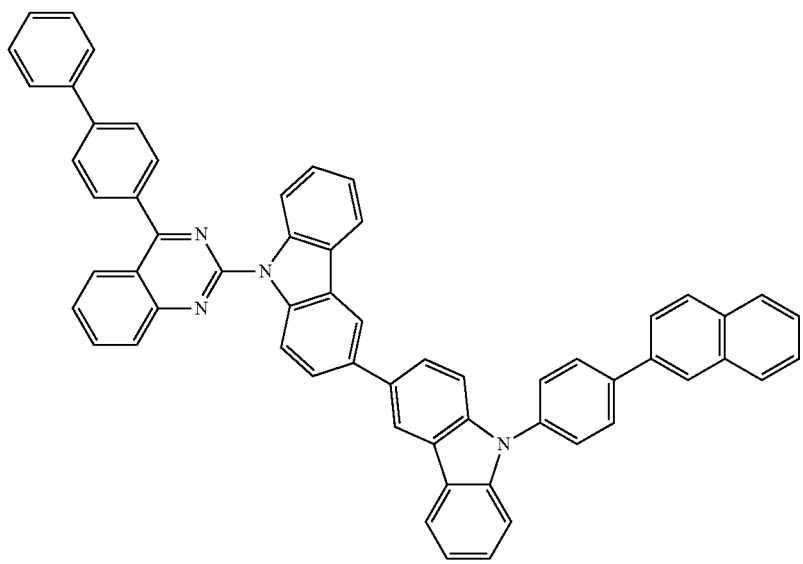
C-80
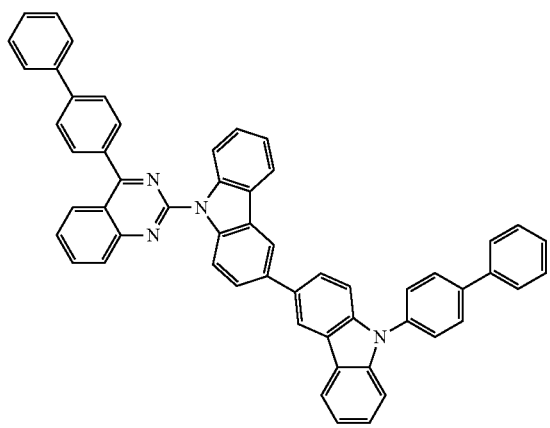
C-81
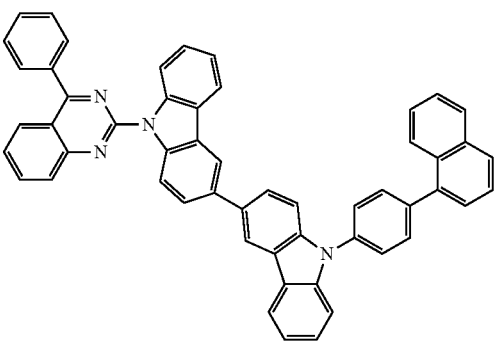

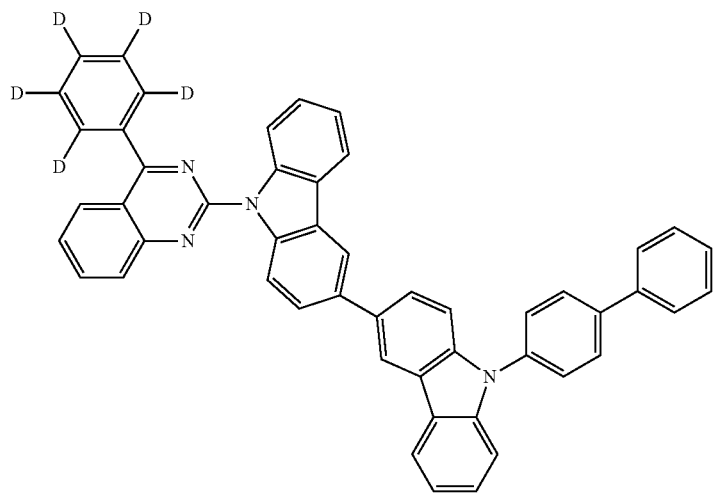
C-82
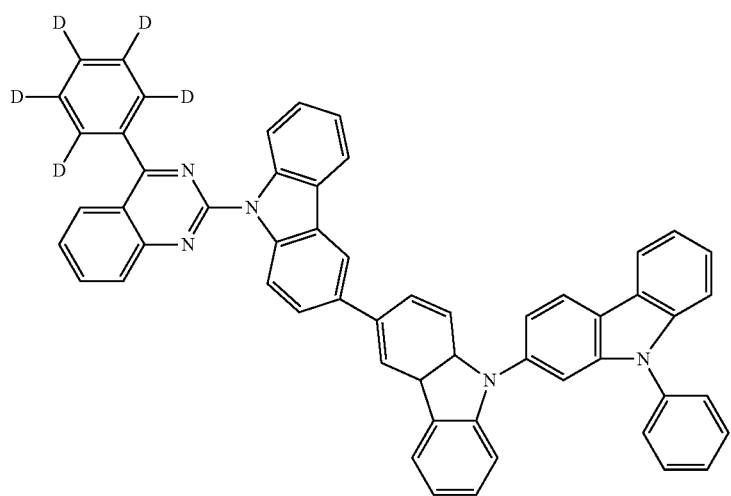
C-83
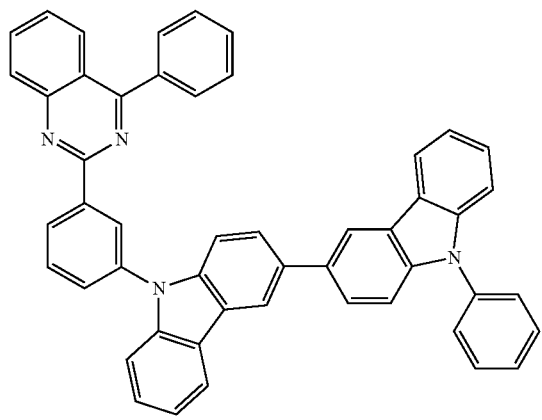
C-84
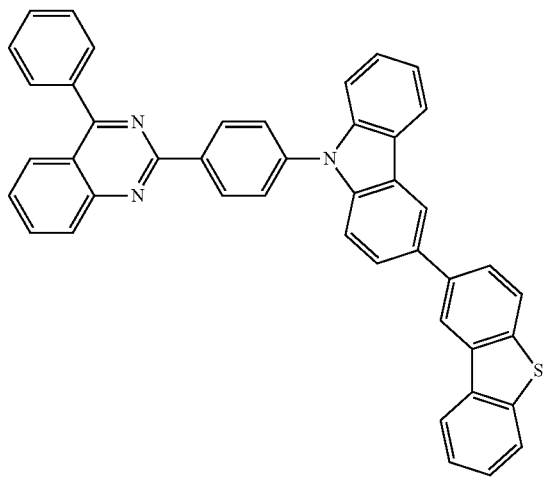
C-85

-continued
C-86
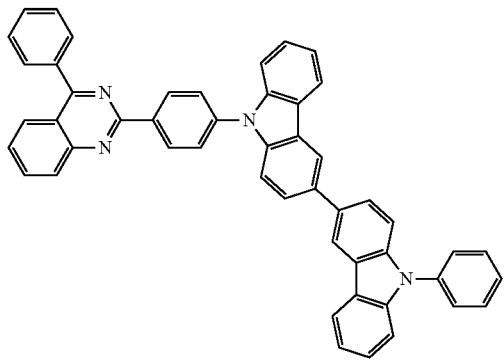
C-87
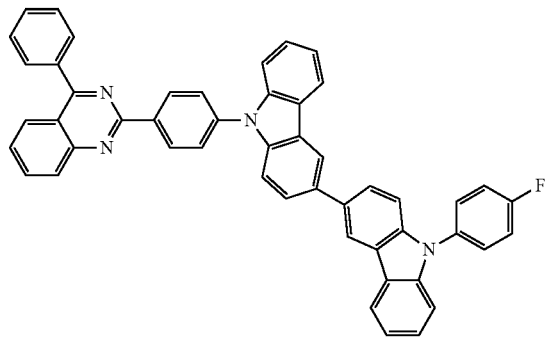
C-88
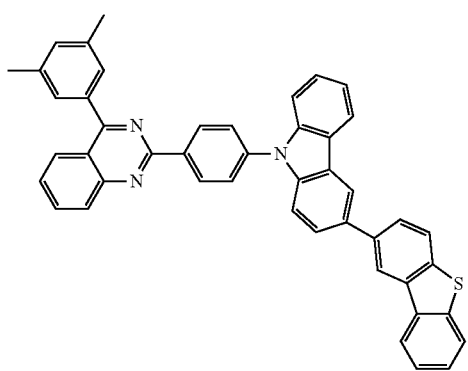
C-89
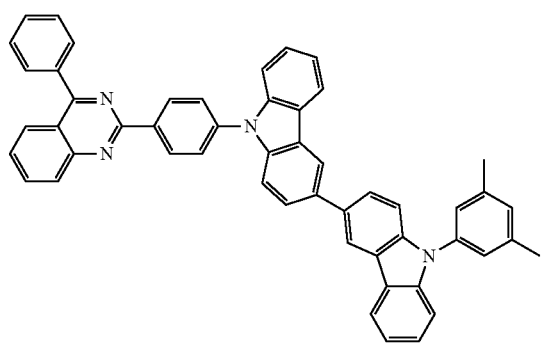
C-90
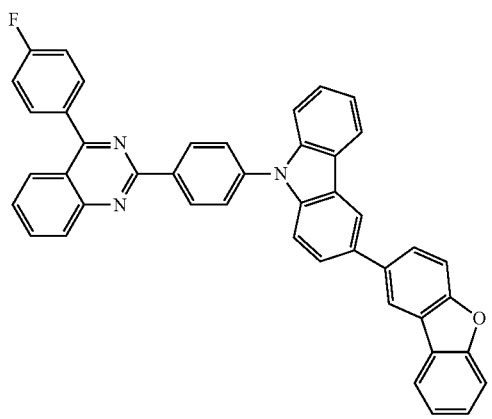
C-91
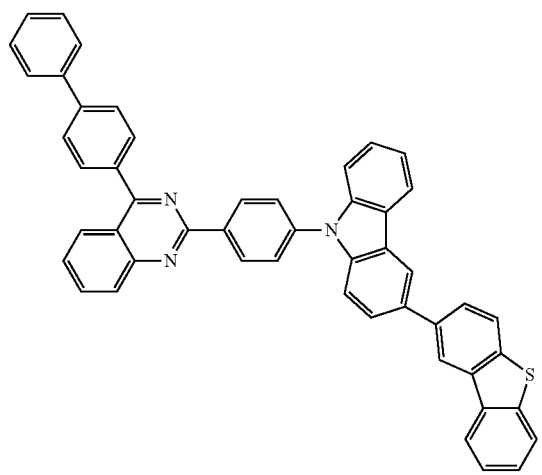

-continued
C-92
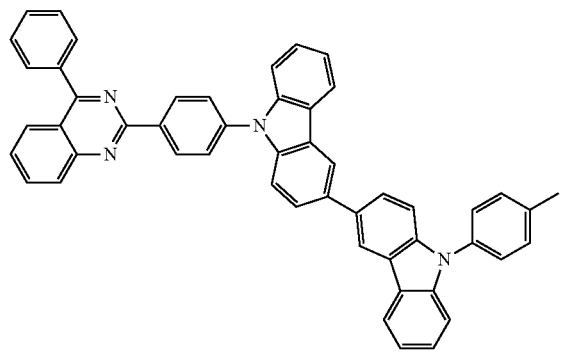
C-93
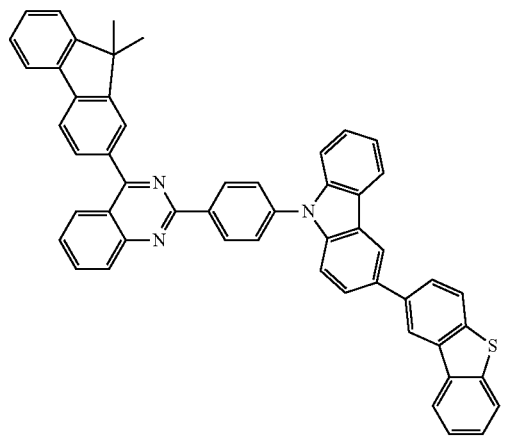
C-94
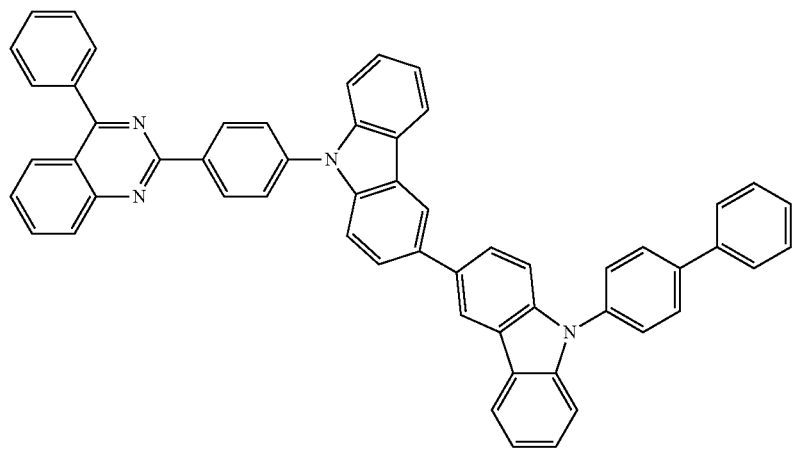
C-95
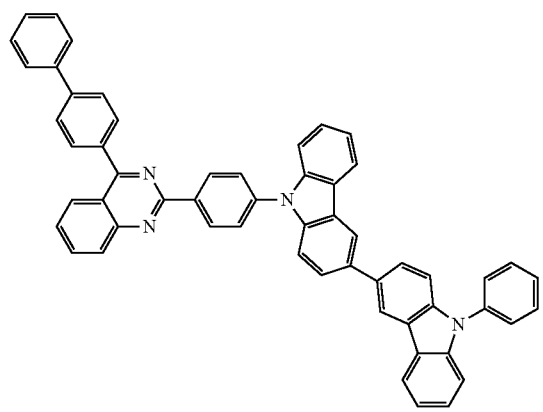
C-96
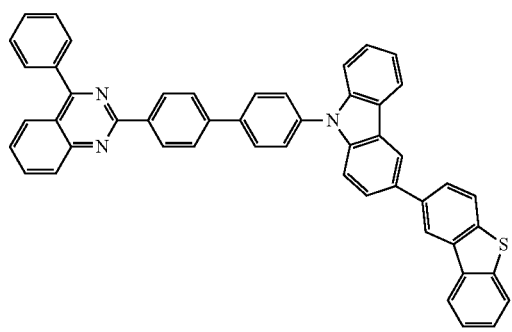

-continued
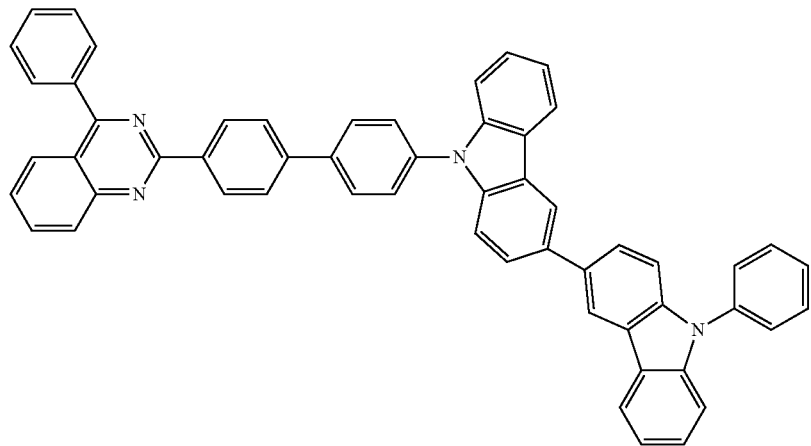
C-97
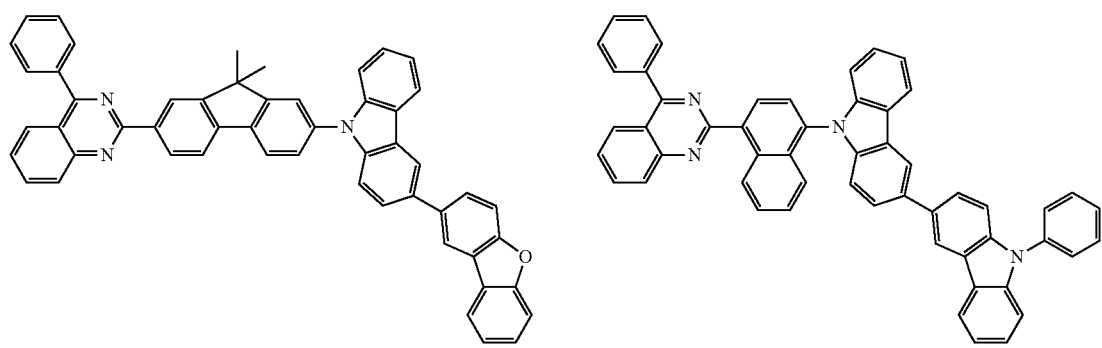
C-98  C-99
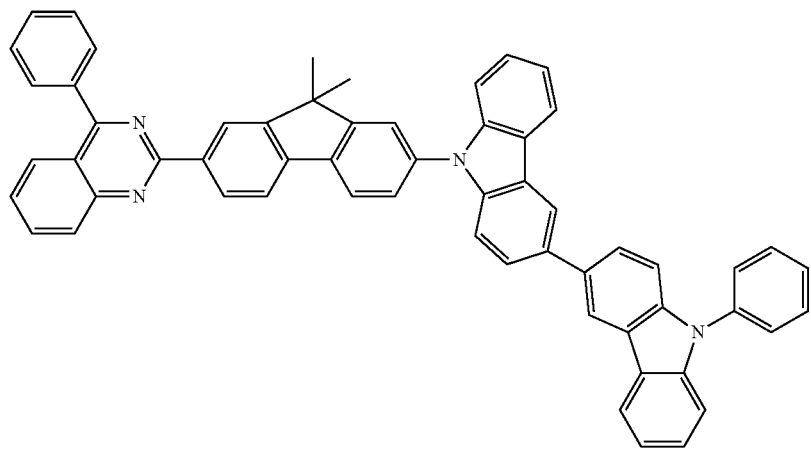
C-100
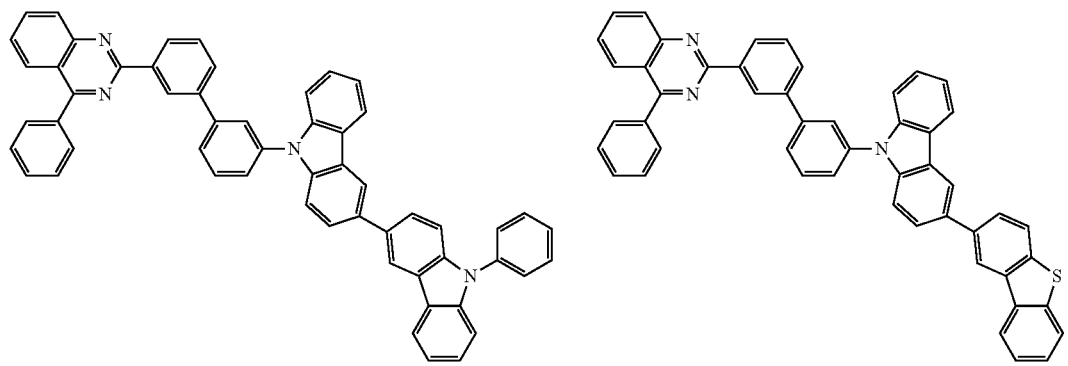
C-101  C-102

C-103
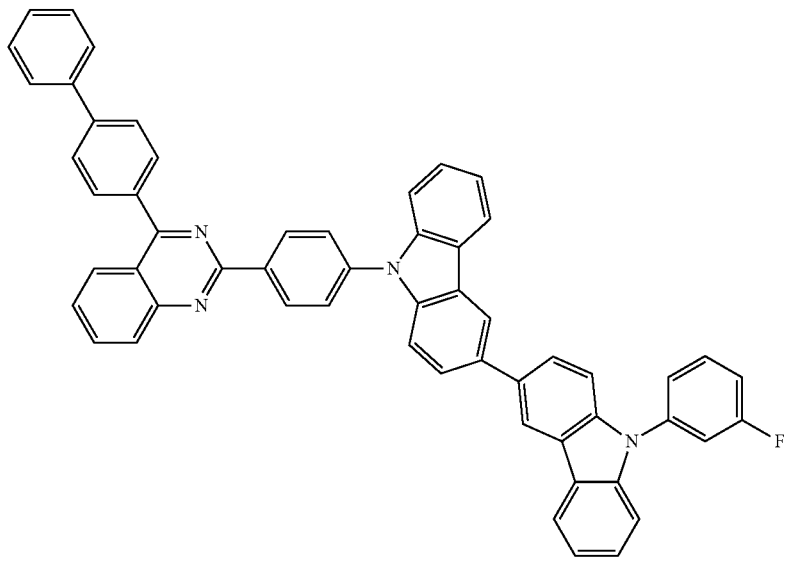
C-104
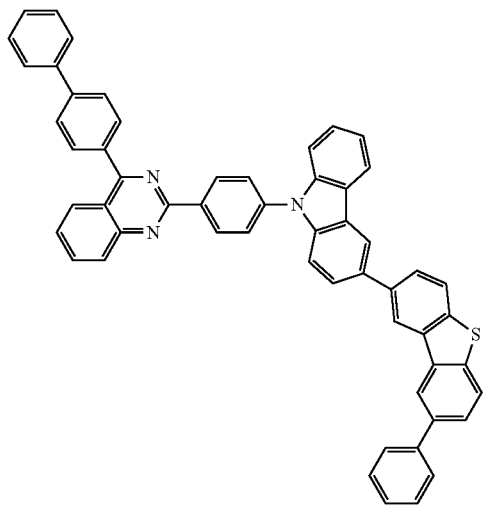
C-105
C-106
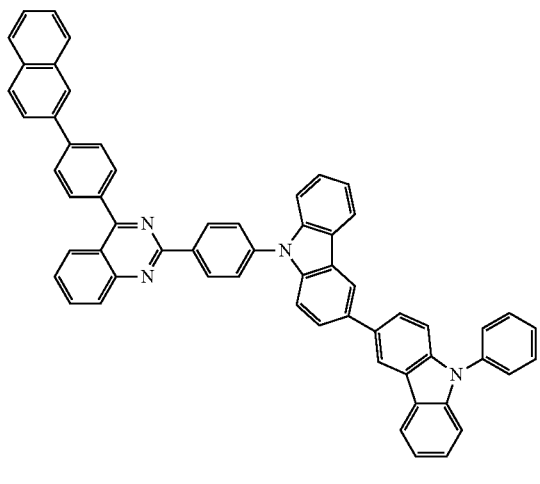
C-107
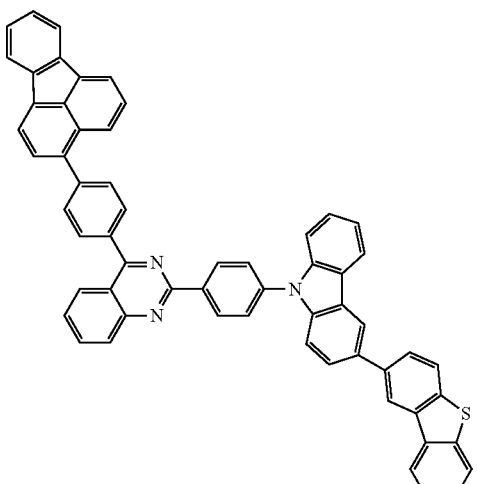

-continued
C-108
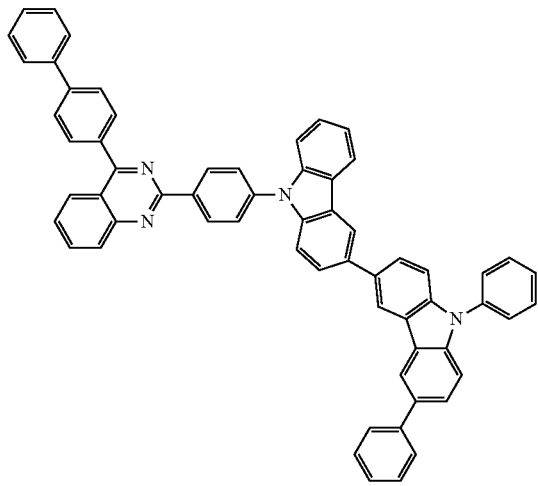
C-109
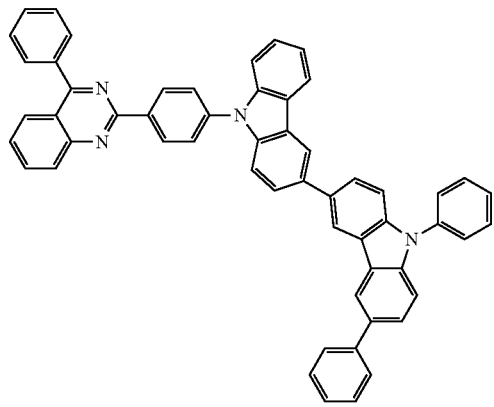
C-110
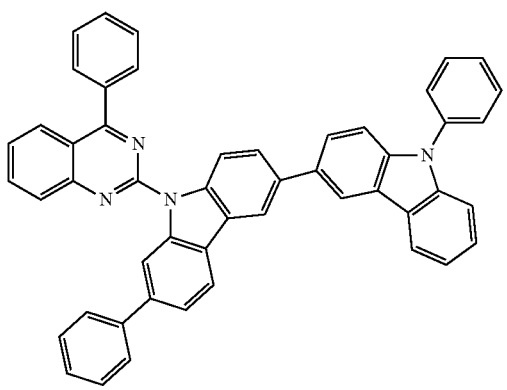
C-111
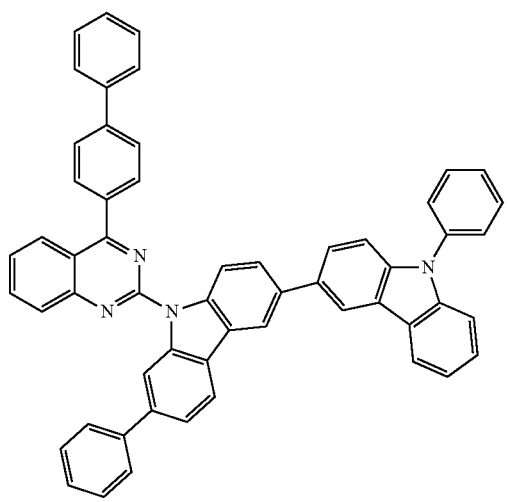
C-112
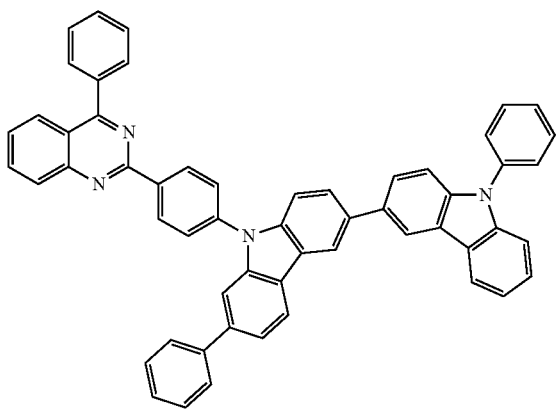
C-113
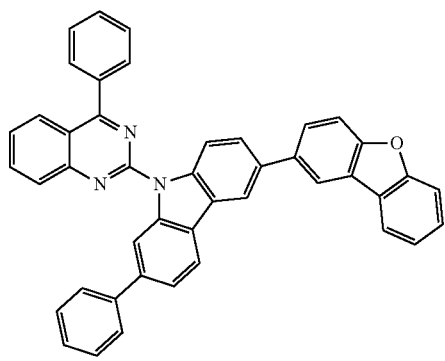

-continued
C-114
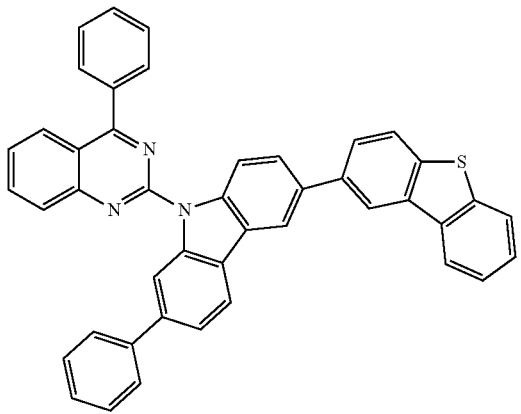
C-115
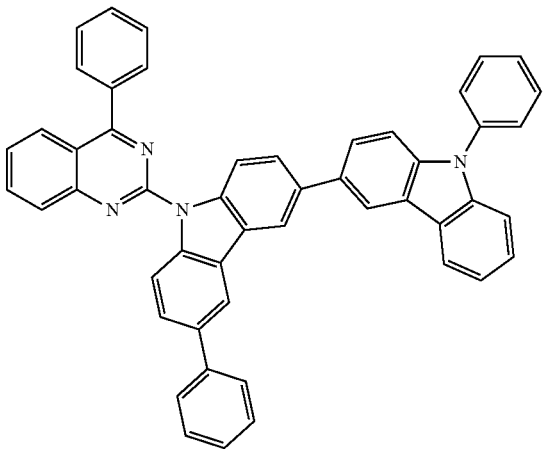
C-116
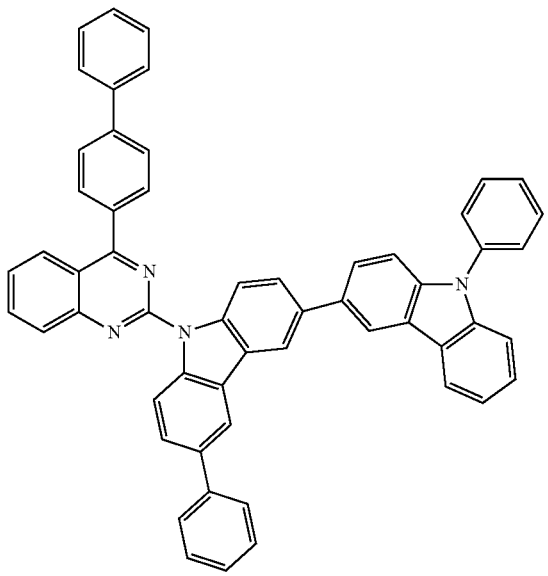
C-117
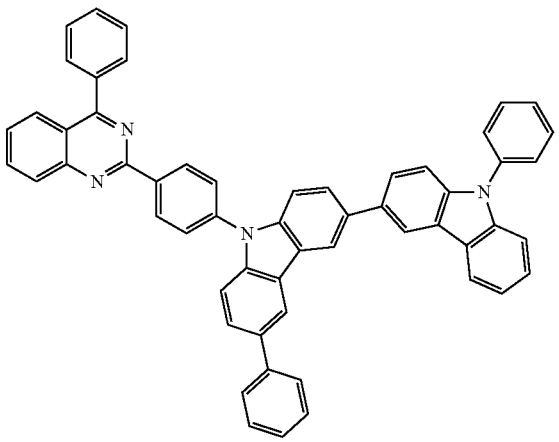
C-118
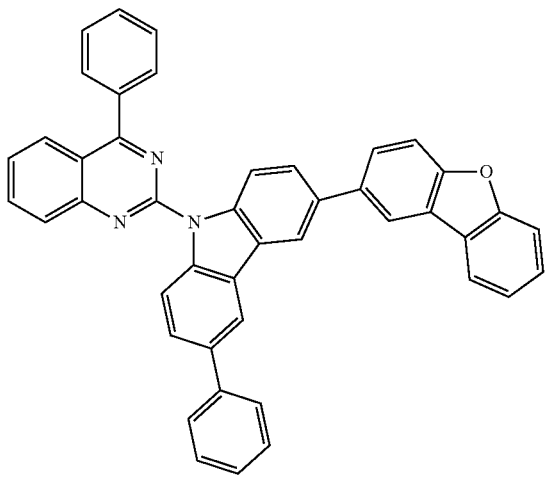
C-119
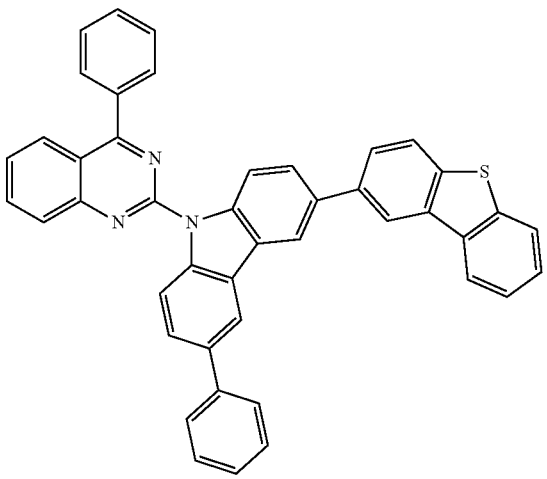

-continued
C-120
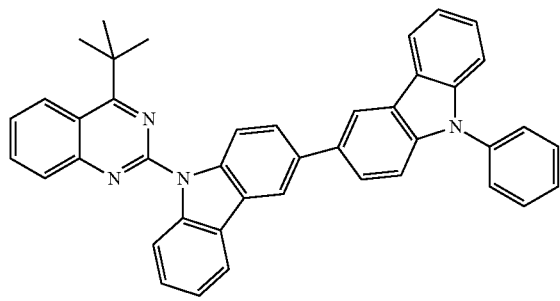
C-121
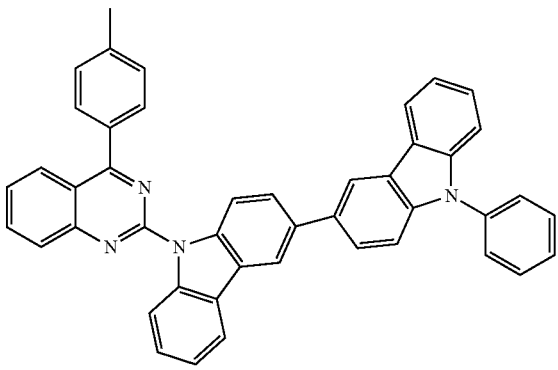
C-122
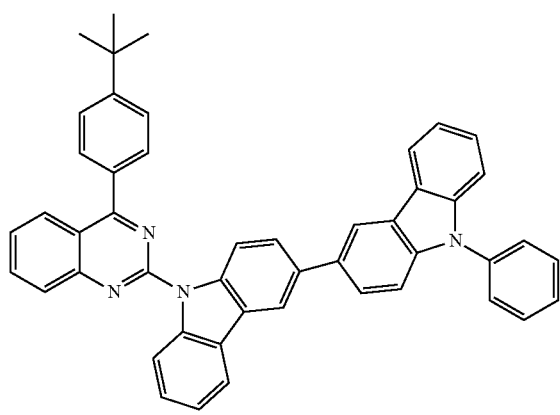
C-123
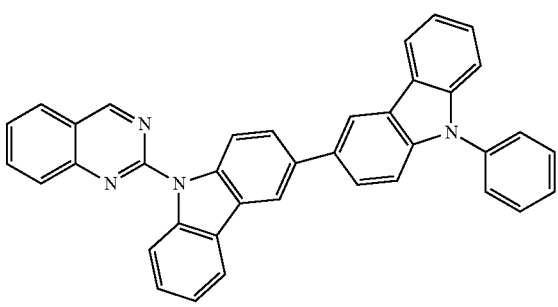
C-124
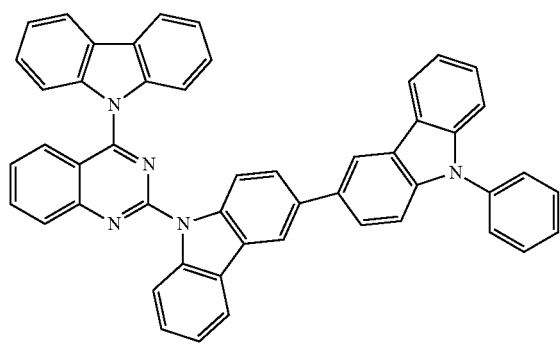
C-125
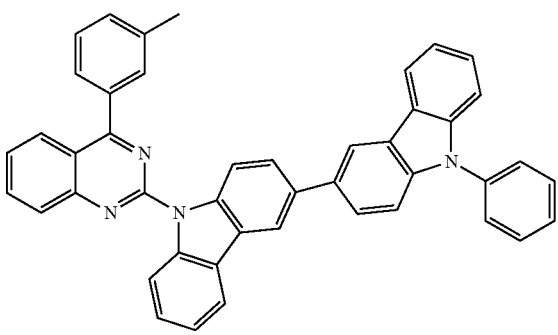
C-126
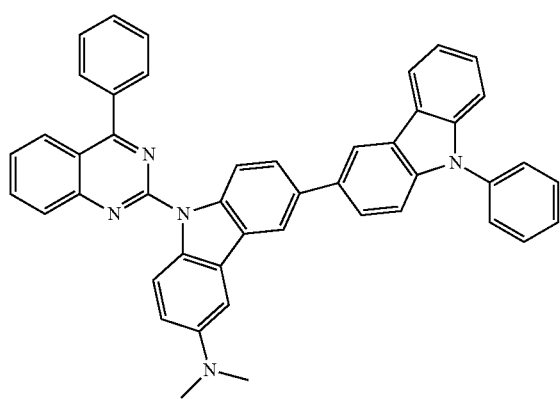
C-127
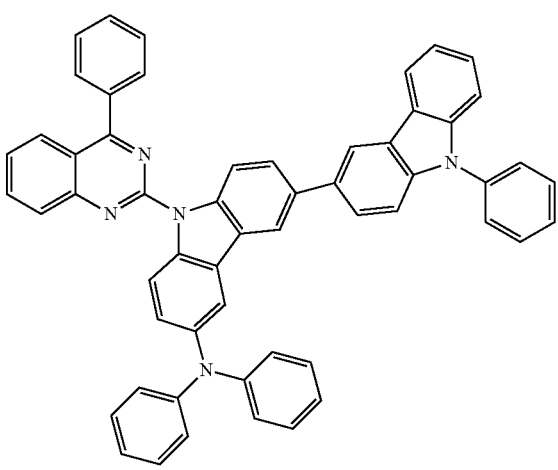

-continued
C-128
C-129
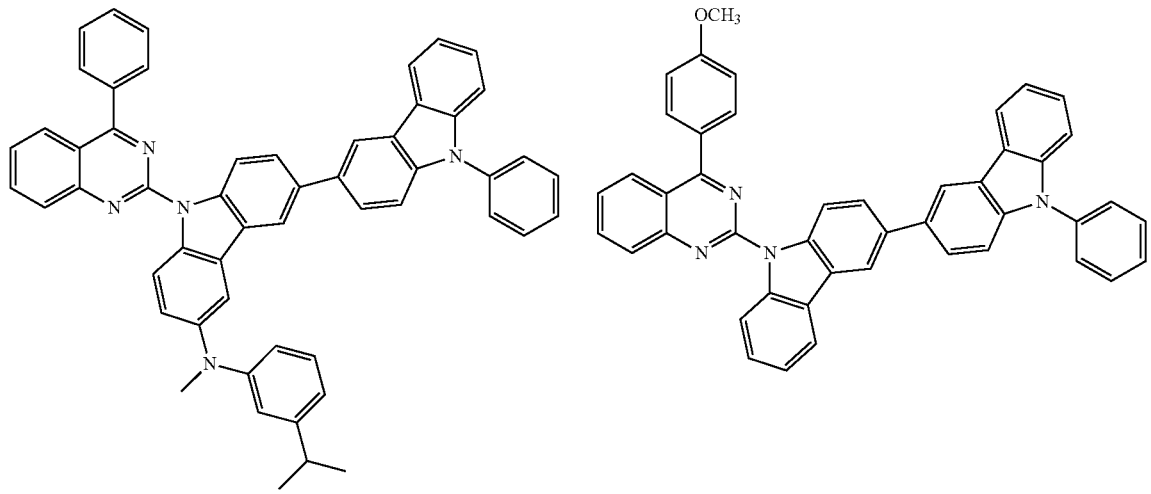
C-130
C-131
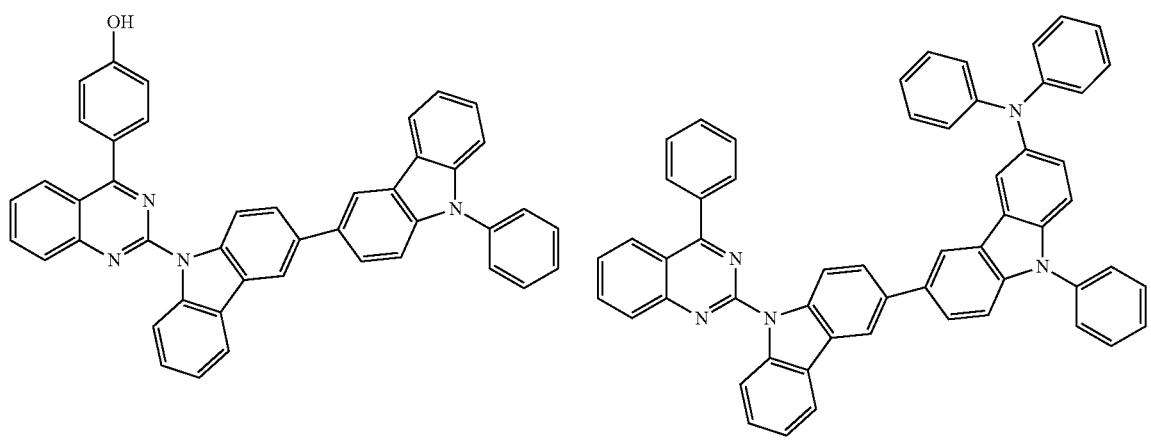
C-132
C-133
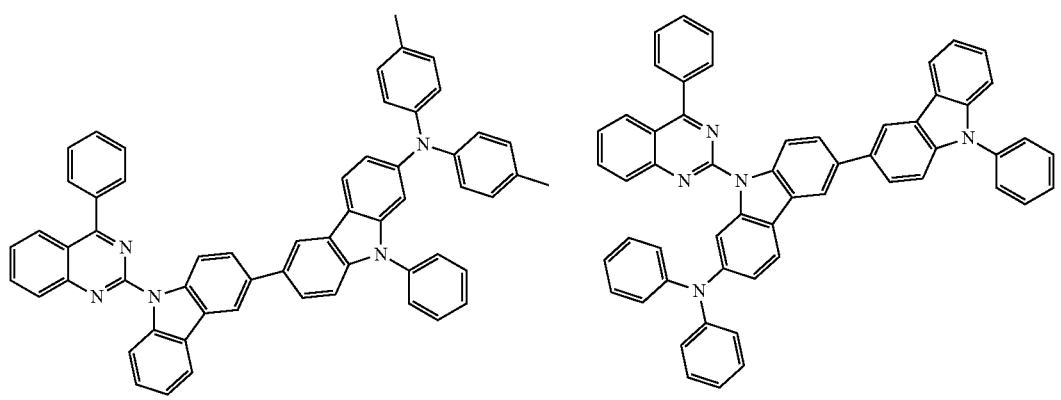

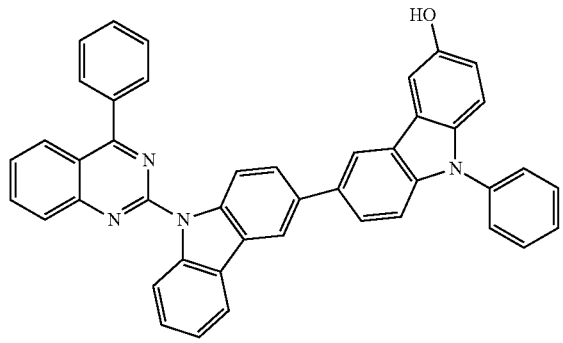
C-134

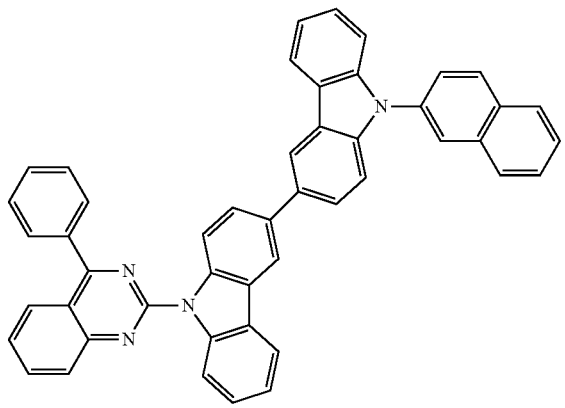
C-135

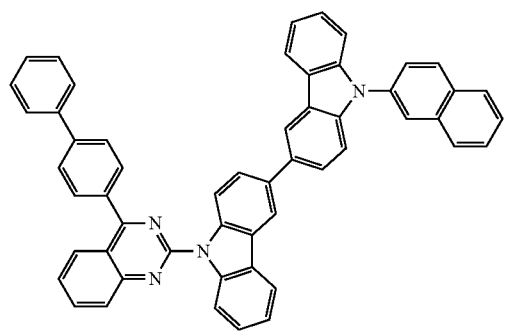
C-136

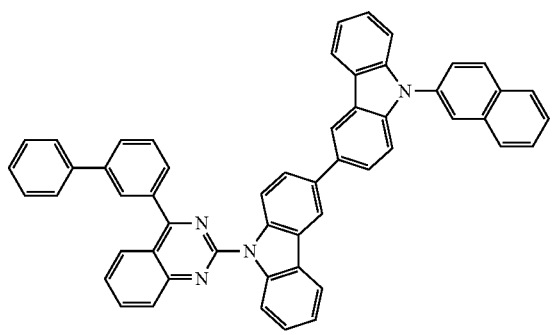
C-137

Of the above, without intending to be limited thereby, particularly preferred compounds are one or more of those depicted as compound C-1, C-5, C-9, C-77, C-135, C-136 or C-137. Particularly preferred compounds may be selected from C-1, C-5, C-9, or C-77. Particularly preferred compounds may be selected from C-135, C-136 or C-137.

Another feature of the present teachings is the possibility to realize a glass transition temperature ($T_g$) (as measured by differential scanning calorimetry) for the compound of Formula 1 (namely, the host material of a light emitting layer of the invention) in excess of about 80° C., about 90° C., or about 100° C. The glass transition temperature for the host material may be below about 350° C., below about 325° C., or below about 300° C.

Organic electroluminescent compounds according to the present invention (e.g., for use as a host material) can be prepared by well-known methods in the art, for example, according to the following scheme 1.

[Scheme 1]

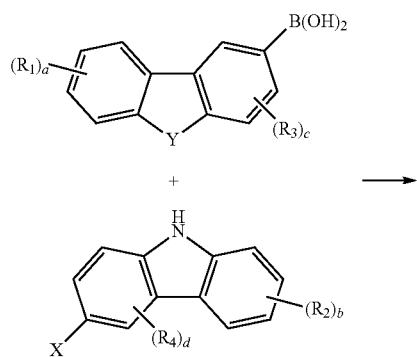

-continued

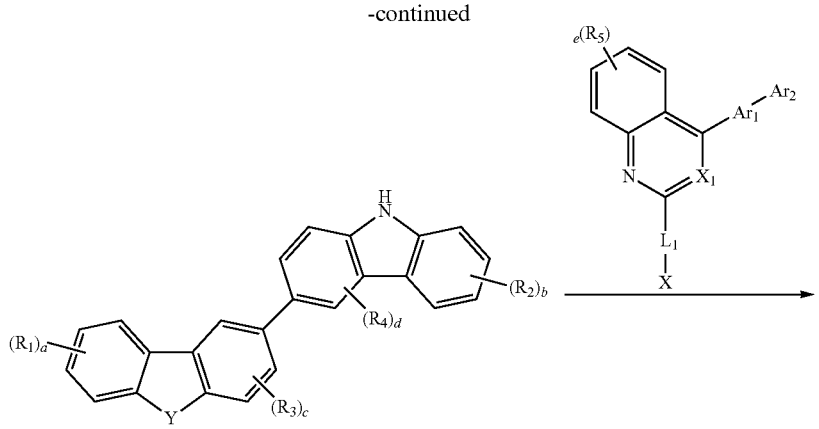

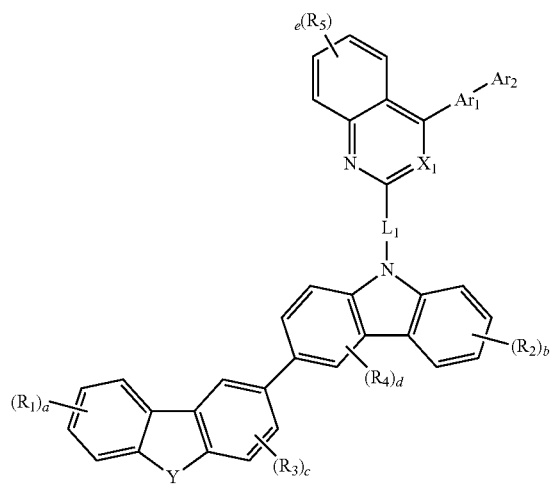

wherein, $R_1$ to $R_5$, $Ar_1$, $Ar_2$, Y, $X_1$, $L_1$, a, b, c, d and e are as defined in formula 1 above, and X represents a halogen.

Further, the present invention provides a light emitting layer, and/or an organic electroluminescent device comprising the organic electroluminescent compound of formula 1.

Said organic electroluminescent device comprises a first electrode, a second electrode and at least one organic layer, namely a light emitting layer, between said first electrode and said second electrode. Said organic layer comprises at least one organic electroluminescent compound of formula 1. Further, said organic layer comprises a light-emitting layer in which the organic electroluminescent compound of formula 1 is comprised as a host material. Where the organic electroluminescent compound of formula 1 is comprised as a host material in the light-emitting layer, said light-emitting layer further comprises at least one phosphorescent dopant. In the organic electroluminescent device of the present invention, said phosphorescent dopant is not particularly limited, but may be selected from compounds represented by the following formula 2:

$M^1 L^{101} L^{102} L^{103}$ [Formula 2]

wherein $M^1$ is selected from the group consisting of Ir, Pt, Pd and Os; $L^{101}$, $L^{102}$ and $L^{103}$ each independently are selected from the following structures:

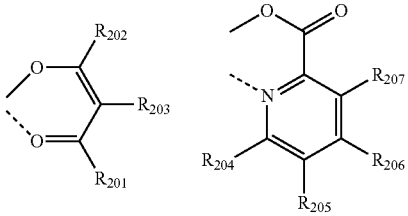

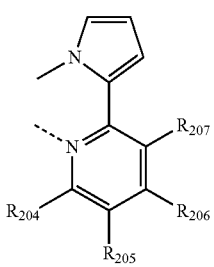 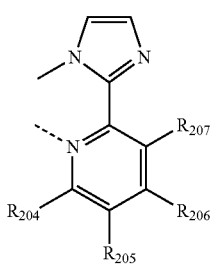

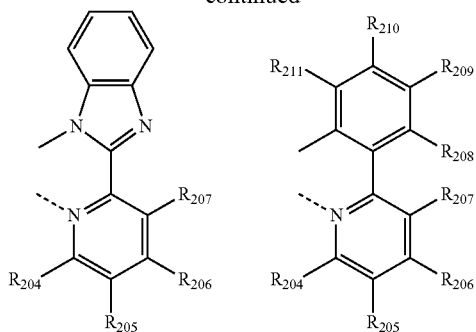
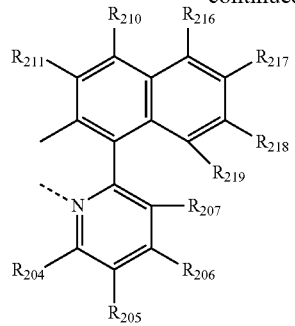
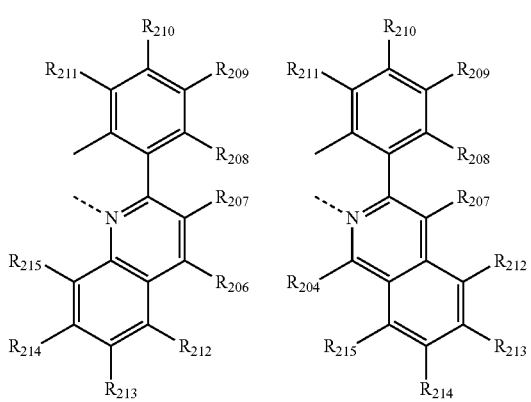
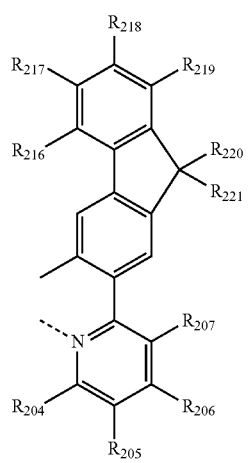
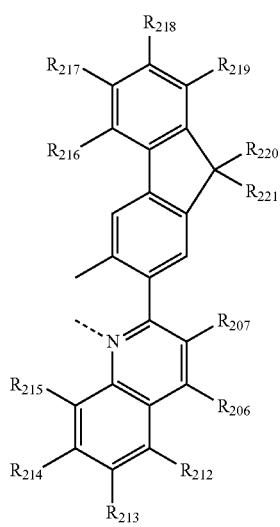
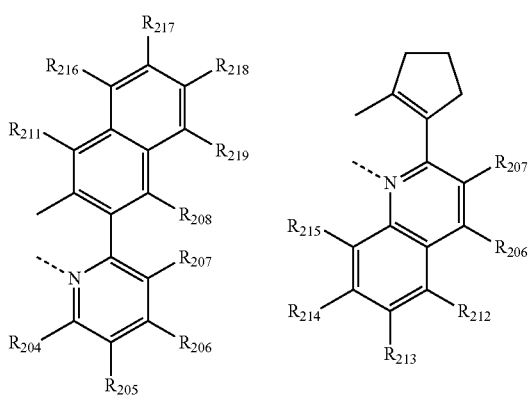
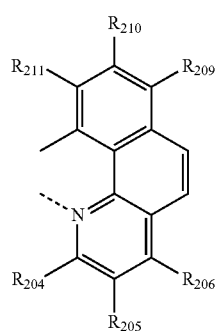
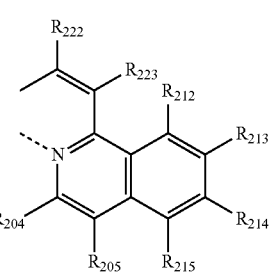
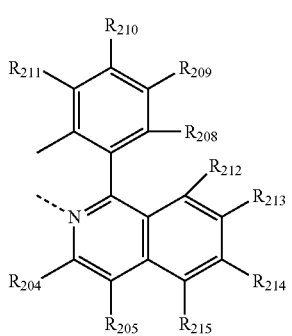
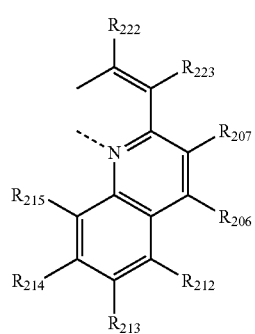
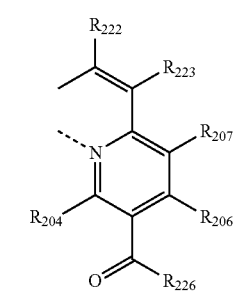

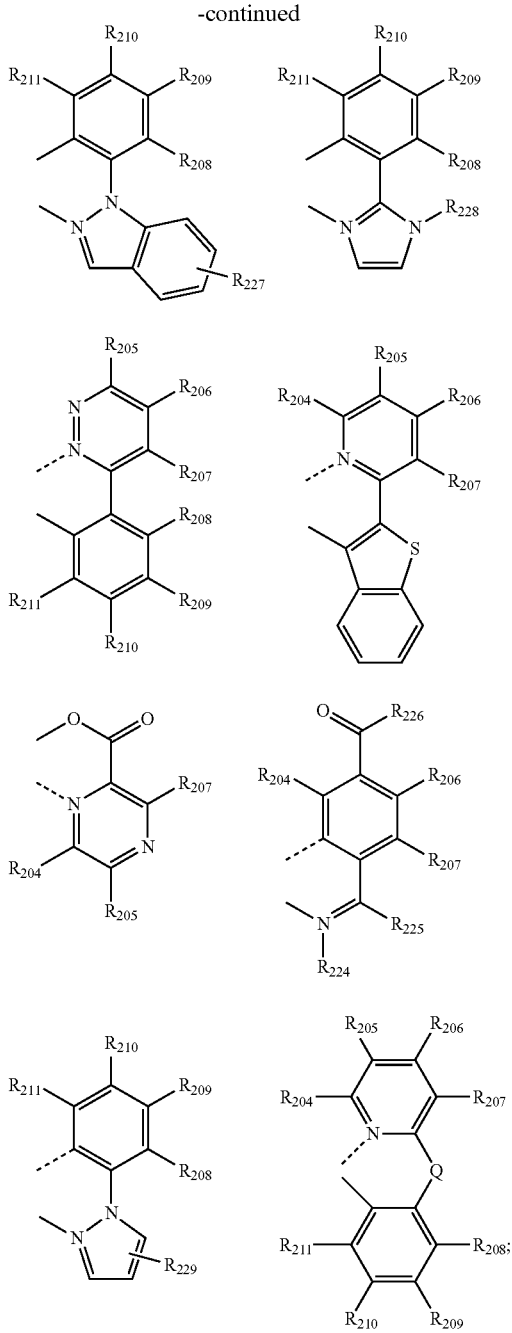

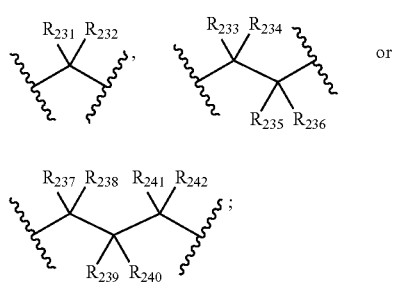

group, a cyano group or a halogen; $R_{220}$ to $R_{223}$ each independently represent hydrogen, deuterium, a (C1-C30)alkyl group unsubstituted or substituted by a halogen(s), or a (C6-C30)aryl group unsubstituted or substituted by a (C1-C30)alkyl group(s); $R_{224}$ and $R_{225}$ each independently represent hydrogen, deuterium, a substituted or unsubstituted (C1-C30)alkyl group, a substituted or unsubstituted (C6-C30)aryl group, or a halogen, or $R_{224}$ and $R_{225}$ may be linked to each other via a (C3-C12)alkylene group or (C3-C12)alkenylene group with or without a fused ring, to form a mono- or polycyclic alicyclic ring or a mono- or polycyclic aromatic ring; $R_{226}$ represents a substituted or unsubstituted (C1-C30)alkyl group, a substituted or unsubstituted (C6-C30)aryl group, a substituted or unsubstituted 5- or 30-membered heteroaryl group or a halogen; $R_{227}$ to $R_{229}$ each independently represent hydrogen, deuterium, a substituted or unsubstituted (C1-C30)alkyl group, a substituted or unsubstituted (C6-C30)aryl group or a halogen; Q represents $R_{231}$ to $R_{242}$ each independently represent hydrogen, deuterium, a (C1-C30)alkyl group unsubstituted or substituted by a halogen(s), a (C1-C30)alkoxy group, a halogen, a substituted or unsubstituted (C6-C30)aryl group, a cyano group, a substituted or unsubstituted (C5-C30)cycloalkyl group, or each of $R_{231}$ to $R_{242}$ may be linked to an adjacent substituent via (C2-C30)alkylene group or (C2-C30)alkenylene group to form a spiro ring or a fused ring or may be linked to $R_{207}$ or $R_{208}$ via (C2-C30)alkylene group or (C2-C30)alkenylene group to form a saturated or unsaturated fused ring.

With more particularity, Formula 2 may be represented by the following:

$$M^1L^{101}L^{102}L^{103}$$ [Formula 2]

wherein $M^1$ is Ir;
$L^{101}$ and $L^{102}$ are the same and represent

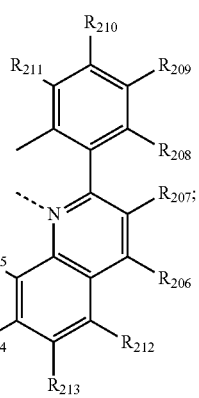

$R_{201}$ to $R_{203}$ each independently represent hydrogen, deuterium, a (C1-C30)alkyl group unsubstituted or substituted by a halogen(s), a (C6-C30)aryl group unsubstituted or substituted by a (C1-C30)alkyl group(s), or a halogen; $R_{204}$ to $R_{219}$ each independently represent hydrogen, deuterium, a substituted or unsubstituted (C1-C30)alkyl group, a substituted or unsubstituted (C1-C30)alkoxy group, a substituted or unsubstituted (C3-C30)cycloalkyl group, a substituted or unsubstituted (C2-C30)alkenyl group, a substituted or unsubstituted (C6-C30)aryl group, a substituted or unsubstituted mono- or di-(C1-C30)alkylamino group, a substituted or unsubstituted mono- or di-(C6-C30)arylamino group, $SF_5$, a substituted or unsubstituted tri(C1-C30)alkylsilyl group, a substituted or unsubstituted di(C1-C30)alkyl(C6-C30)arylsilyl group, a substituted or unsubstituted tri(C6-C30)arylsilyl and L$^{103}$ represents

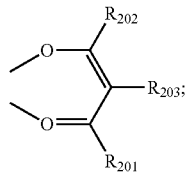

wherein R$_{201}$ to R$_{203}$ each independently represent hydrogen, deuterium, or a (C1-C30)alkyl group;

R$_{206}$ to R$_{208}$, R$_{210}$, and R$_{212}$ to R$_{215}$ each independently represent hydrogen, deuterium, a substituted or unsubstituted (C1-C30)alkyl group, or a substituted or unsubstituted (C6-C30)aryl group; and R$_{209}$ and R$_{211}$ each independently represent a substituted or unsubstituted (C1-C30)alkyl group.

For example, in Formula 2, R$_{209}$ and R$_{211}$ may each independently represent unsubstituted (C1-C30)alkyl group. By way of further example, R$_{207}$, R$_{208}$, R$_{210}$, R$_{214}$ and R$_{215}$ may each independently represent hydrogen or deuterium.

Examples of the iridium complex dopants of formula 2 include the following, but are not limited thereto:

D-1

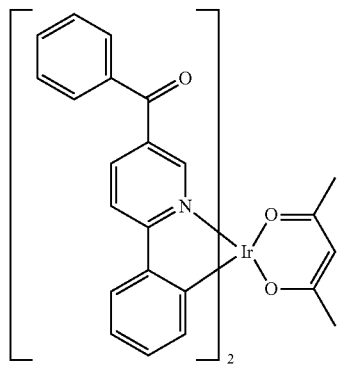

D-2

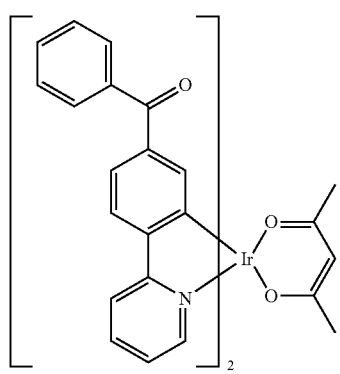

D-3

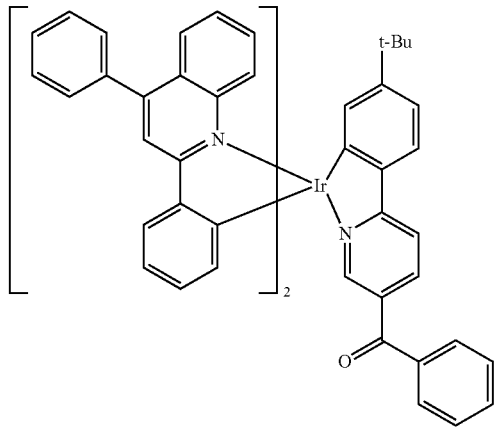

D-4

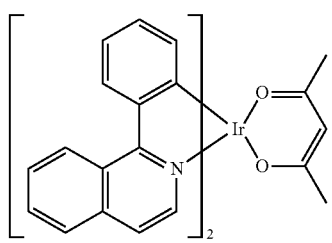

D-5

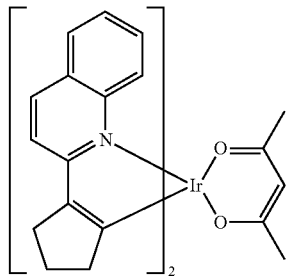

D-6

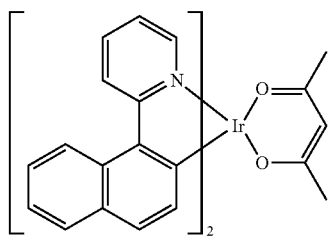

D-7

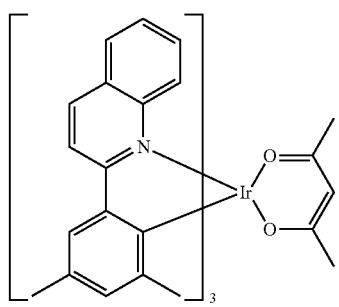

D-8 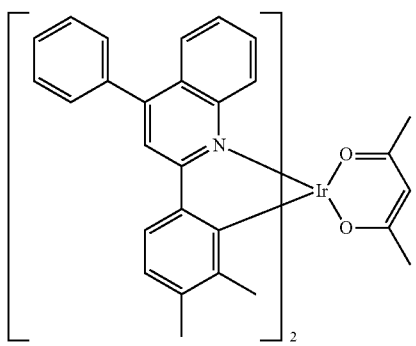
D-9 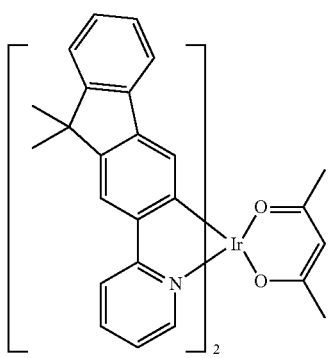
D-10 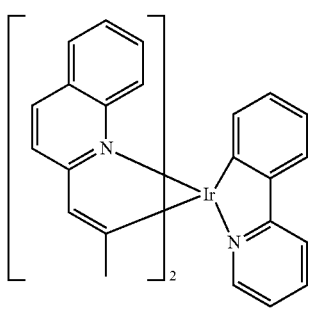
D-11 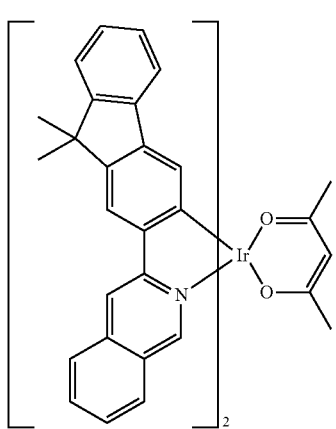
D-12 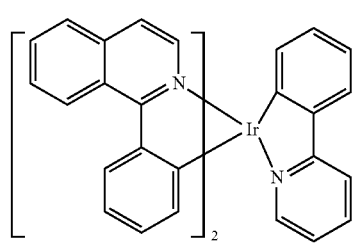
D-13 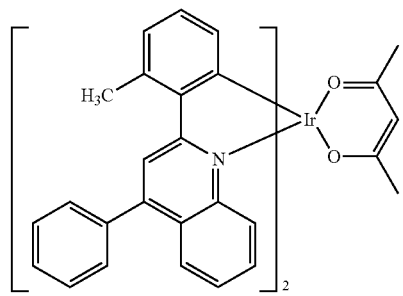
D-14 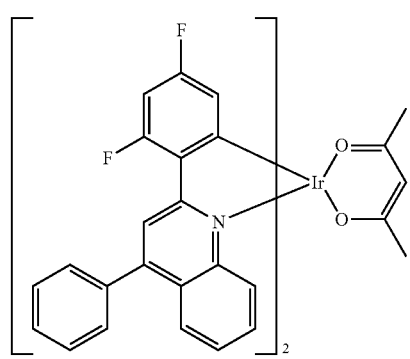
D-15 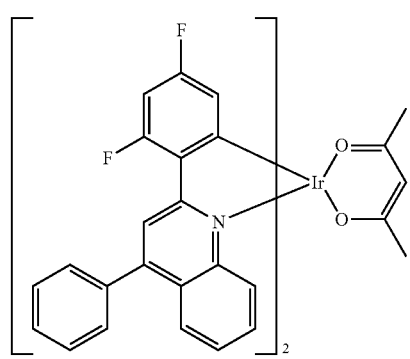
D-16 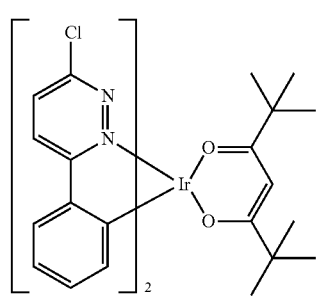

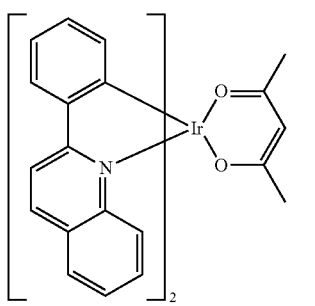
D-17
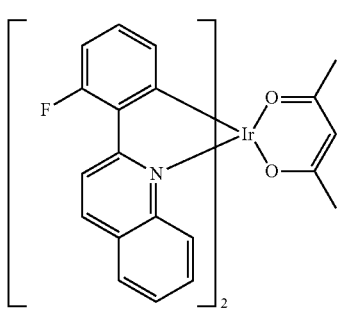
D-18
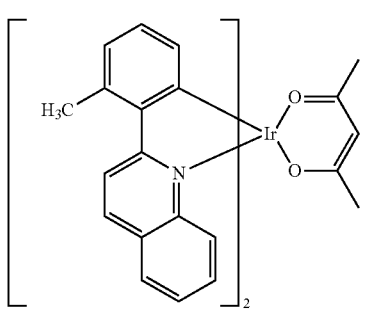
D-19
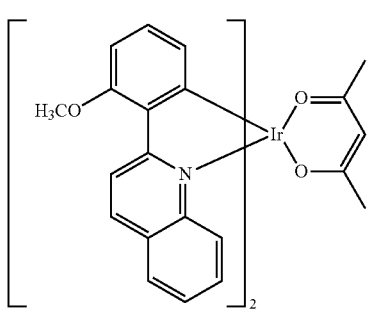
D-20
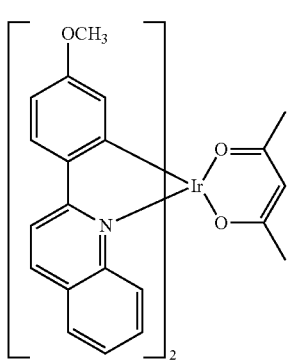
D-21
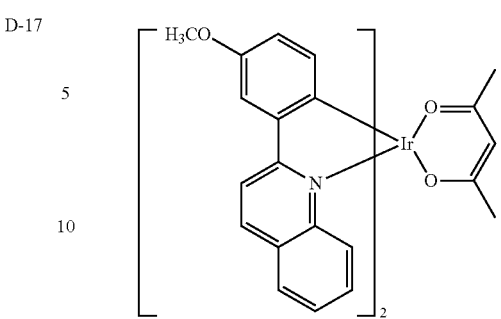
D-22
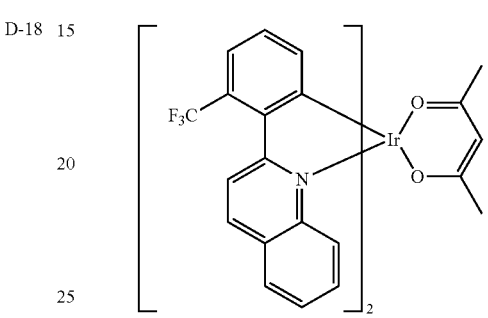
D-23
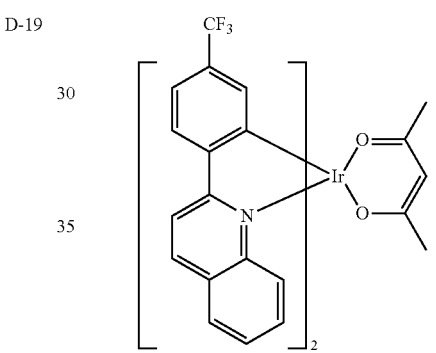
D-24
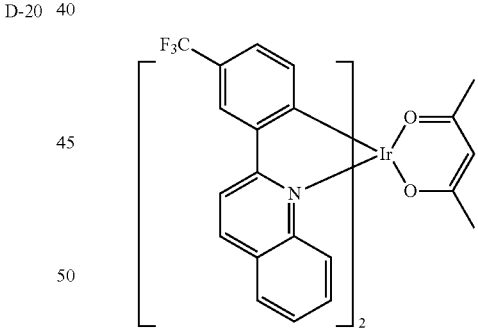
D-25
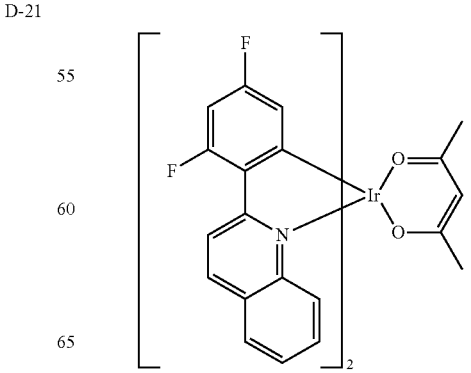
D-26

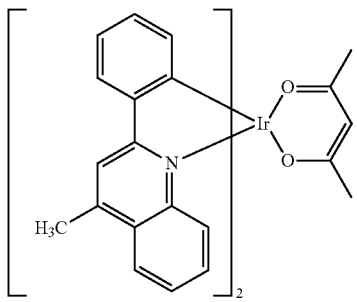
D-27

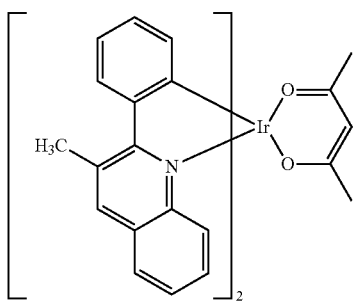
D-28

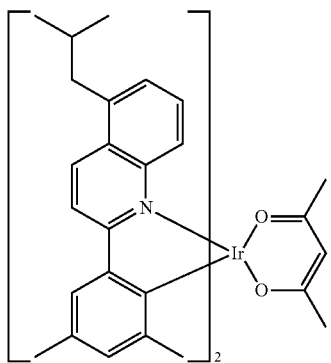
D-29

Of the above, without intending to be limited thereby, particularly preferred complexes are one or both of those depicted as complex D-7 or D-29.

For the light emitting layer herein, the amount by weight of the host material to the metal complex (e.g., iridium complex) may be below about 100:1, 90:1, 80:1, 70:1, or 60:1. The amount by weight of the host material to the metal complex (e.g., iridium complex as described herein) may be above about 10:1. 20:1, or 30:1. For example, the amount by weight of the host material to the metal complex (e.g., iridium complex as described herein) may be range from about 100:1 to about 10:1.

A possible approach to manufacture a layer is to deposit each of the host material and the metal complex dopant in their respective amounts by a suitable deposition (e.g., vapor deposition) process. The relative amounts can be varied as desired, for example, by selecting different deposition rates for each. The layers are deposited to a desired thickness. For example the thickness may be greater than about 1 nm, greater than about 5 nm, or greater than about 10. The thickness may be less than about 300 nm, less than about 200 nm, or less than about 100 nm.

With more particularity, for a light emitting layer having a combination of a host of formula 1 and a metal complex of formula 2, the $Ar_1$ may be a single bond or it can be a substituted or unsubstituted C6-C30 arylene (e.g., a substituted or unsubstituted C6 arylene). For such combination, $Ar_2$ may be a substituted or unsubstituted C6-C30 aryl (e.g., a C6 aryl). For such combination, $R_{212}$ may be hydrogen, deuterium, a substituted or unsubstituted C1-C30 alkyl or a substituted or unsubstituted C6-C30 aryl (e.g., $R_{212}$ may be hydrogen or a substituted or unsubstituted C1-C30 alkyl). For such a combination, $R_{13}$ may be a substituted or unsubstituted C6-C20 aryl (e.g., $R_{13}$ may be a substituted or unsubstituted C6, C10, C12, C16 or other aryl).

The organic electroluminescent device according to the present invention may further comprise, in addition to the organic electroluminescent compound according to the present invention, at least one amine-based compound selected from the group consisting of arylamine-based compounds and styrylarylamine-based compounds.

In the organic electroluminescent device according to the present invention, the organic layer, may further comprise at least one metal selected from the group consisting of metals of Group 1, metals of Group 2, transition metals of the $4^{th}$ period, transition metals of the $5^{th}$ period, lanthanides and organic metals of d-transition elements of the Periodic Table, or at least one complex compound comprising said metal. The organic layer may comprise a light-emitting layer and a charge generating layer.

The organic electroluminescent device according to the present invention may emit a white light by further comprising in addition to the organic electroluminescent compound according to the present invention, at least one light-emitting layer which comprises a blue electroluminescent compound, a red electroluminescent compound or a green electroluminescent compound. If necessary, the organic electroluminescent device may further comprise a yellow light-emitting layer or an orange light-emitting layer.

Preferred combinations of host and metal complex are such that they provide an organic layer, namely a light emitting layer, which exhibits a peak intensity at a wavelength within a range of about 600 nm to about 700 nm as measured by spectrophotometry (e.g., using a Varian brand Carry Eclipse Fluorescence spectrophotometer according to its standard operating parameters). A light emitting layer that includes a host material and a metal complex (e.g., an iridium complex as described herein) of the present teachings may luminesce red upon application of a driving voltage. The driving voltage may be a voltage of at least about 2 volts (V), at least about 4V, at least about 6V, or at least about 8V. The driving voltage may be a voltage below about 20V, below about 18V, below about 16V or below about 14V.

Preferably, in the organic electroluminescent device according to the present invention, at least one layer (hereinafter, "a surface layer") selected from a chalcogenide layer, a metal halide layer and a metal oxide layer may be placed on an inner surface(s) of one or both electrode(s). Specifically, it is preferred that a chalcogenide layer of silicon or aluminum is placed on an anode surface of an electroluminescent medium layer, and a metal halide layer or metal oxide layer is placed on a cathode surface of an electroluminescent medium layer. Such a surface layer provides operation stability for the organic electroluminescent device. Preferably, said chalcogenide includes $SiO_x(1 \leq X \leq 2)$, $AlO_x(1 \leq X \leq 1.5)$, SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

Preferably, in the organic electroluminescent device according to the present invention, a mixed region of an electron transport compound or a mixed region of a hole transport compound and an oxidative dopant may be placed on at least one surface of a pair of electrodes. In that case, the electron transport compound is reduced to an anion, and thus facilitates injecting and transporting electrons to an electroluminescent medium. Further, the hole transport compound is oxidized to a cation, and thus facilitates injecting and transporting holes to an electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge generating layer to prepare an electroluminescent device having two or more light emitting layers and emitting a white light.

The organic electroluminescent compound according to the present invention provides an organic light emitting layer and device, which has high luminous efficiency and a long operation lifetime and requires a low driving voltage improving power efficiency and power consumption.

For instance, a light emitting layer of the present invention, which may be employed for an OLED device, may show red emission. The red emission may haven luminance of at least 1,000 cd/m$^2$ at a driving voltage of 3.8 V and a current density of 3.4 mA/cm$^2$. For instance, the layer may show red emission (with a peak intensity at a wavelength within a range of about: 600 nm to about 700 nm as measured by spectrophotometry as described) having a luminance of at least about 800, at least about 900, or at least about 1,000 cd/m$^2$ at a driving voltage of below about 8V, below about 6V, or below about 4V (e.g., about 3.8V) and a current density of about 1 to about 10, about 2 to about 6, or about 3 to about 4 mA/cm$^2$. Further, the minimum time for a luminance of 5,000 nit to be reduced to 97% of the luminance may be at least 170 hours.

It is also possible that by use of the combination of the compounds of the invention and the metal complexes of the invention (e.g., an iridium complex, and particularly one as described in the present teachings, such as an alkylated complex as described), that operational lifetime (e.g., at about a 5000 nit level) can be surprisingly substantially higher than other combinations that have been employed. For example, it is believed possible that alkylated metal complex dopants (e.g., of formula 2 as described in the teachings) when used in combination with an organic electroluminescent compound (e.g., those of Formula 1 of the teachings) as a host material may be able to achieve at least about 1.3 times, about 1.5 times, about 1.8 times or about 2 times the operational lifetime as compared with a similar combination, but where the metal complex dopant is not alkylated.

In general, other aspects of the invention are that either or both of the metal complex or the host material of the organic layer (namely the light emitting layer) may be free of any halogen (e.g., in the form of a substituent), as may also be the situation for the light emitting layer as a whole. The organic electroluminescent compounds according to the present invention have superior properties than those of conventional electroluminescent compounds, and thus provide an organic electroluminescent device which has high luminous efficiency and a long operation lifetime and requires a low driving voltage improving power efficiency and power consumption.

Hereinafter, examples are provided for preparing the organic electroluminescent compounds, and properties of the organic electroluminescent devices using them.

The abbreviations used in the examples have the following meanings:

Ph: phenyl, MeOH: methanol, EtOH: ethanol, MC: methylene chloride, EA: ethyl acetate, DMF: dimethylformamide, n-Bu: normal-butyl, i-Pr: isopropyl, Me: methyl, THF: tetrahydrofuran, EDA: ethylene diamine, NBS: N-bromosuccinimide It is believed that the resulting Compounds C-9 of the preparation examples could exhibit a $T_g$ of from about 140° C. to about 150° C.

PREPARATION EXAMPLE 1

Preparation of Compound C-9

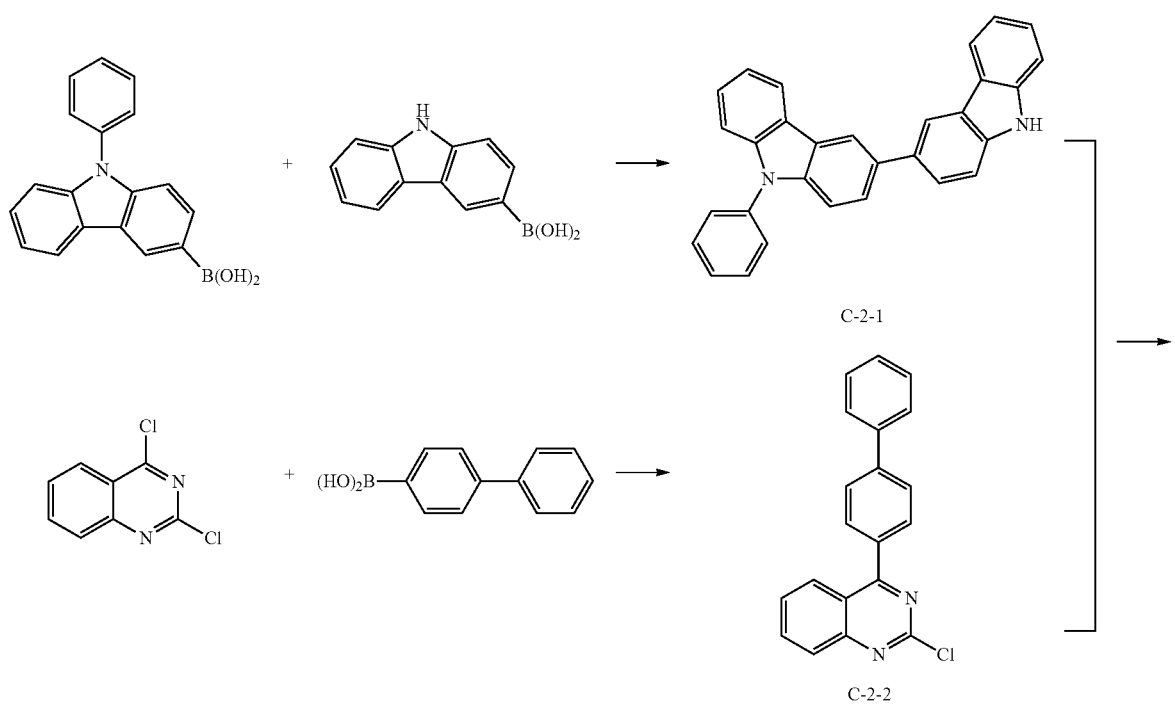

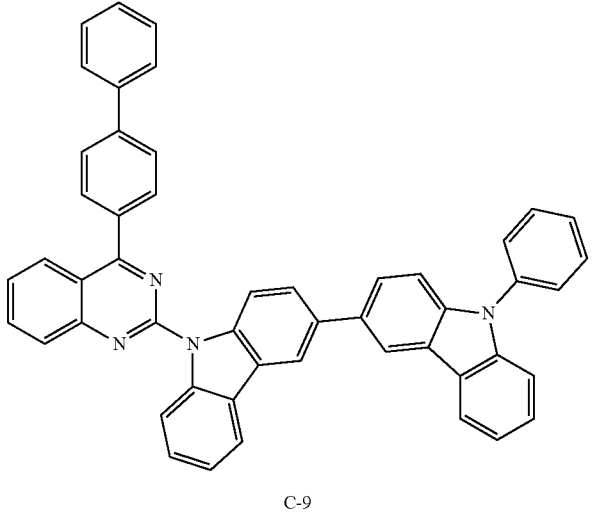

C-9

Preparation of Compound C-2-1

9-phenyl-9H-carbazol-3-yl boronic acid (14 g, 48.76 mmol), 3-bromo-9H-carbazole (10 g, 40.63 mmol), $K_2CO_3$ (13.5 g, 97.52 mmol) and $Pd(PPh_3)_4$ (2.35 g, 2.03 mmol) were added to toluene 200 mL, EtOH 50 mL and purified water 50 mL. After stirring the reaction mixture for 3 hours at 90 to 100° C., the mixture was cooled to room temperature. An aqueous layer was removed from the mixture by a gravity separation. The obtained organic layer was concentrated, was triturated with MC, and then was filtered to obtain compound C-2-1 (12 g, 72%).

Preparation of Compound C-2-2

2,4-dichloroquinazoline (20 g, 0.1 mol), biphenyl-4-yl boronic acid (18.9 g, 0.1 mol), $Pd(PPh_3)_4$ (3.5 g, 3.01 mmol) and $Na_2CO_3$ (31.9 g, 0.3 mol) were added to toluene 800 mL, EtOH 200 mL and purified water 200 mL. After stirring the reaction mixture for 3 hours at 70 to 80° C., an aqueous layer was removed from the mixture by a gravity separation. The obtained organic layer was concentrated, and then was purified by silica column chromatography to obtain compound C-2-2 (15 g, 47%).

Preparation of Compound C-9

After suspending compound C-2-2 (4.6 g, 14.7 mmol) and compound C-2-1 (5 g, 12.2 mmol) in DMF 80 mL, 60% NaH (881 g, 22 mmol) was added to the mixture at room temperature. The obtained reaction mixture was stirred for 12 hours. After adding purified water (1 L), the mixture was filtered under reduced pressure. The obtained solid was triturated with MeOH/EA, was dissolved in MC, was filtered through silica, and then was triturated with MC/n-hexane to obtain compound C-9 (4 g, 47.4%).

PREPARATION EXAMPLE 2

Preparation of Compound C-15

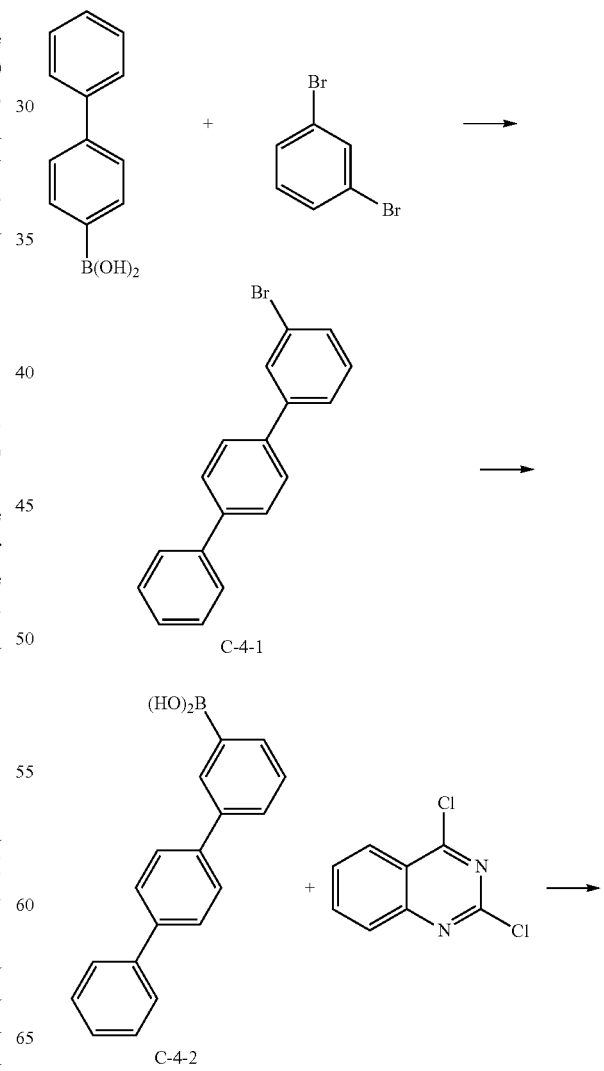

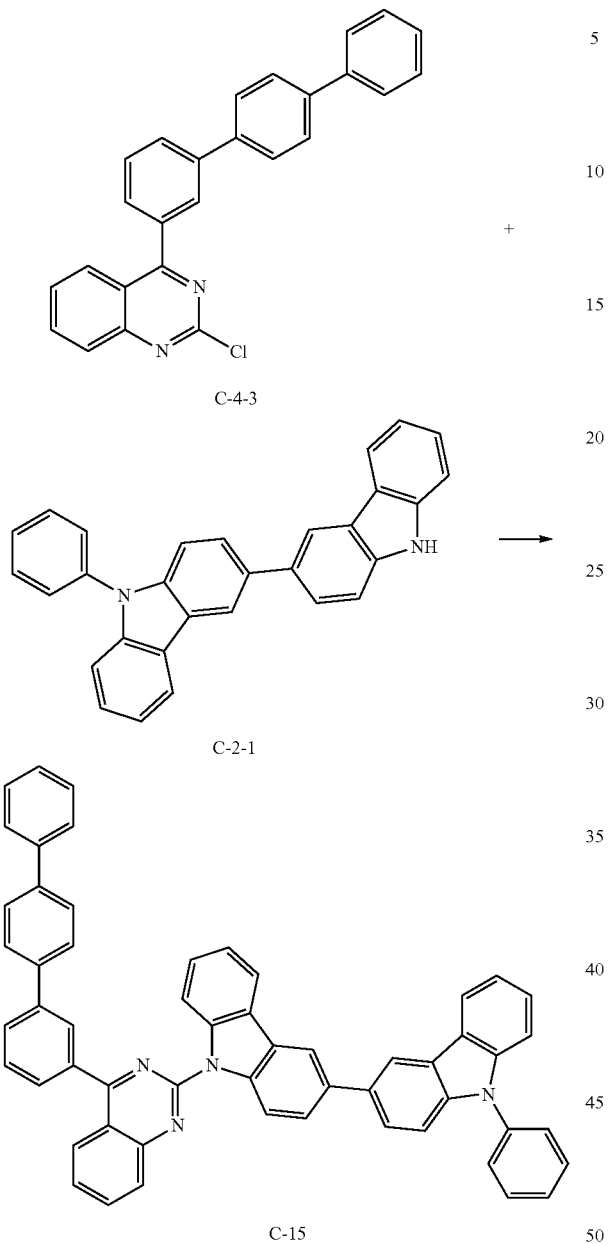

mixture was stirred for 1 hour. B(Oi-Pr)$_3$ (82 mL, 356 mmol) was added slowly to the mixture, and then the mixture was stirred for 2 hours. The mixture was quenched by adding 2 M HCl, was extracted with distilled water and EA, and then was recrystallized with hexane and acetone. Compound C-4-2 (43 g, 88.0%) was obtained.

Preparation of Compound C-4-3

2,4-dichloroquinazoline (20 g, 73 mmol), compound C-4-2 (15 g, 73 mmol), Pd(PPh$_3$)$_4$ (3.5 g, 2.2 mmol) and Na$_2$CO$_3$ (23 g, 241 mmol) were dissolved in toluene (500 mL), EtOH (100 mL) and distilled water (100 mL), and then was stirred for 5 hours at 100° C. The reaction mixture was distillated under reduced pressure to obtain an organic layer, and then was triturated with MeOH. The obtained solid was dissolved in MC, was filtered through silica, and then was triturated with MC and hexane to obtain compound C-4-3 (19.5 g, 68%).

Preparation of Compound C-15

After suspending compound C-2-1 (5 g, 12.2 mmol) and compound C-4-3 (4.6 g, 11.6 mmol) in DMF 80 mL, 60% NaH (881 mg, 22 mmol) was added to the mixture at room temperature. The obtained reaction mixture was stirred for 12 hours. After adding purified water (1 L), the mixture was filtered under reduced pressure. The obtained solid was triturated with MeOH/EA, was triturated with DMF, and then was triturated with EA/THF. The resultant was dissolved in MC, was filtered through silica, and then was triturated with MeOH/EA. Compound C-15 (5.1 g, 57%) was obtained.

PREPARATION EXAMPLE 3

Preparation of Compound C-29

Preparation of Compound C-4-1

After dissolving biphenyl-4-yl boronic acid (157 g, 554 mmol), 1,3-dibromobenzene (100 g, 581.7 mmol), Pd(PPh$_3$)$_4$ (13 g, 11.08 mmol) and Na$_2$CO$_3$ (150 g, 1.385 mol) in toluene (3.5 L), EtOH (0.7 L) and distilled water (0.7 L), the reaction mixture was stirred for 3 hours at 90° C. The mixture was extracted with EA and distilled water, was dissolved in chloroform (10 L) by heat, and then was filtered through silica. After triturating the resultant with EA and hexane, the resultant was triturated with EA and MeOH to obtain compound C-4-1 (94 g, 60%).

Preparation of Compound C-4-2

After dissolving compound C-4-1 (55 g, 178 mmol) in THF (800 mL), 2.5 M n-BuLi in hexane (106 mL, 267 mmol) was added to the reaction mixture at −78° C., and then the

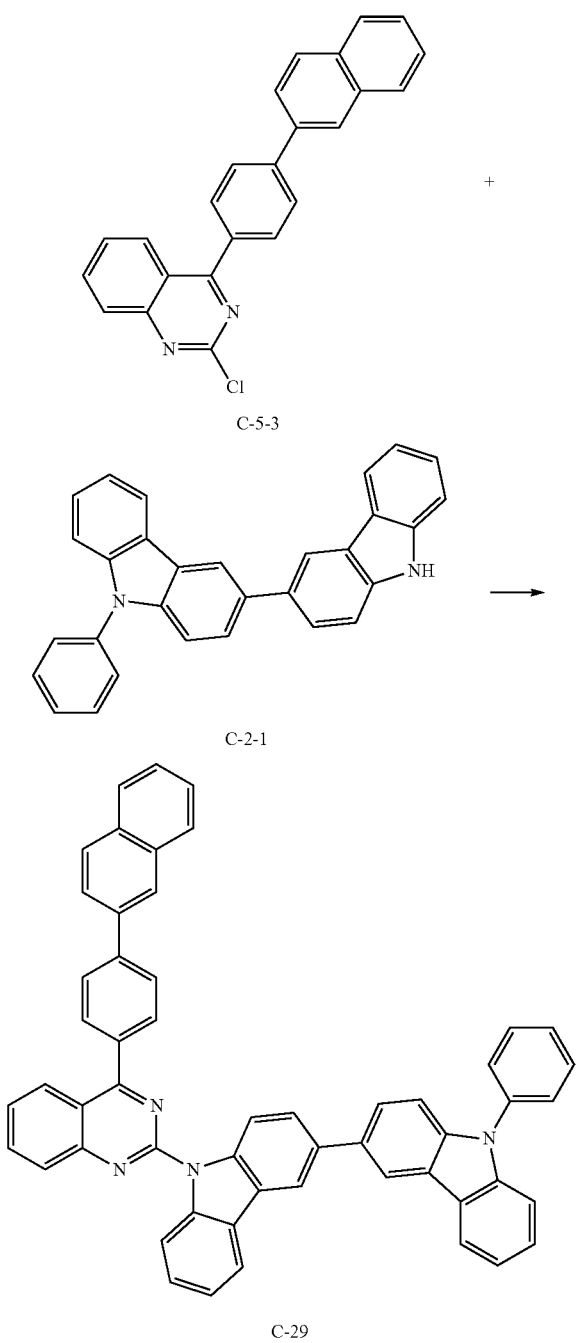

Preparation of Compound C-5-1

After dissolving 2-naphthylboronic acid (157 g, 554 mmol), 1-bromo-4-iodobenzene (100 g, 581.7 mmol), Pd(PPh$_3$)$_4$ (13 g, 11.08 mmol) and Na$_2$CO$_3$ (150 g, 1.385 mol) in toluene (3.5 L), EtOH (0.7 L) and distilled water (0.7 L), the reaction mixture was stirred for 3 hours at 90° C. The mixture was extracted with EA and distilled water, was dissolved in chloroform (10 L) by heat, and then was filtered through silica. After triturating the resultant with EA and hexane, the resultant was triturated with EA and MeOH to obtain compound C-5-1 (94 g, 60%).

Preparation of Compound C-5-2

After dissolving compound C-5-1 (94 g, 332 mmol) in THF (800 mL), 2.5 M n-BuLi in hexane (80 mL, 386.4 mmol) was added to the reaction mixture at −78° C., and then the mixture was stirred for 1 hour. B(OMe)$_3$ (28 mL, 498 mmol) was added slowly to the mixture, and then the mixture was stirred for 2 hours. The mixture was quenched by adding 2 M HCl, was extracted with distilled water and EA, and then was recrystallized with hexane and acetone. Compound C-5-2 (57 g, 67.0%) was obtained.

Preparation of Compound C-5-3

2,4-dichloroquinazoline (46 g, 230 mmol), compound C-5-2 (57 g, 230 mmol), Pd(PPh$_3$)$_4$ (10.6 g, 9.2 mmol) and Na$_2$CO$_3$ (73 g, 690 mmol) were dissolved in toluene (1.1 L), EtOH (230 mL) and distilled water (350 mL), and then was stirred for 5 hours at 100° C. The reaction mixture was distillated under reduced pressure to obtain an organic layer, and then was triturated with MeOH. The obtained solid was dissolved in MC, was filtered through silica, and then was triturated with MC and hexane to obtain compound C-5-3 (51 g, 99.9%).

Preparation of Compound C-29

After suspending compound C-2-1 (5 g, 12.2 mmol) and compound C-5-3 (4.5 g, 12.2 mmol) in DMF 80 mL, 60% NaH (881 mg, 22 mmol) was added to the mixture at room temperature. The obtained reaction mixture was stirred for 12 hours. After adding purified water (1 L), the mixture was filtered under reduced pressure. The obtained solid was triturated with MeOH/EA, was triturated with DMF, and then was triturated with EA/THF. The resultant was dissolved in MC, was filtered through silica, and then was triturated with MeOH/EA. Compound C-29 (1.8 g, 20%) was obtained.

In general, as to all teachings herein, the use of the terms "comprising" or "including" to describe combinations of elements, ingredients, components or steps herein also contemplates embodiments that consist essentially of, or even consist of the elements, ingredients, components or steps. Many embodiments, as well as many applications besides the examples provided, will be apparent to those of skill in the art upon reading the above description. The scope of the invention should, therefore, be determined not with reference to the above description, but should instead be determined with reference to the appended claims, along with the full scope of equivalents to which such claims are entitled.

What is claimed is:

1. A light emitting layer, comprising:
   an organic electroluminescent compound as a host material in the layer; and
   an iridium complex dopant,
   wherein the organic electroluminescent compound is represented by the following Formula 1; and the iridium complex dopant is represented by the following Formula 2:

[Formula 1]

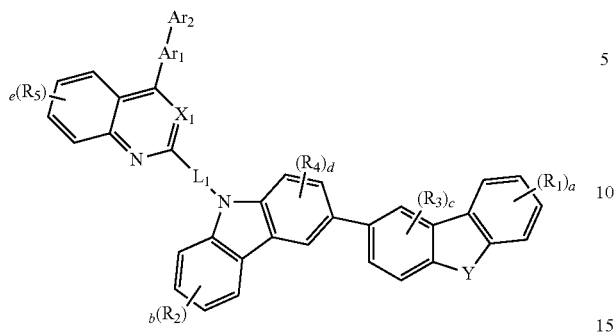

wherein:
$L_1$ represents a single bond;
$X_1$ represents N;
Y represents $—NR_{13}—$;
$Ar_1$ represents a single bond, a substituted or unsubstituted 5- to 30-membered heteroarylene group, a substituted or unsubstituted (C6-C30)arylene group;
$Ar_2$ represents hydrogen, deuterium, a substituted or unsubstituted (C1-C30)alkyl group, a substituted or unsubstituted (C6-C30)aryl group, or a substituted or unsubstituted 5- to 30-membered heteroaryl group;
$R_1$ to $R_5$ each independently represent hydrogen, deuterium, a halogen, as substituted or unsubstituted (C1-C30)alkyl group, a substituted or unsubstituted (C6-C30)aryl group, a substituted or unsubstituted 5- to 30-membered heteroaryl group, a substituted or unsubstituted (C3-C30)cycloalkyl group, a substituted or unsubstituted 5- to 7-membered heterocycloalkyl group, a substituted or unsubstituted (C6-C30)aryl(C1-C30)alkyl group, a substituted or unsubstituted (C6-C30)aryl group fused with at least one (C3-C30)cycloalkyl group, a 5- or 7-membered heterocycloalkyl group fused with at least one substituted or unsubstituted (C6-C30)aromatic ring, (C3-C30)cycloalkyl group fused with at least one substituted or unsubstituted (C6-C30)aromatic ring, $—NR_{14}R_{15}$, $—SiR_{16}R_{17}R_{18}$, $—SR_{19}$, $—OR_{20}$, a substituted or unsubstituted (C2-C30)alkenyl group, a substituted or unsubstituted (C2-C30)alkynyl group, a cyano group, a nitro group, or a hydroxyl group; or are linked to an adjacent substituent via a substituted or unsubstituted (C3-C30)alkylene group or a substituted or unsubstituted (C3-C30)alkenylene group to form a mono- or polycyclic alicyclic ring or a mono- or polycyclic aromatic ring whose carbon atom(s) may be substituted by at least one hetero atom selected from nitrogen, oxygen and sulfur;
$R_{13}$ to $R_{20}$ have the same meaning as one of $R_1$ to $R_5$,
a, b and e each independently represent an integer of 1 to 4; where a, b or e is an integer of 2 or more, each of $R_1$, each of $R_2$ or each of $R_5$ is the same or different;
c and d each independently represent an integer of 1 to 3; where c or d is an integer of 2 or more, each of $R_3$ or each of $R_4$ is the same or different; and
the heterocycloalkyl group and the heteroaryl(ene) group contain at least one hetero atom selected from B, N, O, S, P(=O), Si and P, and $M^1L^{101}L^{102}L^{103}$ [Formula 2]

wherein
$M^1$ is Ir;
$L^{101}$ and $L^{102}$ are the same and represent

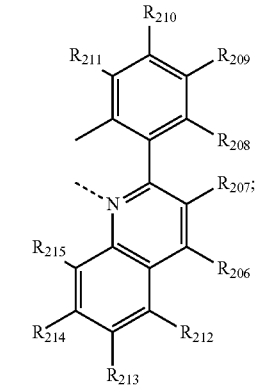

and
$L^{103}$ represents

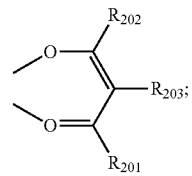

wherein $R_{201}$ to $R_{203}$ each independently represent hydrogen, deuterium, or a (C1-C30)alkyl group;
$R_{206}$ to $R_{208}$, $R_{210}$, and $R_{212}$ to $R_{215}$ each independently represent hydrogen, deuterium, a substituted or unsubstituted (C1-C30)alkyl group, or a substituted or unsubstituted (C6-C30)aryl group; and
$R_{209}$ and $R_{211}$ each independently represent a substituted or unsubstituted (C1-C30)alkyl group.

2. The light emitting layer of claim 1, wherein $R_{209}$ and $R_{211}$ each independently represent unsubstituted (C1-C10) alkyl group, and wherein $R_{207}$, $R_{208}$, $R_{210}$, $R_{214}$ and $R_{215}$ each independently represent hydrogen or deuterium.

3. The light emitting layer of claim 1, wherein the iridium complex dopant is selected from:

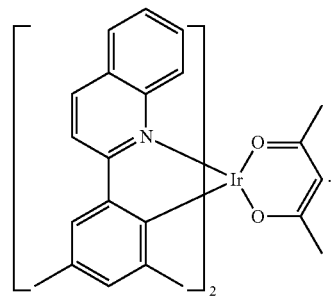

4. The light emitting layer of claim 1, wherein the iridium complex dopant is:

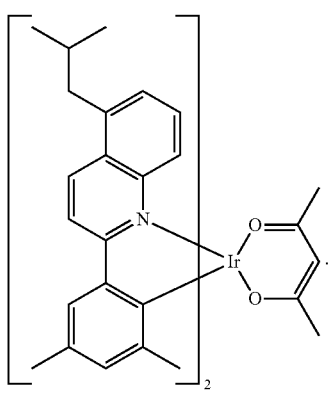

5. The light emitting layer of claim 1, wherein $R_{13}$ is a substituted or unsubstituted (C1-C30)alkyl group, a substituted or unsubstituted (C6-C30)aryl group, or a substituted or unsubstituted 5- to 30-membered heteroaryl group, a substituted or unsubstituted (C6-C30)aryl group fused with at least one (C3-C30)cycloalkyl group, a 5- or 7-membered heterocycloalkyl group fused with at least one substituted or unsubstituted (C6-C30)aromatic ring, or a (C3-C30)cycloalkyl group fused with at least one substituted or unsubstituted (C6-C30)aromatic ring.

6. The light emitting layer of claim 2, wherein $R_{13}$ is a substituted or unsubstituted (C1-C30)alkyl group, a substituted or unsubstituted (C6-C30)aryl group, or a substituted or unsubstituted 5- to 30-membered heteroaryl group.

7. The light emitting layer of claim 2, wherein $R_{13}$ is substituted or unsubstituted (C6-C30)aryl group.

8. The light emitting layer of claim 1, wherein the organic electroluminescent compound as a host material is selected from the following compounds C-1, C-5, C-9, or C-77:

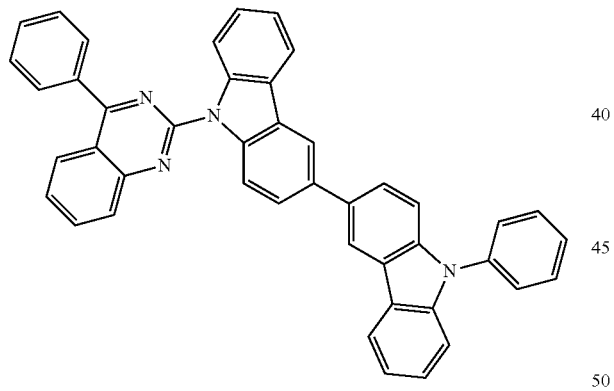

C-1

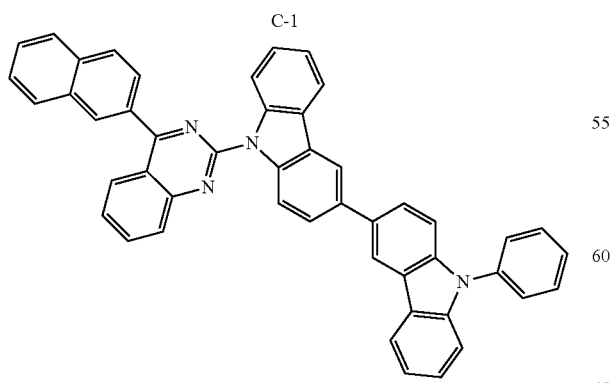

C-5

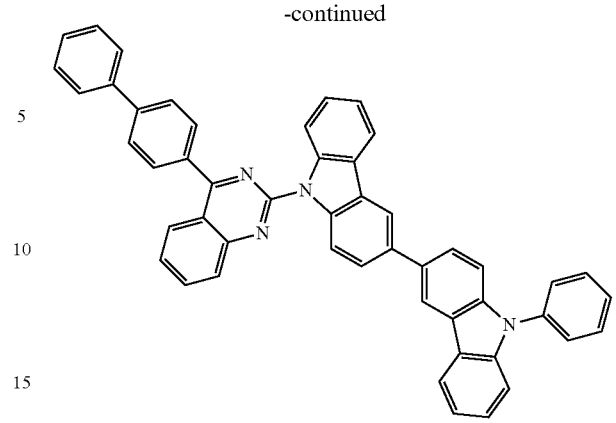

C-9

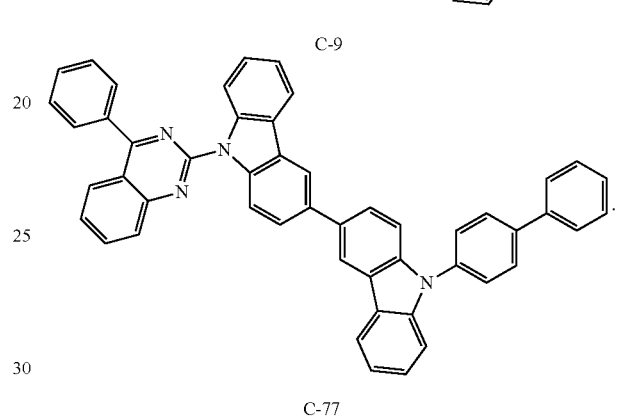

C-77

9. The light emitting layer of claim 3, wherein the organic electroluminescent compound as a host material is selected from the following compounds C-1, C-5, C-9, or C-77:

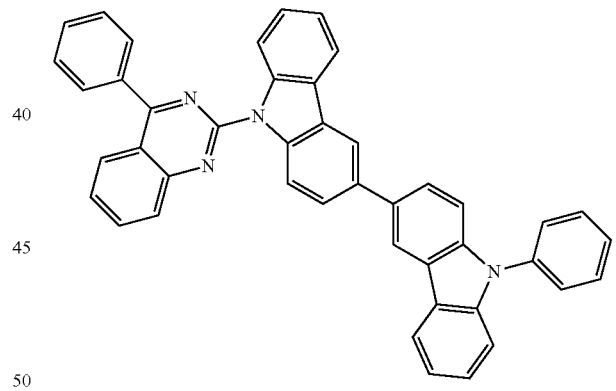

C-1

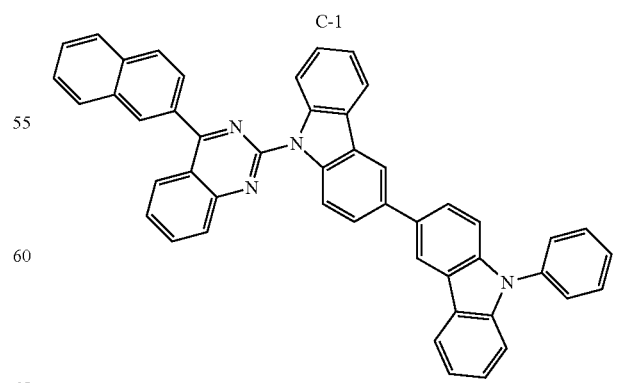

C-5

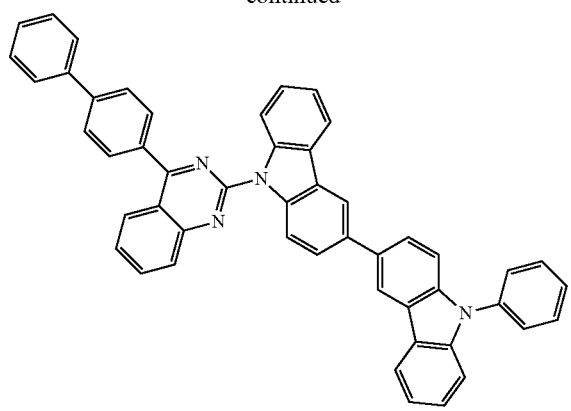
C-9
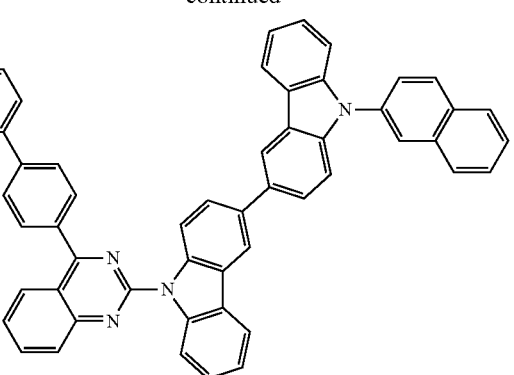
C-136
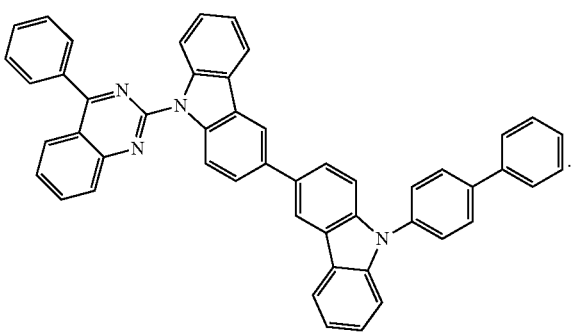
C-77
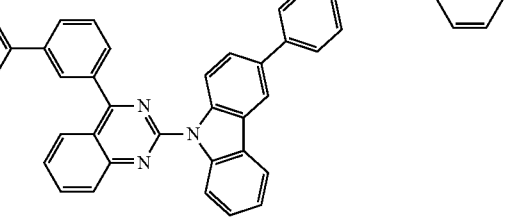
C-137
10. The light emitting layer of claim 1, wherein the organic electroluminescent compound as a host material is selected from the following compounds C-135, C-136 or C-137:
11. The light emitting layer of claim 4, wherein the organic electroluminescent compound as a host material is selected from the following compounds C-135, C-136 of C-137:
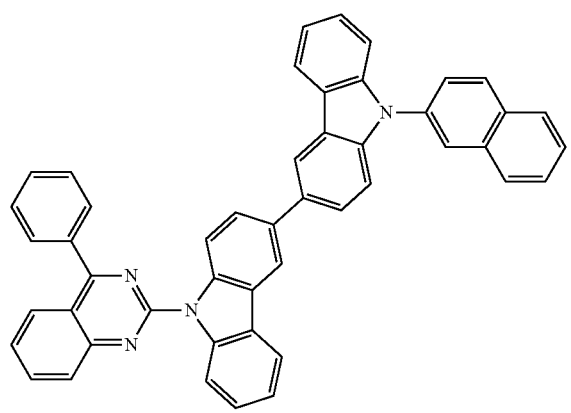
C-135
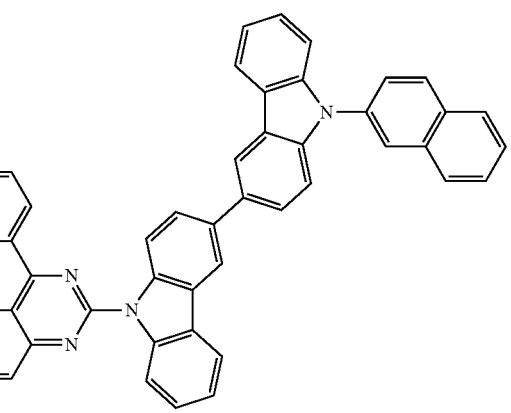
C-135

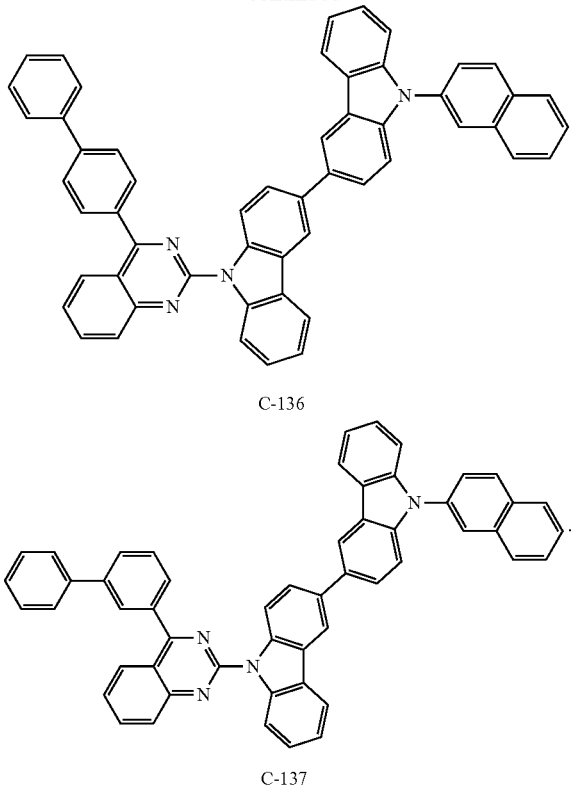

C-136

C-137

12. The light emitting layer of claim 3, wherein one of (a) $R_1$ to $R_5$ each independently represent hydrogen or a substituted or unsubstituted (C6-C30)aryl group; (b) $R_3$ represents a substituted or unsubstituted (C6-C30)aryl group; or (c) $R_4$ represents a substituted or unsubstituted (C6-C30)aryl group.

13. The light emitting layer of claim 4, wherein one of (a) $R_1$ to $R_5$ each independently represent hydrogen or a substituted or unsubstituted (C6-C30)aryl group; (b) $R_3$ represents a substituted or unsubstituted (C6-C30)aryl group; or (c) $R_4$ represents a substituted or unsubstituted (C6-C30)aryl group.

14. The light emitting layer of claim 3, wherein a ratio of an amount by weight of the host material to the iridium complex ranges from about 100:1 to about 10:1.

15. The light emitting layer of claim 14, wherein the layer luminesces red upon application of a driving voltage, and wherein the light emitting layer exhibits a peak intensity at a wavelength within a range of about 600 nm to about 700 nm and the host exhibits a glass transition temperature ($T_g$) of at least about 80° C.

16. The light emitting layer of claim 4, wherein a ratio of an amount by weight of the host material to the iridium complex ranges from about 100:1 to about 10:1.

17. The light emitting layer of claim 16, wherein the layer luminesces red upon application of a driving voltage, and wherein the light emitting layer exhibits a peak intensity at a wavelength within a range of about 600 nm to about 700 nm and the host exhibits a glass transition temperature ($T_g$) of at least about 80° C.

18. An organic electroluminescent device comprising an anode, a cathode, and the light emitting layer according to claim 3 disposed between the anode and the cathode.

19. An organic electroluminescent device comprising an anode, a cathode, and the light emitting layer according to claim 4 disposed between the anode and the cathode.

20. An organic electroluminescent device comprising an anode, a cathode, and the light emitting layer according to claim 9 disposed between the anode and the cathode.

* * * * *

UNITED STATES PATENT AND TRADEMARK OFFICE
CERTIFICATE OF CORRECTION

PATENT NO. : 9,287,512 B2
APPLICATION NO. : 14/825517
DATED : March 15, 2016
INVENTOR(S) : Hee-Choon Ahn et al.

It is certified that error appears in the above-identified patent and that said Letters Patent is hereby corrected as shown below:

On The Title Page, Item (56)

Page 2, Under Other Publications, Line 9, "(Mar. 10, 2020)" should be "(Mar. 10, 2010)"

In The Claims

Column 81, Line 31, "as substituted" should be "a substituted"

Column 87, Line 33, "of (a)" should be "of: (a)"

Column 87, Line 38, "of (a)" should be "of: (a)"

Signed and Sealed this
Third Day of May, 2016

Michelle K. Lee
*Director of the United States Patent and Trademark Office*